(12) United States Patent
Kassab et al.

(10) Patent No.: US 10,940,167 B2
(45) Date of Patent: Mar. 9, 2021

(54) METHODS AND USES OF BIOLOGICAL TISSUES FOR VARIOUS STENT AND OTHER MEDICAL APPLICATIONS

(71) Applicant: CVDevices, LLC, San Diego, CA (US)

(72) Inventors: Ghassan S. Kassab, San Diego, CA (US); Jose A. Navia, Sr., Buenos Aires (AR); Jorge Jordana, Buenos Aires (AR); Zachary C. Berwick, Indianapolis, IN (US)

(73) Assignee: CVDevices, LLC, San Diego, CA (US)

( * ) Notice: Subject to any disclaimer, the term of this patent is extended or adjusted under 35 U.S.C. 154(b) by 215 days.

(21) Appl. No.: 14/377,619

(22) PCT Filed: Feb. 11, 2013

(86) PCT No.: PCT/US2013/025591
§ 371 (c)(1),
(2) Date: Aug. 8, 2014

(87) PCT Pub. No.: WO2013/120082
PCT Pub. Date: Aug. 15, 2013

(65) Prior Publication Data
US 2015/0064140 A1 Mar. 5, 2015

Related U.S. Application Data

(60) Provisional application No. 61/597,406, filed on Feb. 10, 2012, provisional application No. 61/640,381, filed on Apr. 30, 2012.

(51) Int. Cl.
*A61F 2/24* (2006.01)
*A61K 35/42* (2015.01)
(Continued)

(52) U.S. Cl.
CPC ............ *A61K 35/42* (2013.01); *A61F 2/2415* (2013.01); *A61F 2/2418* (2013.01);
(Continued)

(58) Field of Classification Search
CPC ...... A61F 2/24; A61L 2430/40; A61L 27/386; A61L 27/3662; A61L 2430/20; A61L 27/3604
(Continued)

(56) References Cited

U.S. PATENT DOCUMENTS 3,012,882 A 12/1961 Muldawer et al.
3,014,104 A 12/1961 Cobine et al.
(Continued)

FOREIGN PATENT DOCUMENTS

AU 2003265468 8/2002
AU 2002248669 10/2002
(Continued)

OTHER PUBLICATIONS

Ali Mirnajafia, Jeremy Raymera, Michael J. Scottb, Michael S. Sacks, The effects of collagen fiber orientation on the flexural properties of pericardial heterograft biomaterials, Dec. 7, 2003, Elsevier, Biomaterials (26), 795-804.*
(Continued)

*Primary Examiner* — Brian E Pellegrino
(74) *Attorney, Agent, or Firm* — MacMillan, Sobanski & Todd, LLC

(57) ABSTRACT

Methods and uses of biological tissues for various stent and other medical applications. In an exemplary embodiment of a method of processing a tissue of the present disclosure, the method comprises the steps of acquiring a mammalian tissue comprising at least a portion of a pulmonary region tissue, selecting a sample of pulmonary region tissue from the at least a portion of a pulmonary region tissue, and fixing the
(Continued)

sample of pulmonary region tissue using a fixative, resulting in a fixed sample. In at least one embodiment, the step of selecting a sample of pulmonary region tissue comprises selecting a sample of pulmonary ligament tissue from the mammalian tissue.

12 Claims, 13 Drawing Sheets

(51) Int. Cl.
  *A61L 27/36* (2006.01)
  *A61L 31/08* (2006.01)
(52) U.S. Cl.
  CPC ........... *A61L 27/3604* (2013.01); *A61L 31/08* (2013.01); *A61F 2/2475* (2013.01)
(58) Field of Classification Search
  USPC ........................................................ 8/94.11
  See application file for complete search history.

(56) References Cited

U.S. PATENT DOCUMENTS

| | | |
|---|---|---|
| 3,063,967 A | 11/1962 | Schultz |
| 3,169,945 A | 2/1965 | Hostettler et al. |
| 3,174,851 A | 3/1965 | Buehler et al. |
| 3,391,126 A | 7/1968 | Baggett et al. |
| 3,464,065 A | 9/1969 | Cromie |
| 3,583,391 A | 6/1971 | Cox et al. |
| 3,589,392 A | 6/1971 | Meyer |
| 3,645,941 A | 2/1972 | Snapp et al. |
| 3,710,744 A | 1/1973 | Goodenough et al. |
| 3,736,598 A | 6/1973 | Bellhouse et al. |
| 3,737,919 A | 6/1973 | Child |
| 3,772,137 A | 11/1973 | Tolliver |
| 3,912,692 A | 10/1975 | Casey et al. |
| 3,942,532 A | 3/1976 | Hunter et al. |
| 3,953,566 A | 4/1976 | Gore |
| 3,983,581 A | 10/1976 | Angell et al. |
| 4,052,988 A | 10/1977 | Doddi et al. |
| 4,076,807 A | 2/1978 | Trinh et al. |
| 4,093,061 A | 6/1978 | Horak |
| 4,106,129 A | 8/1978 | Carpentier et al. |
| 4,218,782 A | 8/1980 | Rygg |
| 4,222,126 A | 9/1980 | Boretos et al. |
| 4,243,775 A | 1/1981 | Rosensaft et al. |
| 4,274,292 A | 1/1981 | Angell |
| 4,272,854 A | 6/1981 | Bokros |
| 4,275,469 A | 6/1981 | Gabbay |
| 4,297,749 A | 11/1981 | Davis et al. |
| 4,300,565 A | 11/1981 | Rosensaft et al. |
| 4,328,592 A | 5/1982 | Klawitier |
| 4,340,977 A | 7/1982 | Brownlee et al. |
| 4,345,340 A | 8/1982 | Rosen |
| 4,350,492 A | 9/1982 | Wright et al. |
| 4,364,126 A | 12/1982 | Rosen |
| 4,429,080 A | 1/1984 | Casey et al. |
| 4,440,789 A | 4/1984 | Mattel et al. |
| 4,441,216 A | 4/1984 | Ionescu et al. |
| 4,470,157 A | 9/1984 | Love |
| 4,494,531 A | 1/1985 | Gianturco |
| 4,506,394 A | 3/1985 | Bedard |
| 4,535,483 A | 8/1985 | Klawitter et al. |
| 4,549,921 A | 10/1985 | Wolfe, Jr. |
| 4,559,945 A | 12/1985 | Koelmel et al. |
| 4,564,014 A | 1/1986 | Fogarty |
| 4,580,568 A | 4/1986 | Gianturco |
| 4,591,630 A | 5/1986 | Gertzman et al. |
| 4,605,730 A | 8/1986 | Shalaby et al. |
| 4,624,256 A | 11/1986 | Messier et al. |
| 4,643,732 A | 2/1987 | Pietsch et al. |
| 4,643,734 A | 2/1987 | Lin |
| 4,653,497 A | 3/1987 | Bezwada et al. |
| 4,657,024 A | 4/1987 | Coneys |
| 4,661,300 A | 4/1987 | Daugherty |
| 4,665,906 A | 5/1987 | Jervis |
| 4,665,918 A | 5/1987 | Garza et al. |
| 4,666,442 A | 5/1987 | Arru et al. |
| 4,675,361 A | 6/1987 | Ward et al. |
| 4,681,588 A * | 7/1987 | Ketharanathan ........ A61L 15/40 128/899 |
| 4,692,164 A | 9/1987 | Dzemeshkevich |
| 4,700,704 A | 10/1987 | Jamiolkowski et al. |
| 4,731,074 A | 3/1988 | Rousseau et al. |
| 4,731,075 A | 3/1988 | Gallo Mezo et al. |
| 4,755,593 A | 7/1988 | Lauren |
| 4,759,758 A | 7/1988 | Gabbay |
| 4,762,129 A | 8/1988 | Bonzel |
| 4,776,337 A | 10/1988 | Palmaz |
| 4,787,901 A | 11/1988 | Baykut |
| 4,788,979 A | 12/1988 | Jarrett et al. |
| 4,791,929 A | 12/1988 | Jarrett et al. |
| 4,798,611 A | 1/1989 | Freeman |
| 4,800,603 A | 1/1989 | Jaffe |
| 4,806,595 A | 2/1989 | Noishiki et al. |
| 4,816,028 A | 3/1989 | Kapadia |
| 4,816,029 A | 3/1989 | Penny et al. |
| 4,832,055 A | 5/1989 | Palestrant |
| 4,836,204 A | 6/1989 | Landymore et al. |
| 4,838,267 A | 6/1989 | Jamiolkowski et al. |
| 4,851,000 A | 7/1989 | Gupta |
| 4,856,510 A | 8/1989 | Kowalewski |
| 4,856,516 A | 8/1989 | Hillstead |
| 4,861,830 A | 8/1989 | Ward et al. |
| 4,872,875 A | 10/1989 | Hwang |
| 4,893,623 A | 1/1990 | Rosenbluth |
| 4,902,508 A | 2/1990 | Badylak et al. |
| 4,911,163 A | 3/1990 | Fina |
| 4,917,089 A | 4/1990 | Sideris |
| 4,923,465 A | 5/1990 | Knock et al. |
| 4,952,215 A | 8/1990 | Ouriel et al. |
| 4,956,178 A | 9/1990 | Badylak et al. |
| 4,969,458 A | 11/1990 | Wiktor |
| 4,992,027 A | 2/1991 | Acosta |
| 4,994,071 A | 2/1991 | MacGregor |
| 4,994,074 A | 2/1991 | Bezwada et al. |
| 4,994,077 A | 2/1991 | Dobben |
| 5,007,923 A | 4/1991 | Bezwada et al. |
| 5,017,664 A | 5/1991 | Grasel et al. |
| 5,019,085 A | 5/1991 | Hillstead |
| 5,020,612 A | 6/1991 | Williams |
| 5,024,671 A | 6/1991 | Tu et al. |
| 5,024,841 A | 6/1991 | Chu et al. |
| 5,035,706 A | 7/1991 | Gianturco et al. |
| 5,037,434 A | 8/1991 | Lane |
| 5,041,126 A | 8/1991 | Gianturco |
| 5,047,048 A | 9/1991 | Bezwada et al. |
| 5,053,008 A | 10/1991 | Bajaj |
| 5,067,491 A | 11/1991 | Taylor, II et al. |
| 5,076,807 A | 12/1991 | Bezwada et al. |
| 5,080,665 A | 1/1992 | Jarrett et al. |
| 5,080,670 A | 1/1992 | Imamura et al. |
| 5,085,629 A | 2/1992 | Goldberg et al. |
| 5,100,433 A | 3/1992 | Bezwada et al. |
| 5,103,817 A | 4/1992 | Reisdorf et al. |
| 5,104,402 A | 4/1992 | Melbin |
| 5,104,404 A | 4/1992 | Wolff |
| 5,108,420 A | 4/1992 | Marks |
| 5,108,425 A | 4/1992 | Hwang |
| 5,110,064 A | 5/1992 | Kimura et al. |
| 5,116,365 A | 5/1992 | Hillstead |
| 5,116,564 A | 5/1992 | Jansen et al. |
| 5,133,725 A | 7/1992 | Quadri |
| 5,133,755 A | 7/1992 | Brekke |
| 5,139,515 A | 8/1992 | Robicsek |
| 5,163,953 A | 11/1992 | Vince |
| 5,167,628 A | 12/1992 | Boyles |
| 5,171,259 A | 12/1992 | Inoue |
| 5,174,295 A | 12/1992 | Christian et al. |
| 5,176,692 A | 1/1993 | Wilk et al. |
| 5,178,618 A | 1/1993 | Kandarpa |
| 5,178,632 A | 1/1993 | Hanson |
| 5,178,633 A | 1/1993 | Peters |

(56) References Cited

U.S. PATENT DOCUMENTS

| | | |
|---|---|---|
| 5,192,301 A | 3/1993 | Kamiya et al. |
| 5,192,313 A | 3/1993 | Budd et al. |
| 5,197,979 A | 3/1993 | Quintero et al. |
| 5,197,980 A | 3/1993 | Gorshkov |
| 5,201,314 A | 4/1993 | Bosley et al. |
| 5,201,757 A | 4/1993 | Heyn et al. |
| 5,226,889 A | 7/1993 | Sheiban |
| 5,234,457 A | 8/1993 | Andersen |
| 5,239,982 A | 8/1993 | Trauthen |
| 5,258,000 A | 11/1993 | Gianturco |
| 5,275,826 A | 1/1994 | Badylak et al. |
| 5,281,422 A | 1/1994 | Badylak et al. |
| 5,282,824 A | 2/1994 | Gianturco |
| 5,284,488 A | 2/1994 | Sideris |
| 5,289,831 A | 3/1994 | Bosley |
| 5,293,879 A | 3/1994 | Vonk et al. |
| 5,306,294 A | 4/1994 | Winston et al. |
| 5,314,444 A | 5/1994 | Gianturco |
| 5,314,472 A | 5/1994 | Fontaine |
| 5,314,473 A | 5/1994 | Godin |
| 5,322,062 A | 6/1994 | Servas |
| 5,327,891 A | 7/1994 | Rammler |
| 5,334,210 A | 8/1994 | Gianturco |
| 5,334,217 A | 8/1994 | Das |
| 5,342,387 A | 8/1994 | Summers |
| 5,344,426 A | 9/1994 | Lau et al. |
| 5,352,240 A | 10/1994 | Ross |
| 5,358,518 A | 10/1994 | Camilli |
| 5,366,473 A | 11/1994 | Winston et al. |
| 5,366,479 A | 11/1994 | McGarry et al. |
| 5,370,685 A | 12/1994 | Stevens |
| 5,376,113 A | 12/1994 | Jansen et al. |
| 5,380,320 A | 1/1995 | Morris |
| 5,383,892 A | 1/1995 | Cardon et al. |
| 5,387,235 A | 2/1995 | Chuter |
| 5,389,106 A | 2/1995 | Tower |
| 5,393,594 A | 2/1995 | Koyfman et al. |
| 5,397,311 A | 3/1995 | Walker |
| 5,397,331 A | 3/1995 | Himpens et al. |
| 5,397,355 A | 3/1995 | Marin et al. |
| 5,405,377 A | 4/1995 | Cragg |
| 5,405,381 A | 4/1995 | Olin |
| 5,411,552 A | 5/1995 | Andersen |
| 5,412,068 A | 5/1995 | Tang et al. |
| 5,413,599 A | 5/1995 | Imachi et al. |
| 5,417,708 A | 5/1995 | Hall et al. |
| 5,421,955 A | 6/1995 | Lau et al. |
| 5,425,744 A | 6/1995 | Fagan et al. |
| 5,433,727 A | 7/1995 | Sideris |
| 5,441,515 A | 8/1995 | Khosravi et al. |
| 5,443,496 A | 8/1995 | Schwartz |
| 5,449,373 A | 9/1995 | Pinchasik |
| 5,451,235 A | 9/1995 | Lock et al. |
| 5,456,713 A | 10/1995 | Chuter |
| 5,468,253 A | 11/1995 | Bezwada et al. |
| 5,486,193 A | 1/1996 | Bourne |
| 5,486,195 A | 1/1996 | Myers et al. |
| 5,489,297 A | 2/1996 | Duran |
| 5,500,014 A | 3/1996 | Quijano |
| 5,507,767 A | 4/1996 | Maeda et al. |
| 5,507,771 A | 4/1996 | gianturco |
| 5,514,154 A | 5/1996 | Lau et al. |
| 5,522,841 A | 6/1996 | Roby et al. |
| 5,527,354 A | 6/1996 | Fontaine et al. |
| 5,530,683 A | 6/1996 | Lindberg |
| 5,540,712 A | 7/1996 | Kleshinski et al. |
| 5,540,713 A | 7/1996 | Schnepp-Pesch et al. |
| 5,545,215 A | 8/1996 | Duran |
| 5,549,662 A | 8/1996 | Fordenbacher |
| 5,549,663 A | 8/1996 | Cottone, Jr. |
| 5,549,665 A | 8/1996 | Vesely et al. |
| 5,554,119 A | 9/1996 | Harrison et al. |
| 5,554,181 A | 9/1996 | Das |
| 5,554,185 A | 9/1996 | Block et al. |
| 5,554,389 A | 9/1996 | Badylak et al. |
| 5,562,728 A | 10/1996 | Lazarus et al. |
| 5,562,729 A | 10/1996 | Purdy |
| 5,571,168 A | 11/1996 | Toro |
| 5,589,563 A | 12/1996 | Ward et al. |
| 5,591,197 A | 1/1997 | Orth et al. |
| 5,591,198 A | 1/1997 | Boyle et al. |
| 5,595,571 A | 1/1997 | Jaffe |
| 5,603,698 A | 2/1997 | Roberts et al. |
| 5,607,442 A | 3/1997 | Fischell et al. |
| 5,607,445 A | 3/1997 | Summers |
| 5,607,465 A | 3/1997 | Camilli |
| 5,609,598 A | 3/1997 | Laufer et al. |
| 5,613,981 A | 3/1997 | Boyle et al. |
| 5,624,449 A | 4/1997 | Pham et al. |
| 5,628,791 A | 5/1997 | Bokros et al. |
| 5,630,829 A | 5/1997 | Lauterjung |
| 5,632,771 A | 5/1997 | Boatman et al. |
| 5,634,936 A | 6/1997 | Linden et al. |
| 5,636,641 A | 6/1997 | Fariabi |
| 5,641,324 A | 6/1997 | Bokros et al. |
| 5,643,312 A | 7/1997 | Fischell et al. |
| 5,643,317 A | 7/1997 | Pavcnik et al. |
| 5,653,727 A | 8/1997 | Wiktor |
| 5,662,675 A | 9/1997 | Polansky et al. |
| 5,667,523 A | 9/1997 | Bynon et al. |
| 5,668,288 A | 9/1997 | Storey et al. |
| 5,669,933 A | 9/1997 | Simon et al. |
| 5,681,346 A | 10/1997 | Orth et al. |
| 5,683,411 A | 11/1997 | Kavteladze et al. |
| 5,690,642 A | 11/1997 | Osborne et al. |
| 5,697,971 A | 12/1997 | Fischell et al. |
| 5,702,372 A | 12/1997 | Nelson |
| 5,702,421 A | 12/1997 | Schneidt |
| 5,705,181 A | 1/1998 | Cooper et al. |
| 5,707,389 A | 1/1998 | Louw et al. |
| 5,709,707 A | 1/1998 | Lock et al. |
| 5,711,969 A | 1/1998 | Patel et al. |
| 5,713,920 A | 2/1998 | Bezwada et al. |
| 5,713,950 A | 2/1998 | Cox |
| 5,713,953 A | 2/1998 | Vallana et al. |
| 5,720,777 A | 2/1998 | Jaffe |
| 5,725,519 A | 3/1998 | Penner |
| 5,725,534 A | 3/1998 | Rasmussen |
| 5,725,572 A | 3/1998 | Lam et al. |
| 5,728,158 A | 3/1998 | Lau et al. |
| 5,733,303 A | 3/1998 | Israel et al. |
| 5,733,325 A | 3/1998 | Robinson et al. |
| 5,733,337 A | 3/1998 | Carr, Jr. et al. |
| 5,735,893 A | 4/1998 | Lau et al. |
| 5,741,327 A | 4/1998 | Frantzen |
| 5,749,919 A | 5/1998 | Blanc |
| 5,755,776 A | 5/1998 | Al-Saadon |
| 5,755,777 A | 5/1998 | Chuter |
| 5,755,778 A | 5/1998 | Kleshinski |
| 5,755,781 A | 5/1998 | Jayaraman |
| 5,755,782 A * | 5/1998 | Love ............... A61F 2/2409 623/1.15 |
| 5,759,192 A | 6/1998 | Saunders |
| 5,762,625 A | 6/1998 | Igaki |
| 5,766,238 A | 6/1998 | Lau et al. |
| 5,769,780 A | 6/1998 | Hata et al. |
| 5,769,796 A | 6/1998 | Palermo et al. |
| 5,772,632 A | 6/1998 | Forman |
| 5,776,161 A | 7/1998 | Globerman |
| 5,776,188 A | 7/1998 | Shepherd et al. |
| 5,779,670 A | 7/1998 | Melman et al. |
| 5,779,729 A | 7/1998 | Severini |
| 5,792,114 A | 8/1998 | Fiore |
| 5,792,144 A | 8/1998 | Fischell et al. |
| 5,797,952 A | 8/1998 | Klein |
| 5,797,960 A | 8/1998 | Stevens et al. |
| 5,797,953 A | 9/1998 | Tekulve |
| 5,800,456 A | 9/1998 | Maeda et al. |
| 5,800,526 A | 9/1998 | Andersen et al. |
| 5,807,404 A | 9/1998 | Richter |
| 5,810,847 A | 9/1998 | Laufer et al. |
| 5,814,061 A | 9/1998 | Osborne et al. |
| 5,824,041 A | 10/1998 | Freislinger et al. |
| 5,824,042 A | 10/1998 | Lombardi et al. |

(56) References Cited

U.S. PATENT DOCUMENTS

| | | |
|---|---|---|
| 5,824,045 A | 10/1998 | Alt |
| 5,824,049 A | 10/1998 | Ragheb et al. |
| 5,824,062 A | 10/1998 | Patke et al. |
| 5,824,063 A | 10/1998 | Cox |
| 5,827,237 A | 10/1998 | Macoviak et al. |
| 5,833,694 A | 10/1998 | Poncet |
| 5,830,209 A | 11/1998 | Savage et al. |
| 5,833,671 A | 11/1998 | Macoviak et al. |
| 5,836,964 A | 11/1998 | Richter et al. |
| 5,840,081 A | 11/1998 | Andersen et al. |
| 5,843,090 A | 12/1998 | Schuetz |
| 5,843,117 A | 12/1998 | Alt et al. |
| 5,843,180 A | 12/1998 | Jaffe et al. |
| 5,843,181 A | 12/1998 | Jaffe et al. |
| 5,846,247 A | 12/1998 | Unworth et al. |
| 5,846,261 A | 12/1998 | Kotula et al. |
| 5,851,232 A | 12/1998 | Lois |
| 5,853,422 A | 12/1998 | Huebsch et al. |
| 5,855,597 A | 1/1999 | Jayaraman |
| 5,855,600 A | 1/1999 | Alt |
| 5,855,601 A | 1/1999 | Bessler et al. |
| 5,855,602 A | 1/1999 | Angell |
| 5,861,003 A | 1/1999 | Latson et al. |
| 5,865,723 A | 2/1999 | Love |
| 5,876,445 A | 3/1999 | Andersen et al. |
| 5,876,448 A | 3/1999 | Thompson et al. |
| 5,879,305 A | 3/1999 | Yock et al. |
| 5,879,366 A | 3/1999 | Shaw et al. |
| 5,879,382 A | 3/1999 | Boneau |
| 5,885,619 A | 3/1999 | Patel et al. |
| 5,891,128 A | 4/1999 | Gia et al. |
| 5,891,193 A | 4/1999 | Robinson et al. |
| 5,891,195 A | 4/1999 | Klostermeyer et al. |
| 5,895,419 A | 4/1999 | Tweden et al. |
| 5,895,420 A | 4/1999 | Mirsch, II et al. |
| 5,902,334 A | 5/1999 | Dwyer et al. |
| 5,907,893 A | 6/1999 | Zadno-Azizi et al. |
| 5,908,452 A | 6/1999 | Bokros et al. |
| 5,911,732 A | 6/1999 | Hojeibane |
| 5,925,063 A | 7/1999 | Khosravi |
| 5,926,016 A | 7/1999 | Pattantyus |
| 5,928,248 A | 7/1999 | Acker |
| 5,928,258 A | 7/1999 | Kahn |
| 5,935,148 A | 8/1999 | Villar et al. |
| 5,935,161 A | 8/1999 | Robinson |
| 5,937,861 A | 8/1999 | Augustine |
| 5,938,682 A | 8/1999 | Hojeibane |
| 5,944,733 A | 8/1999 | Engelson |
| 5,944,738 A | 8/1999 | Amplatz et al. |
| 5,947,995 A | 9/1999 | Samuels |
| 5,947,997 A | 9/1999 | Pavcnik et al. |
| 5,954,766 A | 9/1999 | Zadno-Azizi et al. |
| 5,955,110 A | 9/1999 | Patel et al. |
| 5,957,949 A | 9/1999 | Leonhardt et al. |
| 5,960,642 A | 10/1999 | Kim et al. |
| 5,961,546 A | 10/1999 | Robinson et al. |
| 5,968,096 A | 10/1999 | Whitson et al. |
| 5,980,565 A | 11/1999 | Jayaraman |
| 5,980,799 A | 11/1999 | Martakos et al. |
| 5,981,195 A | 11/1999 | Fuller et al. |
| 5,993,844 A | 11/1999 | Abraham et al. |
| 5,997,573 A | 12/1999 | Quijano et al. |
| 6,004,347 A | 12/1999 | McNamara et al. |
| 6,007,521 A | 12/1999 | Melman |
| 6,010,531 A | 1/2000 | Donlon et al. |
| 6,015,431 A | 1/2000 | Thornton et al. |
| 6,017,363 A | 1/2000 | Hojeibane |
| 6,022,359 A | 2/2000 | Frantzen et al. |
| 6,022,374 A | 2/2000 | Imran |
| 6,024,690 A | 2/2000 | Lee et al. |
| 6,027,525 A | 2/2000 | Suh et al. |
| 6,033,398 A | 3/2000 | Farley et al. |
| 6,036,687 A | 3/2000 | Laufer et al. |
| 6,042,606 A | 3/2000 | Frantzen |
| 6,053,940 A | 4/2000 | Wijay |
| 6,056,775 A | 5/2000 | Borghi et al. |
| 6,059,757 A | 5/2000 | Macoviak et al. |
| 6,059,779 A | 5/2000 | Mills |
| 6,059,826 A | 5/2000 | Bokros |
| 6,059,827 A | 5/2000 | Fenton |
| 6,063,113 A | 5/2000 | Kavteladze et al. |
| 6,074,419 A | 6/2000 | Healy et al. |
| 6,077,281 A | 6/2000 | Das |
| 6,077,291 A | 6/2000 | Das |
| 6,077,295 A | 6/2000 | Limon et al. |
| 6,077,296 A | 6/2000 | Shokoohi et al. |
| 6,080,182 A | 6/2000 | Shaw et al. |
| 6,090,035 A | 7/2000 | Campbell |
| 6,090,127 A | 7/2000 | Globerman |
| 6,096,027 A | 8/2000 | Layne |
| 6,096,052 A | 8/2000 | Callister et al. |
| 6,099,561 A | 8/2000 | Alt |
| 6,099,567 A | 8/2000 | Badylak et al. |
| 6,110,191 A | 8/2000 | Dehdashtian |
| 6,110,201 A | 8/2000 | Quijano et al. |
| 6,110,212 A | 8/2000 | Gregory |
| 6,096,070 A | 9/2000 | Ragneb et al. |
| 6,113,623 A | 9/2000 | Sgro |
| 6,117,157 A | 9/2000 | Tekulve |
| 6,117,159 A | 9/2000 | Huebsch et al. |
| 6,117,979 A | 9/2000 | Hendriks et al. |
| 6,123,721 A | 9/2000 | Jang |
| 6,126,685 A | 10/2000 | Lenker |
| 6,126,686 A | 10/2000 | Badylak et al. |
| 6,129,755 A | 10/2000 | Mathis et al. |
| 6,132,460 A | 10/2000 | Thompson |
| 6,132,461 A | 10/2000 | Thompson |
| 6,136,025 A | 10/2000 | Barbut et al. |
| 6,139,575 A | 10/2000 | Shu et al. |
| 6,143,016 A | 11/2000 | Bleam |
| 6,143,022 A | 11/2000 | Shull et al. |
| 6,146,416 A | 11/2000 | Andersen et al. |
| 6,149,660 A | 11/2000 | Laufer et al. |
| 6,149,680 A | 11/2000 | Shelso |
| 6,159,237 A | 12/2000 | Alt et al. |
| 6,162,245 A | 12/2000 | Jayaraman |
| 6,168,614 B1 | 1/2001 | Andersen et al. |
| 6,168,617 B1 | 1/2001 | Blaeser et al. |
| 6,174,331 B1 | 1/2001 | Moe et al. |
| 6,176,875 B1 | 1/2001 | Lenker |
| 6,178,968 B1 | 1/2001 | Louw et al. |
| 6,179,858 B1 | 1/2001 | Squire et al. |
| 6,183,511 B1 | 2/2001 | Patke et al. |
| 6,183,512 B1 | 2/2001 | Howanec et al. |
| 6,187,036 B1 | 2/2001 | Shaolian et al. |
| 6,187,039 B1 | 2/2001 | Hiles et al. |
| 6,190,406 B1 | 2/2001 | Durerig et al. |
| 6,193,731 B1 | 2/2001 | Oppelt |
| 6,197,049 B1 | 3/2001 | Shaolian et al. |
| 6,200,336 B1 | 3/2001 | Pavcnik et al. |
| 6,206,907 B1 | 3/2001 | Marino et al. |
| 6,206,931 B1 | 3/2001 | Cook et al. |
| 6,214,029 B1 | 4/2001 | Thill et al. |
| 6,216,493 B1 | 4/2001 | Weston et al. |
| 6,221,091 B1 | 4/2001 | Khosravi |
| 6,231,507 B1 | 5/2001 | Zikorus et al. |
| 6,231,561 B1 | 5/2001 | Frazier et al. |
| 6,231,598 B1 | 5/2001 | Berry |
| 6,235,050 B1 | 5/2001 | Quiachon et al. |
| 6,235,053 B1 | 5/2001 | Jang |
| 6,238,409 B1 | 5/2001 | Hojeibane |
| 6,238,416 B1 | 5/2001 | Sideris |
| 6,241,763 B1 | 6/2001 | Drasler et al. |
| 6,245,102 B1 | 6/2001 | Jayaraman |
| 6,254,611 B1 | 7/2001 | Vrba |
| 6,254,631 B1 | 7/2001 | Thompson |
| 6,254,636 B1 | 7/2001 | Peredo |
| 6,254,642 B1 | 7/2001 | Taylor |
| 6,264,700 B1 | 7/2001 | Kilcoyne et al. |
| 6,280,467 B1 | 8/2001 | Leonhardt |
| 6,233,968 B1 | 9/2001 | Taheri |
| 6,283,990 B1 | 9/2001 | Kanesaka |
| 6,287,330 B1 | 9/2001 | Johansson et al. |
| 6,287,332 B1 | 9/2001 | Bolz et al. |

(56) References Cited

U.S. PATENT DOCUMENTS

| | | |
|---|---|---|
| 6,287,334 B1 | 9/2001 | Moll et al. |
| 6,287,336 B1 | 9/2001 | Globerman et al. |
| 6,293,966 B1 | 9/2001 | Frantzen |
| 6,296,657 B1 | 10/2001 | Brucker |
| 6,299,604 B1 | 10/2001 | Ragheb et al. |
| 6,299,635 B1 | 10/2001 | Frantzen |
| 6,299,636 B1 | 10/2001 | Schmitt et al. |
| 6,299,637 B1 | 10/2001 | Shaplian |
| 6,312,465 B1 | 11/2001 | Griffin et al. |
| 6,312,474 B1 | 11/2001 | Francis et al. |
| 6,312,549 B1 | 11/2001 | Huang et al. |
| 6,315,793 B1 | 11/2001 | Bokros et al. |
| 6,319,281 B1 | 11/2001 | Patel |
| 6,325,819 B1 | 12/2001 | Pavcnik et al. |
| 6,328,727 B1 | 12/2001 | Frazier et al. |
| 6,328,763 B1 | 12/2001 | Love et al. |
| 6,334,052 B1 | 12/2001 | Nordstrand |
| 6,334,871 B1 | 1/2002 | Dor et al. |
| 6,334,872 B1 | 1/2002 | Termin et al. |
| 6,336,938 B1 | 1/2002 | Kavteladze et al. |
| 6,338,730 B1 | 1/2002 | Bonutti et al. |
| 6,338,740 B1 | 1/2002 | Carpentier |
| 6,340,366 B2 | 1/2002 | Wijay |
| 6,342,067 B1 | 1/2002 | Mathis et al. |
| 6,342,070 B1 | 1/2002 | Nguyen-Thien-Nhon |
| 6,346,074 B1 | 2/2002 | Roth |
| 6,348,065 B1 | 2/2002 | Brown et al. |
| 6,352,554 B2 | 3/2002 | De Paulis |
| 6,355,052 B1 | 3/2002 | Neuss et al. |
| 6,355,056 B1 | 3/2002 | Pinheiro |
| 6,355,070 B1 | 3/2002 | Andersen et al. |
| 6,358,228 B1 | 3/2002 | Tubman et al. |
| 6,358,277 B1 | 3/2002 | Duran |
| 6,358,284 B1 | 3/2002 | Fearnot et al. |
| 6,368,338 B1 | 4/2002 | Konya et al. |
| 6,371,961 B1 | 4/2002 | Osborne et al. |
| 6,371,983 B1 | 4/2002 | Lane |
| 6,375,679 B1 | 4/2002 | Martyn et al. |
| 6,375,989 B1 | 4/2002 | Badylak et al. |
| 6,379,365 B1 | 4/2002 | Diaz |
| 6,379,710 B1 | 4/2002 | Badylak |
| 6,383,216 B1 | 5/2002 | Kavteladze et al. |
| 6,383,832 B1 | 5/2002 | Stone |
| 6,395,018 B1 | 5/2002 | Castaneda |
| 6,409,752 B1 | 6/2002 | Boatman et al. |
| 6,415,631 B1 | 7/2002 | Weston et al. |
| 6,416,542 B1 | 7/2002 | Marcade et al. |
| 6,425,914 B1 | 7/2002 | Wallace et al. |
| 6,425,916 B1 | 7/2002 | Garrison |
| 6,428,570 B1 | 8/2002 | Globerman |
| 6,440,163 B1 | 8/2002 | Swanson et al. |
| 6,440,164 B1 | 8/2002 | DiMatteo et al. |
| 6,444,229 B2 | 9/2002 | Voytik-Harbin et al. |
| 6,451,052 B1 | 9/2002 | Burmeister et al. |
| 6,458,137 B1 | 10/2002 | Klint |
| 6,458,153 B1 | 10/2002 | Bailey et al. |
| 6,461,382 B1 | 10/2002 | Cao |
| 6,464,720 B2 | 10/2002 | Boatman |
| 6,471,718 B1 | 10/2002 | Staehle |
| 6,478,819 B2 | 11/2002 | Moe |
| 6,482,228 B1 | 11/2002 | Norred |
| 6,485,500 B1 | 11/2002 | Kokish et al. |
| 6,485,510 B1 | 11/2002 | Camrud et al. |
| 6,488,702 B1 | 12/2002 | Besselink |
| 6,494,909 B2 | 12/2002 | Greenhalgh |
| 6,503,272 B2 | 1/2003 | Duerig et al. |
| 6,508,824 B1 | 1/2003 | Flaherty et al. |
| 6,508,833 B2 | 1/2003 | Pavcnik |
| 6,508,966 B1 | 1/2003 | Castro et al. |
| 6,514,063 B2 | 2/2003 | Acciai et al. |
| 6,524,336 B1 | 2/2003 | Papazoglou et al. |
| 6,527,800 B1 | 3/2003 | McGuckin, Jr. et al. |
| 6,530,951 B1 | 3/2003 | Bates et al. |
| 6,533,807 B2 | 3/2003 | Wolinsky et al. |
| 6,544,291 B2 | 4/2003 | Taylor |
| 6,547,815 B2 | 4/2003 | Myers et al. |
| 6,553,801 B2 | 4/2003 | Chen |
| 6,558,415 B2 | 5/2003 | Thompson |
| 6,558,418 B2 | 5/2003 | Carpentier et al. |
| 6,558,429 B2 | 5/2003 | Taylor |
| 6,562,065 B1 | 5/2003 | Shanley |
| 6,565,597 B1 | 5/2003 | Fearnot et al. |
| 6,565,600 B2 | 5/2003 | Hojeibane |
| 6,572,650 B1 | 6/2003 | Abraham et al. |
| 6,579,221 B1 | 6/2003 | Peterson |
| 6,579,307 B2 | 6/2003 | Sarac |
| 6,579,311 B1 | 6/2003 | Makower |
| 6,579,538 B1 | 6/2003 | Spievack |
| 6,580,568 B2 | 6/2003 | Ozaki |
| 6,582,462 B1 | 6/2003 | Andersen et al. |
| 6,585,761 B2 | 7/2003 | Taheri |
| 6,589,230 B2 | 7/2003 | Gia et al. |
| 6,594,880 B2 | 7/2003 | Elsberry |
| 6,596,021 B1 | 7/2003 | Lootz |
| 6,598,307 B2 | 7/2003 | Love et al. |
| 6,599,275 B1 | 7/2003 | Fischer, Jr. |
| 6,602,241 B2 | 8/2003 | Makower et al. |
| 6,602,286 B1 | 8/2003 | Strecker |
| 6,605,049 B1 | 8/2003 | Wagner et al. |
| 6,613,002 B1 | 9/2003 | Clark et al. |
| 6,613,086 B1 | 9/2003 | Moe et al. |
| 6,616,680 B1 | 9/2003 | Thielen |
| 6,623,506 B2 | 9/2003 | McGuckin, Jr. et al. |
| 6,623,508 B2 | 9/2003 | Shaw et al. |
| 6,632,196 B1 | 10/2003 | Houser |
| 6,638,300 B1 | 10/2003 | Frantzen |
| 6,640,412 B2 | 11/2003 | Iancea |
| 6,656,206 B2 | 12/2003 | Corcoran et al. |
| 6,656,216 B1 | 12/2003 | Hossainy et al. |
| 6,663,661 B2 | 12/2003 | Boneau |
| 6,666,885 B2 | 12/2003 | Moe |
| 6,666,886 B1 | 12/2003 | Tranquillo et al. |
| 6,669,724 B2 | 12/2003 | Park et al. |
| 6,673,100 B2 | 1/2004 | Diaz et al. |
| 6,676,694 B1 | 1/2004 | Weiss |
| 6,676,698 B2 | 1/2004 | McGuckin, Jr. et al. |
| 6,678,962 B1 | 1/2004 | Love et al. |
| 6,685,739 B2 | 2/2004 | DiMatteo et al. |
| 6,689,123 B2 | 2/2004 | Pinchasik |
| 6,692,458 B2 | 2/2004 | Forman et al. |
| 6,706,026 B1 | 3/2004 | Goldstein et al. |
| 6,716,241 B2 | 4/2004 | Wilder et al. |
| 6,720,402 B2 | 4/2004 | Langer et al. |
| 6,726,715 B2 | 4/2004 | Sutherland |
| 6,730,064 B2 | 5/2004 | Ragheb et al. |
| 6,730,117 B1 | 5/2004 | Tseng et al. |
| 6,730,118 B2 | 5/2004 | Spenser et al. |
| 6,733,525 B2 | 5/2004 | Yang et al. |
| 6,746,489 B2 | 6/2004 | Dua et al. |
| 6,749,622 B2 | 6/2004 | McGuckin, Jr. et al. |
| 6,752,826 B2 | 6/2004 | Holloway et al. |
| 6,752,828 B2 | 6/2004 | Thornton |
| 6,761,735 B2 | 7/2004 | Eberhardt et al. |
| 6,767,362 B2 | 7/2004 | Schreck |
| 6,783,499 B2 | 8/2004 | Schwartz |
| 6,786,922 B2 | 9/2004 | Schaeffer |
| 6,790,214 B2 | 9/2004 | Kraemer et al. |
| 6,790,218 B2 | 9/2004 | Jayaraman |
| 6,790,237 B2 | 9/2004 | Stinson |
| 6,821,292 B2 | 11/2004 | Pazienza et al. |
| 6,823,576 B2 | 11/2004 | Austin |
| 6,830,584 B1 | 12/2004 | Seguin |
| 6,843,802 B1 | 1/2005 | Villalobos et al. |
| 6,859,986 B2 | 3/2005 | Jackson |
| 6,878,162 B2 | 4/2005 | Bales et al. |
| 6,896,690 B1 | 5/2005 | Lambrecht |
| 6,908,481 B2 | 6/2005 | Cribier |
| 6,911,037 B2 | 6/2005 | Gainor et al. |
| 6,915,560 B2 | 7/2005 | Austin |
| 6,918,929 B2 | 7/2005 | Udipi et al. |
| 6,921,378 B2 | 7/2005 | O'Keefe et al. |
| 6,932,829 B2 | 8/2005 | Majercak |
| 6,939,377 B2 | 9/2005 | Jayaraman et al. |
| 6,945,978 B1 | 9/2005 | Hyde |

(56) References Cited

U.S. PATENT DOCUMENTS

| | | |
|---|---|---|
| 6,945,989 B1 | 9/2005 | Betelia et al. |
| 6,949,113 B2 | 9/2005 | Van Tassel et al. |
| 6,949,116 B2 | 9/2005 | Solymar et al. |
| 6,953,332 B1 | 10/2005 | Kurk et al. |
| 6,958,076 B2 | 10/2005 | Acosta |
| 6,960,220 B2 | 11/2005 | Marino et al. |
| 6,962,603 B1 | 11/2005 | Brown et al. |
| 6,974,474 B2 | 12/2005 | Pavcnik et al. |
| 6,976,995 B2 | 12/2005 | Mathis et al. |
| 6,994,092 B2 | 2/2006 | Van der Burg et al. |
| 6,994,717 B2 | 2/2006 | Konya et al. |
| 7,011,671 B2 | 3/2006 | Welch |
| 7,018,403 B1 | 3/2006 | Pienknagura |
| 7,018,404 B2 | 3/2006 | Holmberg et al. |
| 7,018,406 B2 | 3/2006 | Seguin |
| 7,018,407 B1 | 3/2006 | Wright et al. |
| 7,025,777 B2 | 4/2006 | Moore |
| 7,025,780 B2 | 4/2006 | Gabbay |
| 7,025,923 B2 | 4/2006 | Harhen et al. |
| 7,029,493 B2 | 4/2006 | Majercak et al. |
| 7,044,966 B2 | 5/2006 | Svanidze et al. |
| 7,060,088 B1 | 6/2006 | Fischell et al. |
| 7,070,616 B2 | 7/2006 | Majercak et al. |
| 7,081,131 B2 | 7/2006 | Thornton |
| 7,087,089 B2 * | 8/2006 | Patel .................. A61L 26/0033 424/572 |
| 7,101,381 B2 | 9/2006 | Ford et al. |
| 7,101,395 B2 | 9/2006 | Tremulis et al. |
| 7,101,396 B2 | 9/2006 | Svanidze et al. |
| 7,118,600 B2 | 10/2006 | Dua et al. |
| 7,125,418 B2 | 10/2006 | Duran et al. |
| 7,128,073 B1 | 10/2006 | van der Burg et al. |
| 7,128,756 B2 | 10/2006 | Lowe et al. |
| 7,128,757 B2 | 10/2006 | Osborne et al. |
| 7,128,759 B2 | 10/2006 | Osborne et al. |
| 7,144,410 B2 | 12/2006 | Marino et al. |
| 7,147,661 B2 | 12/2006 | Chobotov et al. |
| 7,153,324 B2 | 12/2006 | Case et al. |
| 7,160,320 B2 | 1/2007 | Duran |
| 7,163,556 B2 | 1/2007 | Xie et al. |
| 7,172,625 B2 | 2/2007 | Shu et al. |
| 7,179,270 B2 | 2/2007 | Makower |
| 7,182,779 B2 | 2/2007 | Acosta et al. |
| 7,186,789 B2 | 3/2007 | Hossainy et al. |
| 7,195,641 B2 | 3/2007 | Palmaz et al. |
| 7,232,462 B2 | 6/2007 | Schaeffer |
| 7,247,167 B2 | 7/2007 | Gabbay |
| 7,258,697 B1 | 8/2007 | Cox et al. |
| 7,261,732 B2 | 8/2007 | Justino |
| 7,273,492 B2 | 9/2007 | Cheng et al. |
| 7,288,105 B2 | 10/2007 | Oman et al. |
| 7,303,571 B2 | 12/2007 | Makower et al. |
| 7,323,010 B2 | 1/2008 | Verona et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,354,455 B2 | 4/2008 | Stinson |
| 7,361,189 B2 | 4/2008 | Case et al. |
| 7,364,587 B2 | 4/2008 | Dong et al. |
| 7,377,938 B2 | 5/2008 | Sarac et al. |
| 7,381,219 B2 | 6/2008 | Salahieh et al. |
| 7,399,315 B2 | 7/2008 | Iobbi |
| 7,402,171 B2 | 7/2008 | Osborne |
| 7,435,257 B2 | 10/2008 | Lashinski et al. |
| 7,445,630 B2 | 11/2008 | Lashinski et al. |
| 7,445,631 B2 | 11/2008 | Salahieh et al. |
| 7,452,371 B2 | 11/2008 | Pavcnik et al. |
| 7,491,942 B2 | 2/2009 | Black et al. |
| 7,503,928 B2 | 3/2009 | Case et al. |
| 7,520,894 B2 | 4/2009 | Pavcnik et al. |
| 7,524,331 B2 | 4/2009 | Birdsall |
| 7,524,332 B2 | 4/2009 | Osborne et al. |
| 7,534,259 B2 | 5/2009 | Lashinski et al. |
| 7,544,205 B2 | 6/2009 | Flagle et al. |
| 7,544,207 B2 | 6/2009 | Osborne et al. |
| 7,547,322 B2 | 6/2009 | Sarac et al. |
| 7,556,645 B2 | 7/2009 | Lashinski et al. |
| 7,563,276 B2 | 7/2009 | Osborne et al. |
| 7,563,277 B2 | 7/2009 | Case et al. |
| 7,566,336 B2 | 7/2009 | Corcoran et al. |
| 7,569,071 B2 | 8/2009 | Haverkost et al. |
| 7,582,110 B2 | 9/2009 | Case et al. |
| 7,585,321 B2 | 9/2009 | Cribier |
| 7,594,927 B2 | 9/2009 | Majercak et al. |
| 7,604,661 B2 | 10/2009 | Pavcnik et al. |
| 7,618,447 B2 | 11/2009 | Case et al. |
| 7,625,395 B2 | 12/2009 | Case et al. |
| 7,625,399 B2 | 12/2009 | Case et al. |
| 7,628,803 B2 | 12/2009 | Pavcnik et al. |
| 7,628,804 B2 | 12/2009 | Flagle et al. |
| 7,637,937 B2 | 12/2009 | Case et al. |
| 7,641,686 B2 | 1/2010 | Lashinski et al. |
| 7,648,527 B2 | 1/2010 | Agnew |
| 7,653,455 B2 | 1/2010 | Cinader, Jr. |
| 7,655,288 B2 | 2/2010 | Bauman et al. |
| 7,655,584 B2 | 2/2010 | Biran et al. |
| 7,658,759 B2 | 2/2010 | Case et al. |
| 7,658,762 B2 | 2/2010 | Lashinski et al. |
| 7,659,219 B2 | 2/2010 | Biran et al. |
| 7,670,366 B2 | 3/2010 | Case et al. |
| 7,678,144 B2 | 3/2010 | Bailey et al. |
| 7,686,844 B2 | 3/2010 | Case et al. |
| 7,736,385 B2 | 6/2010 | Agnew |
| 7,739,971 B2 | 6/2010 | Chambers et al. |
| 7,745,532 B2 | 6/2010 | Ruberti et al. |
| 7,806,921 B2 | 10/2010 | Hoffman |
| 7,815,923 B2 | 10/2010 | Johnson et al. |
| 7,819,836 B2 | 10/2010 | Levine et al. |
| 7,846,199 B2 | 12/2010 | Paul, Jr. et al. |
| 7,846,203 B2 | 12/2010 | Cribier |
| 7,850,510 B2 | 12/2010 | Farnsworth et al. |
| 7,854,759 B2 | 12/2010 | Shirley |
| 7,861,570 B2 | 1/2011 | Thomas |
| 7,871,430 B2 | 1/2011 | Pavcnik et al. |
| 7,918,882 B2 | 4/2011 | Pavcnik et al. |
| 7,935,144 B2 | 5/2011 | Lashinski et al. |
| 7,942,887 B2 | 5/2011 | Kraemer et al. |
| 7,955,375 B2 | 6/2011 | Agnew |
| 7,955,376 B2 | 6/2011 | Osborne et al. |
| 7,955,377 B2 | 6/2011 | Melsheimer |
| 7,964,206 B2 | 6/2011 | Suokas et al. |
| 7,979,150 B2 | 7/2011 | Lin et al. |
| 7,993,410 B2 | 8/2011 | Shin et al. |
| 8,012,201 B2 | 9/2011 | Lashinski et al. |
| 8,038,708 B2 | 10/2011 | Case et al. |
| 8,038,710 B2 | 10/2011 | Fearnot et al. |
| 8,048,500 B2 | 11/2011 | Drumheller et al. |
| 8,048,503 B2 | 11/2011 | Farnsworth et al. |
| 8,057,532 B2 | 11/2011 | Hoffman |
| 8,057,540 B2 | 11/2011 | Letac et al. |
| 8,092,522 B2 | 1/2012 | Paul, Jr. et al. |
| 8,100,962 B2 | 1/2012 | Agnew et al. |
| 8,109,990 B2 | 2/2012 | Paul et al. |
| 8,118,877 B2 | 2/2012 | Brauker et al. |
| 8,128,686 B2 | 3/2012 | Paul, Jr. et al. |
| 8,129,477 B1 | 3/2012 | Zhang et al. |
| 8,133,213 B2 | 3/2012 | Lashinski et al. |
| 8,133,500 B2 | 3/2012 | Ringeisen et al. |
| 8,157,810 B2 | 4/2012 | Case et al. |
| 8,157,857 B2 | 4/2012 | Case et al. |
| 8,197,534 B2 | 6/2012 | Osborne et al. |
| 8,211,165 B1 | 7/2012 | McIntosh et al. |
| 8,221,492 B2 | 7/2012 | Case et al. |
| 8,252,043 B2 | 8/2012 | Case et al. |
| 8,257,429 B2 | 9/2012 | Pavcnik |
| 8,273,117 B2 | 9/2012 | Palumbo et al. |
| 8,276,533 B2 | 10/2012 | Chambers et al. |
| 8,292,938 B2 | 10/2012 | Case |
| 8,303,648 B2 | 11/2012 | Grewe et al. |
| 8,303,649 B2 | 11/2012 | Agnew et al. |
| 8,308,796 B2 | 11/2012 | Lashinski et al. |
| 8,313,526 B2 | 11/2012 | Hoffman et al. |
| 8,317,853 B2 | 11/2012 | Agnew |
| 8,323,332 B2 | 12/2012 | Agnew |

(56) References Cited

U.S. PATENT DOCUMENTS

| | | |
|---|---|---|
| 8,337,545 B2 | 12/2012 | Osborne |
| 8,351,126 B2 | 1/2013 | Peng |
| 8,366,741 B2 | 2/2013 | Chin et al. |
| 8,366,743 B2 | 2/2013 | Zeng |
| 8,377,118 B2 | 2/2013 | Lashinski et al. |
| 8,403,977 B2 | 3/2013 | Case et al. |
| 8,403,979 B2 | 3/2013 | Paul, Jr. |
| 8,470,020 B2 | 6/2013 | Schaeffer et al. |
| 8,475,512 B2 | 7/2013 | Hunt |
| 8,475,516 B2 | 7/2013 | Paul et al. |
| 8,506,621 B2 | 8/2013 | Agnew et al. |
| 8,556,881 B2 | 10/2013 | Lashinski et al. |
| 8,568,477 B2 | 10/2013 | Lashinski et al. |
| 8,617,205 B2 | 12/2013 | Pavcnik et al. |
| 8,652,197 B2 | 2/2014 | Paul et al. |
| 8,663,320 B2 | 3/2014 | Chambers et al. |
| 8,679,175 B2 | 3/2014 | Paul, Jr. et al. |
| 8,702,746 B2 | 4/2014 | Tekulve et al. |
| 8,771,338 B2 | 7/2014 | Schaeffer et al. |
| 2001/0001128 A1 | 5/2001 | Holman et al. |
| 2001/0004707 A1 | 6/2001 | Dereume et al. |
| 2001/0007956 A1 | 7/2001 | Letac et al. |
| 2001/0011187 A1 | 8/2001 | Pavcnik et al. |
| 2001/0016770 A1 | 8/2001 | Allen et al. |
| 2001/0018610 A1 | 8/2001 | Limon |
| 2001/0020189 A1 | 9/2001 | Taylor |
| 2001/0020190 A1 | 9/2001 | Taylor |
| 2001/0021872 A1 | 9/2001 | Bailey et al. |
| 2001/0025197 A1 | 9/2001 | Shu et al. |
| 2001/0034537 A1 | 10/2001 | Shaw et al. |
| 2001/0037129 A1 | 11/2001 | Thill |
| 2001/0039450 A1 | 11/2001 | Pavcnik et al. |
| 2001/0041930 A1 | 11/2001 | Globerman et al. |
| 2001/0044648 A1 | 11/2001 | Wolinsky et al. |
| 2001/0049553 A1 | 12/2001 | De Paulis et al. |
| 2002/0002400 A1 | 1/2002 | Drasler et al. |
| 2002/0019665 A1 | 2/2002 | Dehdashtian et al. |
| 2002/0029994 A1 | 3/2002 | Schon |
| 2002/0032414 A1 | 3/2002 | Ragheb et al. |
| 2002/0038128 A1 | 3/2002 | Turovkiy et al. |
| 2002/0052642 A1 | 5/2002 | Cox et al. |
| 2002/0052651 A1 | 5/2002 | Myers et al. |
| 2002/0055772 A1 | 5/2002 | McGuckin, Jr. et al. |
| 2002/0065552 A1 | 5/2002 | Jayaraman et al. |
| 2002/0065554 A1 | 5/2002 | Streeter |
| 2002/0068866 A1 | 6/2002 | Zikorus |
| 2002/0072794 A1 | 6/2002 | Gabbay |
| 2002/0099439 A1 | 7/2002 | Schwartz et al. |
| 2002/0111339 A1 | 8/2002 | Klausener et al. |
| 2002/0111647 A1 | 8/2002 | Khairkhahan et al. |
| 2002/0115559 A1 | 8/2002 | Batchelor et al. |
| 2002/0120338 A1 | 8/2002 | Boyer et al. |
| 2002/0123786 A1 | 9/2002 | Gittings |
| 2002/0123790 A1 | 9/2002 | White et al. |
| 2002/0123800 A1 | 9/2002 | Taheri |
| 2002/0123802 A1 | 9/2002 | Snyders |
| 2002/0129820 A1 | 9/2002 | Ryan et al. |
| 2002/0138131 A1 | 9/2002 | Solovay et al. |
| 2002/0138135 A1 | 9/2002 | Duerig et al. |
| 2002/0169475 A1 | 11/2002 | Gainor et al. |
| 2002/0173843 A1 | 11/2002 | Peredo et al. |
| 2002/0177890 A1 | 11/2002 | Lenker |
| 2002/0177894 A1 | 11/2002 | Acosta et al. |
| 2002/0177899 A1 | 11/2002 | Eum |
| 2002/0179098 A1 | 12/2002 | Makower |
| 2002/0183787 A1 | 12/2002 | Wahr et al. |
| 2002/0187288 A1 | 12/2002 | Lim et al. |
| 2002/0193871 A1 | 12/2002 | Beyersdorf et al. |
| 2002/0198563 A1 | 12/2002 | Gainor et al. |
| 2003/0014104 A1 | 1/2003 | Cribier |
| 2003/0014126 A1 | 1/2003 | Patel et al. |
| 2003/0018968 A1 | 1/2003 | Avnet |
| 2003/0023302 A1 | 1/2003 | Moe et al. |
| 2003/0023303 A1 | 1/2003 | Palmaz et al. |
| 2003/0028213 A1 | 2/2003 | Thill et al. |
| 2003/0028233 A1 | 2/2003 | Vardi et al. |
| 2003/0033009 A1 | 2/2003 | Gabbay |
| 2003/0036794 A1 | 2/2003 | Ragheb et al. |
| 2003/0040792 A1 | 2/2003 | Gabbay |
| 2003/0040808 A1 | 2/2003 | Stack et al. |
| 2003/0055483 A1 | 3/2003 | Gumm |
| 2003/0055492 A1 | 3/2003 | Shaolian et al. |
| 2003/0055496 A1 | 3/2003 | Cai et al. |
| 2003/0069646 A1 | 4/2003 | Stinson |
| 2003/0083730 A1 | 5/2003 | Stinson |
| 2003/0083741 A1 | 5/2003 | Woo et al. |
| 2003/0093071 A1 | 5/2003 | Hauck et al. |
| 2003/0093108 A1 | 5/2003 | Avellanet et al. |
| 2003/0093144 A1 | 5/2003 | Jang |
| 2003/0097172 A1 | 5/2003 | Shalev et al. |
| 2003/0109922 A1 | 6/2003 | Peterson et al. |
| 2003/0114913 A1 | 6/2003 | Spenser et al. |
| 2003/0114919 A1 | 6/2003 | McQuiston et al. |
| 2003/0120263 A1 | 6/2003 | Ouriel et al. |
| 2003/0125790 A1 | 7/2003 | Fastovsky et al. |
| 2003/0125791 A1 | 7/2003 | Sequin et al. |
| 2003/0125795 A1 | 7/2003 | Pavcnik et al. |
| 2003/0129751 A1* | 7/2003 | Grikscheit ......... A61L 27/3641 623/23.71 |
| 2003/0130713 A1 | 7/2003 | Stewart et al. |
| 2003/0130726 A1 | 7/2003 | Thorpe et al. |
| 2003/0135266 A1 | 7/2003 | Chew et al. |
| 2003/0139805 A1 | 7/2003 | Holmberg et al. |
| 2003/0139819 A1 | 7/2003 | Beer et al. |
| 2003/0144670 A1 | 7/2003 | Pavcnik et al. |
| 2003/0144694 A1 | 7/2003 | Chanduszko et al. |
| 2003/0149471 A1 | 8/2003 | Briana et al. |
| 2003/0153972 A1 | 8/2003 | Helmus |
| 2003/0153974 A1 | 8/2003 | Spenser et al. |
| 2003/0163190 A1 | 8/2003 | LaFont et al. |
| 2003/0171824 A1 | 9/2003 | Abraham et al. |
| 2003/0176911 A1 | 9/2003 | Iancea et al. |
| 2003/0176912 A1 | 9/2003 | Chuter et al. |
| 2003/0176914 A1 | 9/2003 | Rabkin et al. |
| 2003/0181968 A1 | 9/2003 | Xie et al. |
| 2003/0181973 A1 | 9/2003 | Sahota |
| 2003/0181974 A1 | 9/2003 | Xie et al. |
| 2003/0187500 A1 | 10/2003 | Jansen et al. |
| 2003/0191495 A1 | 10/2003 | Ryan et al. |
| 2003/0191525 A1 | 10/2003 | Thornton |
| 2003/0195618 A1 | 10/2003 | Abraham et al. |
| 2003/0199747 A1 | 10/2003 | Michlitsch |
| 2003/0199767 A1 | 10/2003 | Cespedes |
| 2003/0199768 A1 | 10/2003 | Cespedes |
| 2003/0206860 A1 | 11/2003 | Bleyer et al. |
| 2003/0208224 A1 | 11/2003 | Broome |
| 2003/0208254 A1 | 11/2003 | Shortt |
| 2003/0208261 A1 | 11/2003 | Thorpe et al. |
| 2003/0209835 A1 | 11/2003 | Chun et al. |
| 2003/0212431 A1 | 11/2003 | Brady et al. |
| 2003/0220683 A1 | 11/2003 | Minasian et al. |
| 2003/0225445 A1 | 12/2003 | Derus |
| 2003/0225446 A1 | 12/2003 | Hartley |
| 2003/0225449 A1 | 12/2003 | Denison |
| 2003/0236443 A1 | 12/2003 | Cespedes |
| 2003/0236568 A1 | 12/2003 | Hojeibane et al. |
| 2004/0006380 A1 | 1/2004 | Buck et al. |
| 2004/0015230 A1 | 1/2004 | Moll |
| 2004/0015232 A1 | 1/2004 | Salazar |
| 2004/0019374 A1 | 1/2004 | Hojeibane et al. |
| 2004/0024444 A1 | 2/2004 | Moore |
| 2004/0024447 A1 | 2/2004 | Haverich |
| 2004/0024452 A1 | 2/2004 | Kruse et al. |
| 2004/0029993 A1 | 2/2004 | Klee et al. |
| 2004/0034409 A1 | 2/2004 | Heublein et al. |
| 2004/0044401 A1 | 3/2004 | Bales et al. |
| 2004/0044407 A1 | 3/2004 | Verona |
| 2004/0047909 A1 | 3/2004 | Ragheb |
| 2004/0049262 A1 | 3/2004 | Obermiller et al. |
| 2004/0049266 A1 | 3/2004 | Anduiza et al. |
| 2004/0059411 A1 | 3/2004 | Strecker |
| 2004/0064067 A1 | 4/2004 | Ward |
| 2004/0073155 A1 | 4/2004 | Laufer et al. |
| 2004/0073230 A1 | 4/2004 | Mulholland et al. |

(56) References Cited

U.S. PATENT DOCUMENTS

| | | |
|---|---|---|
| 2004/0073238 A1 | 4/2004 | Makower |
| 2004/0073242 A1 | 4/2004 | Chanduszko |
| 2004/0073297 A1 | 4/2004 | Rohde et al. |
| 2004/0078053 A1 | 4/2004 | Berg et al. |
| 2004/0093017 A1 | 5/2004 | Chanduszko |
| 2004/0093061 A1 | 5/2004 | Acosta et al. |
| 2004/0093070 A1 | 5/2004 | Hojeibane et al. |
| 2004/0093073 A1 | 5/2004 | Lowe et al. |
| 2004/0098030 A1 | 5/2004 | Makower et al. |
| 2004/0098079 A1 | 5/2004 | Hartley |
| 2004/0098098 A1 | 5/2004 | McGuckin et al. |
| 2004/0102806 A1 | 5/2004 | Broome et al. |
| 2004/0102834 A1 | 5/2004 | Nakano et al. |
| 2004/0102855 A1 | 5/2004 | Shank |
| 2004/0106985 A1 | 6/2004 | Jang |
| 2004/0111145 A1 | 6/2004 | Serino et al. |
| 2004/0117004 A1 | 6/2004 | Osborne et al. |
| 2004/0117010 A1 | 6/2004 | Houston et al. |
| 2004/0117031 A1 | 6/2004 | Stack et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0137042 A1 | 7/2004 | Hiles et al. |
| 2004/0138737 A1 | 7/2004 | Davidson et al. |
| 2004/0143277 A1 | 7/2004 | Marino et al. |
| 2004/0143291 A1 | 7/2004 | Corcoran et al. |
| 2004/0143292 A1 | 7/2004 | Marino et al. |
| 2004/0143293 A1 | 7/2004 | Marino et al. |
| 2004/0143294 A1 | 7/2004 | Corcoran et al. |
| 2004/0148000 A1 | 7/2004 | Bilge |
| 2004/0158331 A1 | 8/2004 | Stack et al. |
| 2004/0166169 A1 | 8/2004 | Malaviya et al. |
| 2004/0167566 A1 | 8/2004 | Beulke et al. |
| 2004/0167619 A1 | 8/2004 | Case et al. |
| 2004/0080352 A1 | 9/2004 | Bleyer |
| 2004/0172141 A1 | 9/2004 | Stack et al. |
| 2004/0176799 A1 | 9/2004 | Chanduszko et al. |
| 2004/0180042 A1 | 9/2004 | Cook et al. |
| 2004/0186558 A1 | 9/2004 | Pavcnik |
| 2004/0210301 A1 | 10/2004 | Obermiller |
| 2004/0210306 A1 | 10/2004 | Quijano et al. |
| 2004/0213756 A1 | 10/2004 | Michal et al. |
| 2004/0215333 A1 | 10/2004 | Duran et al. |
| 2004/0220610 A1 | 11/2004 | Kreidler et al. |
| 2004/0224868 A1 | 11/2004 | Meyerhoff et al. |
| 2004/0225344 A1 | 11/2004 | Hoffa et al. |
| 2004/0225348 A1 | 11/2004 | Case et al. |
| 2004/0225352 A1 | 11/2004 | Osborne et al. |
| 2004/0225356 A1 | 11/2004 | Frater |
| 2004/0230222 A1 | 11/2004 | Van der Burg et al. |
| 2004/0230287 A1 | 11/2004 | Hartley |
| 2004/0243216 A1 | 12/2004 | Gregorich |
| 2004/0243218 A1 | 12/2004 | Schaeffer |
| 2004/0243219 A1 | 12/2004 | Fischer et al. |
| 2004/0243222 A1 | 12/2004 | Osborne et al. |
| 2004/0249439 A1 | 12/2004 | Richter et al. |
| 2004/0254640 A1 | 12/2004 | Sutherland et al. |
| 2004/0260229 A1 | 12/2004 | Meir |
| 2004/0260328 A1 | 12/2004 | Zvuloni et al. |
| 2004/0260340 A1 | 12/2004 | Jacobs et al. |
| 2004/0260389 A1 | 12/2004 | Case |
| 2004/0260390 A1 | 12/2004 | Sarac et al. |
| 2004/0260393 A1 | 12/2004 | Randert et al. |
| 2004/0267191 A1 | 12/2004 | Gifford, III et al. |
| 2004/0267306 A1 | 12/2004 | Blaeser et al. |
| 2005/0004659 A1 | 1/2005 | Von Oepen et al. |
| 2005/0010248 A1 | 1/2005 | Lafontaine |
| 2005/0010285 A1 | 1/2005 | Lambrecht et al. |
| 2005/0010287 A1 | 1/2005 | Macoviak et al. |
| 2005/0033398 A1 | 2/2005 | Seguin |
| 2005/0034735 A1 | 2/2005 | Deem et al. |
| 2005/0038501 A1 | 2/2005 | Moore, Jr. et al. |
| 2005/0043708 A1 | 2/2005 | Gleeson et al. |
| 2005/0043759 A1 | 2/2005 | Chanduszko |
| 2005/0049634 A1 | 3/2005 | Chopra |
| 2005/0055079 A1 | 3/2005 | Duran et al. |
| 2005/0059923 A1 | 3/2005 | Gamboa |
| 2005/0060024 A1 | 3/2005 | Lee et al. |
| 2005/0065547 A1 | 3/2005 | Marino et al. |
| 2005/0065548 A1 | 3/2005 | Marino et al. |
| 2005/0065614 A1 | 3/2005 | Stinson |
| 2005/0070794 A1 | 3/2005 | Deal et al. |
| 2005/0070821 A1 | 3/2005 | Deal et al. |
| 2005/0075713 A1 | 4/2005 | Biancucci et al. |
| 2005/0075725 A1 | 4/2005 | Rowe |
| 2005/0075726 A1 | 4/2005 | Svanidze et al. |
| 2005/0075728 A1 | 4/2005 | Nguyen et al. |
| 2005/0085843 A1 | 4/2005 | Opolski et al. |
| 2005/0085900 A1 | 4/2005 | Case et al. |
| 2005/0096736 A1 | 4/2005 | Case |
| 2005/0092335 A1 | 5/2005 | Bertrand |
| 2005/0096734 A1 | 5/2005 | Majercak et al. |
| 2005/0096735 A1 | 5/2005 | Hojeibane et al. |
| 2005/0113686 A1 | 5/2005 | Peckham et al. |
| 2005/0113910 A1 | 5/2005 | Paniagua |
| 2005/0125032 A1 | 6/2005 | Whisenant et al. |
| 2005/0125050 A1 | 6/2005 | Carter |
| 2005/0137676 A1 | 6/2005 | Richardson et al. |
| 2005/0137681 A1 | 6/2005 | Shoemaker et al. |
| 2005/0143801 A1 | 6/2005 | Aboul-Hosn |
| 2005/0143806 A1 | 6/2005 | Phillips |
| 2005/0143807 A1 | 6/2005 | Pavcnik |
| 2005/0149459 A1 | 7/2005 | Andreas et al. |
| 2005/0154405 A1 | 7/2005 | Kraemer et al. |
| 2005/0163818 A1 | 7/2005 | Sung et al. |
| 2005/0171592 A1 | 8/2005 | Majercak |
| 2005/0182483 A1 | 8/2005 | Osborne et al. |
| 2005/0187565 A1 | 8/2005 | Baker et al. |
| 2005/0187614 A1 | 8/2005 | Agnew |
| 2005/0191496 A1 | 9/2005 | Maschke |
| 2005/0192626 A1 | 9/2005 | Widomski et al. |
| 2005/0192627 A1 | 9/2005 | Whisenant et al. |
| 2005/0203568 A1 | 9/2005 | Burg et al. |
| 2005/0216077 A1 | 9/2005 | Mathis et al. |
| 2005/0222661 A1 | 10/2005 | Case et al. |
| 2005/0228434 A1 | 10/2005 | Amplatz et al. |
| 2005/0228479 A1 | 10/2005 | Pavcnik et al. |
| 2005/0228486 A1 | 10/2005 | Case |
| 2005/0228495 A1 | 10/2005 | Macoviak |
| 2005/0228505 A1 | 10/2005 | Cornet et al. |
| 2005/0234509 A1 | 10/2005 | Widomski et al. |
| 2005/0234541 A1 | 10/2005 | Hunt et al. |
| 2005/0234546 A1 | 10/2005 | Nugent et al. |
| 2005/0240200 A1 | 10/2005 | Bergheim |
| 2005/0240255 A1 | 10/2005 | Schaeffer |
| 2005/0249772 A1 | 11/2005 | Malaviya et al. |
| 2005/0251201 A1 | 11/2005 | Roue et al. |
| 2005/0256532 A1 | 11/2005 | Nayak et al. |
| 2005/0261759 A1 | 11/2005 | Lambrecht et al. |
| 2005/0267524 A1 | 12/2005 | Chanduszko |
| 2005/0267526 A1 | 12/2005 | Wahr et al. |
| 2005/0267560 A1 | 12/2005 | Bates |
| 2005/0267573 A9 | 12/2005 | Macoviak et al. |
| 2005/0273124 A1 | 12/2005 | Chanduszko |
| 2005/0273153 A1 | 12/2005 | Clerc et al. |
| 2005/0273160 A1 | 12/2005 | Lashinski et al. |
| 2005/0283187 A1 | 12/2005 | Longson |
| 2005/0288706 A1 | 12/2005 | Widomski et al. |
| 2005/0288786 A1 | 12/2005 | Chanduszko |
| 2006/0004433 A1 | 1/2006 | Greenberg |
| 2006/0004436 A1 | 1/2006 | Amarant et al. |
| 2006/0009800 A1 | 1/2006 | Christianson et al. |
| 2006/0015178 A1 | 1/2006 | Moaddeb et al. |
| 2006/0020332 A1 | 1/2006 | Lashinski et al. |
| 2006/0020334 A1 | 1/2006 | Lashinski et al. |
| 2006/0025844 A1 | 2/2006 | Majercak et al. |
| 2006/0030923 A1 | 2/2006 | Gunderson |
| 2006/0036282 A1 | 2/2006 | Wahr et al. |
| 2006/0041302 A1 | 2/2006 | Malewicz |
| 2006/0041319 A1 | 2/2006 | Taylor et al. |
| 2006/0047338 A1 | 3/2006 | Jenson et al. |
| 2006/0052816 A1 | 3/2006 | Bates et al. |
| 2006/0052821 A1 | 3/2006 | Abbott et al. |
| 2006/0058865 A1 | 3/2006 | Case et al. |

(56) References Cited

U.S. PATENT DOCUMENTS

| | | |
|---|---|---|
| 2006/0058889 A1 | 3/2006 | Case et al. |
| 2006/0064152 A1 | 3/2006 | Olson |
| 2006/0069430 A9 | 3/2006 | Randert et al. |
| 2006/0074352 A1 | 4/2006 | Case et al. |
| 2006/0074480 A1 | 4/2006 | Bales et al. |
| 2006/0089708 A1 | 4/2006 | Osse et al. |
| 2006/0100531 A1 | 5/2006 | Moser |
| 2006/0106418 A1 | 5/2006 | Seibold et al. |
| 2006/0106420 A1 | 5/2006 | Dolan et al. |
| 2006/0106454 A1 | 5/2006 | Osborne |
| 2006/0106456 A9 | 5/2006 | Machold et al. |
| 2006/0111770 A1 | 5/2006 | Pavcnik et al. |
| 2006/0111773 A1 | 5/2006 | Rittgers et al. |
| 2006/0116548 A1 | 6/2006 | Case et al. |
| 2006/0116572 A1 | 6/2006 | Case |
| 2006/0122646 A1 | 6/2006 | Corcoran et al. |
| 2006/0136044 A1 | 6/2006 | Osborne et al. |
| 2006/0136045 A1 | 6/2006 | Flagle et al. |
| 2006/0155327 A1 | 7/2006 | Briganti et al. |
| 2006/0167468 A1 | 7/2006 | Gabbay |
| 2006/0173532 A1 | 8/2006 | Flagle et al. |
| 2006/0178729 A1 | 8/2006 | Thielen et al. |
| 2006/0178730 A1 | 8/2006 | Hill et al. |
| 2006/0178740 A1 | 8/2006 | Stacchino et al. |
| 2006/0184239 A1 | 8/2006 | Andrieu et al. |
| 2006/0195004 A1 | 8/2006 | Jarvik |
| 2006/0200196 A1 | 9/2006 | Zang et al. |
| 2006/0201996 A1 | 9/2006 | Hodde |
| 2006/0210597 A1 | 9/2006 | Hiles |
| 2006/0210603 A1 | 9/2006 | Williams et al. |
| 2006/0212107 A1 | 9/2006 | Case et al. |
| 2006/0212110 A1 | 9/2006 | Osborne et al. |
| 2006/0212111 A1 | 9/2006 | Case et al. |
| 2006/0216326 A1 | 9/2006 | Pacetti |
| 2006/0217760 A1 | 9/2006 | Widomski et al. |
| 2006/0217761 A1 | 9/2006 | Opolski |
| 2006/0229670 A1 | 10/2006 | Bates |
| 2006/0229702 A1 | 10/2006 | Agnew |
| 2006/0230592 A1 | 10/2006 | Heaney |
| 2006/0235467 A1 | 10/2006 | DeVore |
| 2006/0235511 A1 | 10/2006 | Osborne |
| 2006/0241675 A1 | 10/2006 | Johnson et al. |
| 2006/0241744 A1 | 10/2006 | Beith |
| 2006/0247762 A1 | 11/2006 | Acosta et al. |
| 2006/0253188 A1 | 11/2006 | Case |
| 2006/0259115 A1 | 11/2006 | Case et al. |
| 2006/0259128 A1 | 11/2006 | Pavcnik et al. |
| 2006/0259136 A1 | 11/2006 | Nguyen |
| 2006/0265053 A1 | 11/2006 | Hunt |
| 2006/0271030 A1 | 11/2006 | Francis et al. |
| 2006/0271159 A1 | 11/2006 | Gregorich et al. |
| 2006/0276813 A1 | 12/2006 | Greenberg |
| 2006/0276882 A1 | 12/2006 | Case et al. |
| 2006/0282157 A1 | 12/2006 | Hill et al. |
| 2006/0287717 A1 | 12/2006 | Rowe et al. |
| 2007/0016306 A1 | 1/2007 | Dua et al. |
| 2007/0021826 A1 | 1/2007 | Case |
| 2007/0027460 A1 | 2/2007 | Case et al. |
| 2007/0027535 A1 | 2/2007 | Purdy et al. |
| 2007/0027549 A1 | 2/2007 | Godin |
| 2007/0038291 A1 | 2/2007 | Case |
| 2007/0043431 A1 | 2/2007 | Melsheimer |
| 2007/0056346 A1 | 3/2007 | Spenser |
| 2007/0061002 A1 | 3/2007 | Paul, Jr. et al. |
| 2007/0061009 A1 | 3/2007 | Spenser |
| 2007/0088424 A1 | 4/2007 | Greenberg |
| 2007/0093887 A1 | 4/2007 | Case et al. |
| 2007/0100435 A1 | 5/2007 | Case |
| 2007/0106372 A1 | 5/2007 | Osborne et al. |
| 2007/0112423 A1 | 5/2007 | Chu |
| 2007/0112437 A1 | 5/2007 | Shank |
| 2007/0129738 A1 | 6/2007 | Kraemer et al. |
| 2007/0135826 A1 | 6/2007 | Zaver et al. |
| 2007/0162057 A1 | 7/2007 | Kraemer et al. |
| 2007/0162058 A1 | 7/2007 | Kraemer et al. |
| 2007/0162103 A1 | 7/2007 | Case |
| 2007/0167961 A1 | 7/2007 | Kraemer et al. |
| 2007/0173919 A1 | 7/2007 | Maschke |
| 2007/0185560 A1 | 8/2007 | Roeder et al. |
| 2007/0185565 A1 | 8/2007 | Schwammenthal et al. |
| 2007/0208429 A1 | 9/2007 | Leahy |
| 2007/0213813 A1 | 9/2007 | Segesser et al. |
| 2007/0225798 A1 | 9/2007 | Gregorich |
| 2007/0227518 A1 | 10/2007 | Case |
| 2007/0233237 A1 | 10/2007 | Krivoruchko |
| 2007/0239273 A1 | 10/2007 | Allen |
| 2007/0244545 A1 | 10/2007 | Birdsall et al. |
| 2007/0254005 A1* | 11/2007 | Pathak ............ A61K 35/12 424/423 |
| 2007/0260263 A1 | 11/2007 | Case et al. |
| 2007/0260327 A1 | 11/2007 | Case et al. |
| 2007/0270931 A1 | 11/2007 | Leanna |
| 2007/0270932 A1 | 11/2007 | Headley |
| 2007/0270937 A1 | 11/2007 | Leanna |
| 2007/0288086 A1 | 12/2007 | Kalmann et al. |
| 2007/0288087 A1 | 12/2007 | Gabbay |
| 2008/0009934 A1 | 1/2008 | Schneider |
| 2008/0046071 A1 | 2/2008 | Pavcnik |
| 2008/0051879 A1 | 2/2008 | Case et al. |
| 2008/0082166 A1 | 4/2008 | Styrc et al. |
| 2008/0091235 A1 | 4/2008 | Sirota |
| 2008/0103582 A1 | 5/2008 | Randall et al. |
| 2008/0125860 A1 | 5/2008 | Webler et al. |
| 2008/0140110 A1 | 6/2008 | Spence |
| 2008/0200936 A1 | 8/2008 | Kraemer et al. |
| 2008/0200937 A1 | 8/2008 | Kraemer et al. |
| 2008/0208215 A1 | 8/2008 | Kraemer et al. |
| 2008/0221656 A1 | 9/2008 | Hartley |
| 2008/0228206 A1 | 9/2008 | Kraemer et al. |
| 2008/0228285 A1 | 9/2008 | Kraemer et al. |
| 2008/0243246 A1 | 10/2008 | Ryan et al. |
| 2008/0249538 A1 | 10/2008 | Kraemer et al. |
| 2008/0249609 A1 | 10/2008 | Shanley |
| 2008/0249612 A1 | 10/2008 | Osborne et al. |
| 2008/0249619 A1 | 10/2008 | Stacchino et al. |
| 2008/0275470 A1 | 11/2008 | Kraemer et al. |
| 2008/0281295 A1* | 11/2008 | Chang ............ A61B 17/3415 604/540 |
| 2008/0281337 A1 | 11/2008 | Kraemer et al. |
| 2008/0287966 A1 | 11/2008 | Kraemer et al. |
| 2008/0312735 A1 | 12/2008 | Thorpe et al. |
| 2009/0005863 A1 | 1/2009 | Goetz et al. |
| 2009/0018649 A1 | 1/2009 | Jaffe et al. |
| 2009/0062836 A1 | 3/2009 | Kurrus |
| 2009/0062844 A1 | 3/2009 | Tekulve |
| 2009/0082858 A1 | 3/2009 | Nugent et al. |
| 2009/0088836 A1 | 4/2009 | Bishop et al. |
| 2009/0099653 A1 | 4/2009 | Suri et al. |
| 2009/0105813 A1 | 4/2009 | Chambers et al. |
| 2009/0118712 A1 | 5/2009 | Carter et al. |
| 2009/0177275 A1 | 7/2009 | Case |
| 2009/0216321 A1 | 8/2009 | Osborne et al. |
| 2009/0234434 A1 | 9/2009 | Johnson et al. |
| 2009/0240320 A1 | 9/2009 | Tuval et al. |
| 2009/0248132 A1 | 10/2009 | Bloom et al. |
| 2009/0264991 A1 | 10/2009 | Paul et al. |
| 2009/0270965 A1 | 10/2009 | Sinha et al. |
| 2009/0287300 A1 | 11/2009 | Dave et al. |
| 2010/0023114 A1 | 1/2010 | Chambers et al. |
| 2010/0030246 A1 | 2/2010 | Pavcnik et al. |
| 2010/0030259 A1 | 2/2010 | Pavcnik et al. |
| 2010/0030314 A1 | 2/2010 | Case et al. |
| 2010/0057191 A1 | 3/2010 | Pavcnik et al. |
| 2010/0063577 A1 | 3/2010 | Case et al. |
| 2010/0114296 A1 | 5/2010 | Case et al. |
| 2010/0114300 A1 | 5/2010 | Case et al. |
| 2010/0121461 A1 | 5/2010 | Sobrino-Serrano et al. |
| 2010/0121462 A1 | 5/2010 | Sobrino-Serrano et al. |
| 2010/0131055 A1 | 5/2010 | Case et al. |
| 2010/0137998 A1 | 6/2010 | Sobrino-Serrano et al. |
| 2010/0174364 A1 | 7/2010 | Hoffman et al. |
| 2010/0185277 A1 | 7/2010 | Braido et al. |
| 2011/0022157 A1* | 1/2011 | Essinger et al. ........ 623/1.26 |
| 2011/0054497 A1 | 3/2011 | Kraemer et al. |

(56) References Cited

U.S. PATENT DOCUMENTS

| | | | |
|---|---|---|---|
| 2011/0087198 A1 | 4/2011 | Carter et al. | |
| 2011/0087337 A1 | 4/2011 | Forsell | |
| 2011/0160753 A1 | 6/2011 | Bastin | |
| 2011/0190796 A1 | 8/2011 | Kraemer et al. | |
| 2011/0190905 A1 | 8/2011 | Behan | |
| 2011/0202078 A1 | 8/2011 | Kraemer et al. | |
| 2012/0078347 A1 | 3/2012 | Braido et al. | |
| 2012/0130476 A1 | 5/2012 | Paul et al. | |
| 2012/0203327 A1 | 8/2012 | Case et al. | |
| 2012/0253446 A1 | 10/2012 | Osborne et al. | |
| 2012/0253450 A1 | 10/2012 | Case et al. | |
| 2012/0323306 A1 | 12/2012 | Case et al. | |
| 2012/0330413 A1 | 12/2012 | Pavcnik | |
| 2013/0018453 A1 | 1/2013 | Case et al. | |
| 2013/0079867 A1 | 3/2013 | Hoffman et al. | |
| 2013/0079868 A1 | 3/2013 | Agnew | |
| 2013/0110254 A1 | 5/2013 | Osborne | |
| 2013/0116720 A1 | 5/2013 | Theobald et al. | |
| 2013/0123768 A1 | 5/2013 | Harlan | |
| 2013/0226291 A1 | 8/2013 | Pavcnik et al. | |
| 2013/0238088 A1* | 9/2013 | Navia | A61F 2/2418 623/2.11 |
| 2013/0289706 A1 | 10/2013 | Schaeffer et al. | |
| 2014/0107691 A1 | 4/2014 | Lashinski | |
| 2014/0143236 A1 | 5/2014 | Thompson | |
| 2014/0155987 A1 | 6/2014 | Paul et al. | |
| 2014/0163667 A1 | 6/2014 | Lashinski et al. | |
| 2014/0228937 A1 | 8/2014 | Krieger et al. | |

FOREIGN PATENT DOCUMENTS

| | | |
|---|---|---|
| AU | 2004220576 | 9/2004 |
| CA | 2381787 | 3/2001 |
| CA | 2401996 | 3/2001 |
| CA | 2403030 | 9/2002 |
| CA | 2518867 | 9/2004 |
| CA | 2523262 | 11/2004 |
| DE | 2246526 | 3/1973 |
| DE | 19851846 | 5/2000 |
| DE | 10223399 | 12/2003 |
| EP | 103546 | 3/1984 |
| EP | 0350302 | 1/1990 |
| EP | 0357003 | 3/1990 |
| EP | 0386936 | 9/1990 |
| EP | 0520126 | 11/1991 |
| EP | 460428 | 12/1991 |
| EP | 0493788 | 7/1992 |
| EP | 0592410 | 4/1994 |
| EP | 0657147 | 6/1995 |
| EP | 0732089 | 9/1996 |
| EP | 0800801 | 6/1997 |
| EP | 0792627 | 9/1997 |
| EP | 0808614 | 11/1997 |
| EP | 0850607 | 7/1998 |
| EP | 0938880 | 9/1999 |
| EP | 1057460 | 12/2000 |
| EP | 1179321 | 2/2002 |
| EP | 1230901 | 8/2002 |
| EP | 1362563 | 11/2003 |
| EP | 1472996 | 4/2004 |
| EP | 1615595 | 4/2004 |
| EP | 1579886 | 9/2005 |
| EP | 1434538 | 1/2007 |
| EP | 1626681 | 7/2009 |
| EP | 1603492 | 12/2009 |
| EP | 1615593 | 1/2010 |
| EP | 2163224 | 3/2010 |
| EP | 2201911 | 6/2010 |
| EP | 1229865 | 11/2010 |
| EP | 2120795 | 7/2011 |
| EP | 2222247 | 8/2012 |
| EP | 1887980 | 9/2012 |
| EP | 1928512 | 11/2012 |
| EP | 1659992 | 3/2013 |
| FR | 2722678 | 7/1994 |
| FR | 2785174 | 5/2000 |
| FR | 2788217 | 7/2000 |
| FR | 2828091 | 2/2003 |
| GB | 1598111 | 4/1977 |
| GB | 2056023 | 3/1981 |
| GB | 2398245 | 8/2004 |
| JP | 6137556 | 6/1986 |
| JP | S62-27352 | 2/1987 |
| JP | 02-307480 | 12/1990 |
| JP | 4383707 | 10/2009 |
| JP | 4589395 | 12/2010 |
| JP | 4624984 | 12/2010 |
| JP | 4940388 | 3/2012 |
| SU | 1258406 | 9/1986 |
| SU | 1271508 | 11/1986 |
| SU | 1371701 | 2/1988 |
| WO | 8302225 | 7/1983 |
| WO | WO8501651 | 4/1985 |
| WO | 9014804 | 12/1990 |
| WO | 9117720 | 11/1991 |
| WO | 9209247 | 11/1991 |
| WO | 9217118 | 10/1992 |
| WO | WO9407560 | 4/1994 |
| WO | WO95277448 | 10/1995 |
| WO | 9637167 | 11/1996 |
| WO | 9640008 | 12/1996 |
| WO | 9640011 | 12/1996 |
| WO | 9724082 | 7/1997 |
| WO | 9725937 | 7/1997 |
| WO | WO9728744 | 8/1997 |
| WO | 9732543 | 9/1997 |
| WO | 9819732 | 11/1997 |
| WO | 9822045 | 5/1998 |
| WO | 9825636 | 6/1998 |
| WO | 9825637 | 6/1998 |
| WO | 9826291 | 6/1998 |
| WO | WO9827868 | 7/1998 |
| WO | 9846165 | 10/1998 |
| WO | WO9846165 | 10/1998 |
| WO | 9858600 | 12/1998 |
| WO | 9915224 | 4/1999 |
| WO | 9933414 | 7/1999 |
| WO | 9959503 | 11/1999 |
| WO | 9962431 | 12/1999 |
| WO | 0040176 | 7/2000 |
| WO | 0042950 | 7/2000 |
| WO | 0047134 | 8/2000 |
| WO | 0064380 | 11/2000 |
| WO | 0067661 | 11/2000 |
| WO | 0067679 | 11/2000 |
| WO | 0112105 | 2/2001 |
| WO | 0119285 | 3/2001 |
| WO | 0128459 | 4/2001 |
| WO | 0130275 | 5/2001 |
| WO | 0149213 | 7/2001 |
| WO | 0154625 | 8/2001 |
| WO | 0156500 | 8/2001 |
| WO | 0166035 | 9/2001 |
| WO | 0166037 | 9/2001 |
| WO | 0166043 | 9/2001 |
| WO | 0166190 | 9/2001 |
| WO | 0174273 | 10/2001 |
| WO | 200183017 | 11/2001 |
| WO | 0207601 | 1/2002 |
| WO | 2002024119 | 3/2002 |
| WO | 0236045 | 5/2002 |
| WO | 0239888 | 5/2002 |
| WO | 0241764 | 5/2002 |
| WO | 0243620 | 6/2002 |
| WO | 0249541 | 6/2002 |
| WO | 02102284 | 12/2002 |
| WO | 03002165 | 1/2003 |
| WO | 03011195 | 2/2003 |
| WO | 03030776 | 4/2003 |
| WO | 03030782 | 4/2003 |
| WO | 03047468 | 6/2003 |
| WO | 03063733 | 8/2003 |
| WO | 03088872 | 10/2003 |

(56) References Cited

FOREIGN PATENT DOCUMENTS

| WO | 03092554 | 11/2003 |
|---|---|---|
| WO | 03101346 | 12/2003 |
| WO | 2003101346 | 12/2003 |
| WO | 2004016200 | 2/2004 |
| WO | 2004016201 | 2/2004 |
| WO | 2004045703 | 6/2004 |
| WO | 2004080352 | 9/2004 |
| WO | 2004082528 | 9/2004 |
| WO | 2004082530 | 9/2004 |
| WO | 091449 | 10/2004 |
| WO | 2004089253 | 10/2004 |
| WO | 2004091449 | 10/2004 |
| WO | 2004093745 | 11/2004 |
| WO | 2004096100 | 11/2004 |
| WO | 2004103222 | 12/2004 |
| WO | 2004105651 | 12/2004 |
| WO | 2005011535 | 2/2005 |
| WO | WO2005020612 | 3/2005 |
| WO | 05062931 | 7/2005 |
| WO | 2005082289 | 9/2005 |
| WO | 2005099623 | 10/2005 |
| WO | 2005099628 | 10/2005 |
| WO | 2006026325 | 3/2006 |
| WO | 2006028821 | 3/2006 |
| WO | 2006031436 | 3/2006 |
| WO | WO2006026325 | 3/2006 |
| WO | 2006050460 | 5/2006 |
| WO | 2006071245 | 7/2006 |
| WO | 2006124647 | 11/2006 |
| WO | 2006125055 | 11/2006 |
| WO | 2007047945 | 4/2007 |
| WO | 2007061801 | 5/2007 |
| WO | WO2007092274 | 8/2007 |
| WO | 07108857 | 9/2007 |
| WO | 2007123658 | 11/2007 |
| WO | 2007130614 | 11/2007 |
| WO | 2007139677 | 12/2007 |
| WO | 2007142935 | 12/2007 |
| WO | 2008073582 | 6/2008 |
| WO | WO2008073582 | 6/2008 |
| WO | 2008094706 | 8/2008 |
| WO | 2008101083 | 8/2008 |
| WO | 08150529 | 12/2008 |
| WO | 2009052340 | 4/2009 |
| WO | 2009073774 | 6/2009 |
| WO | 2009088957 | 7/2009 |
| WO | 2009129481 | 10/2009 |
| WO | 2010042950 | 4/2010 |
| WO | 2010080884 | 7/2010 |
| WO | 2010091188 | 8/2010 |
| WO | WO2010091188 | 8/2010 |
| WO | 2010099209 | 9/2010 |
| WO | 2011109450 | 9/2011 |
| WO | WO2011109450 | 9/2011 |
| WO | 2012051489 | 4/2012 |
| WO | 2013120082 | 8/2013 |
| WO | WO03092554 | 11/2013 |
| WO | 2014124356 | 8/2014 |

OTHER PUBLICATIONS https://www.dictionary.com/browse/viscera (Year: 2019).*
European Patent Office, European Search Report & Written Opinion of the International Searching Authority, dated Apr. 18, 2012, for International Application No. PCT/US2011/056278.
Kinney, T.E., et al., "Acute, reversible tricuspid insufficiency: creation in canine model," Am. J. Physiol. Heart Circ. Physiol. 260: H638-H641, 1991.
Bai, Yuan, et al., "Percutaneous establishment of tricuspid regugitation: an experimental model for transcatheter tricuspid valve replacement," Chin. Med. J. 2010; 123(7), pp. 806-809.
International Search Report for PCT Application No. PCT/2008/052286, dated Jun. 17, 2008.
Written Opinion for PCT Application No. PCT/2008/052286, dated Jun. 17, 2008.
Lamba, et al., "Degradation of Polyurethanes," Polyurethanes in Biomedical Applications, 181-204, 1998.
Matthias Chiquet, "Regulation of extracellular matrix gene expression by mechanical stress," Matrix Biol., 417-426, 1999.
Marcy Wong, Mark Siegrist, Xuesong Cao, "Cyclic compression of articular cartilage explants is associated with progressive consolidation and altered expression pattern of extracellular matrix proteins," Matrix Biology, 391-399, 1999.
Alan J. Grodzinsky, Marc E. Levenston, Moonsoo Jin, Eliot H. Frank, "Cartilage Tissue Remodeling in Response to Mechanical Forces," Annual Review of Biomedical Engineering, 691-713, 2000.
V.C. Mudera, R. Pleass, M. Eastwood, R. Tarnuzzer, G. Schultz, P. Khaw, D.A. Mcgrouther, R.A. Brown, "Molecular Responses of Human Dermal Fibroblasts to Dual Cues: Contact Guidance and Mechanical Load," Cell Motility and the Cytoskeleton, 45: 1-9, 2000.
Christof Schild, Beat Trueb, "Mechanical Stress is Required for High-Level Expression of Connective Tissue Growth Factor," Experimental Cell Research, 274: 83-91, 2002.
European Patent Office, International Preliminary Report on Patentability, dated May 30, 2006, for International application No. PCT/US2005012421.
European Patent Office, Written Opinion of the International Searching Authority, dated Oct. 13, 2006, for International application No. PCT/US2005/012421.
European Patent Office, Later Publication of the International Search Report, dated Jul. 8, 2005 for International application No. PCT/US2005/012421.
Braun, M., et al., "Transcatheter Closure of Patent Foramen Ovale (PFO) in Patients With Paradoxical Embolism", European Heart Journal (2004), vol. 25, pp. 424-430.
Das, Gladwin S., et al., "Experimental Atrial Septal Defect Closure With a New, Transcatheter, Self-Centering Device", Circulation, vol. 88, No. 4, Part 1, Oct. 1993, pp. 1754-1764.
Heeschen, Christopher, et al., "Nicotine Stimulates Angiogensis and Promotes Tumor Growth and Atherosclerosis", Nature Medicine vol. 7, No. 7, (Jul. 2001), pp. 833-839.
Johnson, Chad, et al., "Matrix Metalloproteinase-9 is Required for Adequate Angiogenic Revascularization of Ischemic Tissues", Circulation Research, Feb. 6, 2004, No. 94, pp. 262-268.
Jux, Christian, et al., "A New Biological Matrix for Septal Occlusion", Journal of Interventional Cardiology, vol. 16, No. 2, (2003), pp. 149-152.
King, Terry D., et al., "Secundum Atrial Septal Defect-Nonoperative Closure During Cardiac Catheterization", JAMA, vol. 235, No. 23, Jun. 7, 1978, pp. 2506-2509.
Mullen, Michael J., et al., "BioSTAR Evaluation STudy (BEST) A Prospective, Multicenter, Phase I Clinic Trial to Evaluate the Feasibility, Efficacy, and Safety of the BioSTAR Bioabsorbable Septal Repair Implant for the Closure of Atrial-Level Shunts", Circulation, Oct. 31, 2006, pp. 19621967.
Oguchi, M., et al., "Mucosa-adhesive water-soluble polymer film for treatment of acute radiation-induced oral mucositis", International Journal of Radiation Oncology Biology Physics, Mar. 15, 1998, vol. 40, No. 5, p. 1033-1037.
Pavcnik, Dusan et al., "Monodisk: Device for Percutaneous Transcatheter Closure of Cardiac Septal Defects", Cardiovasc Intervent Radio (1993) vol. 16, pp. 308-312.
Rashkind, William J., "Transcatheter Treatment of Congenital Heart Disease", Circulation vol. 67, No. 4, Apr. 1983, pp. 711-716.
Sideris, E.B. et al., "Transvenous Atrial Septal Defect Occlusion in Piglets with a 'Buttoned' Double-Disk Device", Circulation, vol. 81, No. 1, Jan. 1990, pp. 312-318.
Jux, Christian, et al., "Interventional Atrial Septal Defect Closure Using a Totally Bioresorbable Occluder Matrix", JACC, vol. 48, No. 1 (2006), pp. 161-169.
Babic, Uros U., et al., "Transcatheter Closure of Atrial Septal Defects", The Lancet, Sep. 1, 1990, pp. 566-567.

(56) References Cited

OTHER PUBLICATIONS

Bhattathiri, VN, et al., "Influence of plasma GSH level on acute radiation mucositis of the oral cavity", International Journal of Radiation Oncology Biology Physics (1994), vol. 29, No. 2, pp. 383-386.
Complete Prosecution History, U.S. Appl. No. 13/461,260, Compiled Feb. 13, 2014.
Complete Prosecution History, U.S. Appl. No. 13/930,723, Compiled Feb. 6, 2014.
Complete Prosecution History, U.S. Pat. No. 8,475,516, Compiled Feb. 6, 2014.
Complete Prosecution History, U.S. Pat. No. 8,109,990, Compiled Feb. 6, 2014.
Lurie, Fedor Mechanism of Venous Valve Closure and Role of the Valve in Circulation: A New Concept, J Vasc Surg 2003;38:955-61. Elsevier, Amsterdam, The Netherlands.
Lurie, Fedor, The Mechanism of Venous Valve Closure in Normal Physiologic Conditions, J Vasc Surg 2002;35:713-17. Elsevier, Amsterdam, The Netherlands.
Van Bemmelen, Paul S. and Fedor Lurie, Letters to the Editor, Regarding "The Mechanism of Venous Valve Closure in Normal Physiological Conditions", J Vasc Surg 2003; 37(1) 237-38. Elsevier, Amsterdam, The Netherlands.
Garcia-Rinaldi, Raul, Implantation of Cryopreserved Allograft Pulmonary Monocusp Patch, Tex Heart Inst J 2002;29:92-99. Texas Heart Institute, Houston, TX, USA.
Garcia-Rinaldi, Raul, Femoral Vein Valve Incompetence: Treatment with a Xenograft Monocusp Patch, J Vasc Surg 1986; 932-35. Elsevier, Amsterdam, The Netherlands.
Dana E. Perrin, James P. English, "Polycaprolactone," Handbook of Bioabsorbable Polymers, 1997, 63-76.
Yuan et al. Geometrical Design and Finite Element Analysis on the Bioprosthetic Heart Valve. International Journal of Innovative Computing, Information and Control. vol. 3 No. 5. Oct. 2007. pp. 1289-1299. [abstract].
Office Action, Summary for U.S. Appl. No. 10/828,716, issued by the USPTO, dated Dec. 31, 2008, pp. 1-8.
Office Action, Summary for U.S. Appl. No. 12/614,878, issued by the USPTO, dated Apr. 12, 2010, pp. 1-17.
Office Action, Summary for U.S. Appl. No. 12/605,585, issued by the USPTO, dated Apr. 14, 2010, pp. 1-21.
Office Action, Summary for U.S. Appl. No. 11/586,285, issued by the USPTO, dated Jul. 16, 2009, pp. 1-9.
Brochure—Aurous Centimeter Sizing Catheters, PFVS899 p. 6.
Wai Hung Wong, David J. Mooney, "Synthesis and Properties of Biodegradable Polymers Used as Synthetic Matrices for Tissue Engineering," I synthetic Biodegradable Polymer Scaffolds, 1997, 51-82.
Schneider (Eur.) AG v. Scimed Life Sys., 852 F. Supp. 813 (D. Minn. 1994).
European Patent Office Communication for European patent application No. 07/794571.5 dated Feb. 25, 2011.
Office Action issued by the United States Patent and Trademark Office dated Jul. 30, 2009 in U.S. Appl. No. 10/903,907.
File history of U.S. Appl. No. 12/252,253, filed Oct. 15, 2008. Inventor, Norman Jaffe. Title, Biological Valve for Venous Valve Insufficiency.
File history of U.S. Appl. No. 12/789,176, filed May 27, 2010. Inventor, Norman Jaffe. Title, Biological Valve for Venous Valve Insufficiency.
The International Bureau of WIPO, International Preliminary Report on Patentability, dated Jun. 17, 2010, for International Application No. PCT/US2008/085510.
The International Searching Authority, International Search Report and the Written Opinion, dated Mar. 26, 2009, for International Application No. PCT/US2008/085510.
The International Searching Authority, International Search Report and the Written Opinion, dated Jul. 1, 2009, for International Application No. PCT/US2009/040026.
The International Bureau of WIPO, International Preliminary Report on Patentability, dated Jun. 17, 2010, for International Application No. PCT/US2008/085495.
The International Searching Authority, International Search Report and the Written Opinion, dated Apr. 2, 2009, for International Application No. PCT/US2008/085495.
European Patent Office, The International Search Report and the Written Opinion of the International Searching Authority, dated Feb. 1, 2010, International Application No. PCT/US2009/051612.
International Preliminary Report on Patentability, The International Bureau of WIPO, dated Feb. 3, 2011, for PCT International Application No. PCT/US2009/051612.
European Search Report and Search Opinion, issued by the European Patent Office, dated Nov. 9, 2009 for Application No. 09170581.4-2320.
Extended European Search Report, mailed by the European Patent Office dated Feb. 16, 2010 for Application No. 09180708.1-2320, pp. 1-6.
Communication pursuant to Article 94(3) EPC, mailed by the European Patent Office dated Oct. 5, 2010 for Application No. 09180708.1, p. 1.
Communication pursuant to Article 94(3) EPC, mailed by the European Patent Office dated Dec. 5, 2013 for Application No. 09180708.1, pp. 1-4.
Bergan, John J., et al., "Chronic Venous Disease," N. Engl. J. Med. 2006; 355: 488-98.
Dougal et al., "Stent Design: Implications for Restenosis," Rev. Cardiovasc Med. 3 (suppl. 5), S16-S22 (2002).
International Preliminary Report on Patentability, for International Application No. PCT/US2008/083870, dated May 25, 2010, p. 1-7.
European Patent Office, Written Opinion of the International Searching Authority, for International application No. PCT/US2008/083870.
World Intellectual Property Organization, International Application No. PCT/US2008/083870 (Int. Pub. No. WO2009/067432) and published with the International Search Report, dated Feb. 18, 2009, p. 1-52.
Shu Chien, Song Li, John Y-J Shyy, "Effects of Mechanical Forces on Signal Transdution and Gene Expression in Endothelial Cells," Hypertension 31, 162-169, 1998.
Stephen Badylak, Ph.D., M.D., Klod Lokini, Ph.D., Bob Tullius, M.S., Abby Simmons-Byrd, R.V.T., and Robert Morff, Ph.D., "Morphologic Study of Small Intestinal Submucosa as a Body Wall Repair Device," Journal of Surgical Research, 103, 190-202 (2002).
Elias Brountzos, MD, Dusan Pavcnik, MD, PhD, Hans A. Timmermans, BFA, Christopher Corless, MD, PhD, Barry T. Uchida, BS, Edith S, Nihsen, BA, Manabu Nakata, MD, PhD, Maria Schoder, MD, John A. Kaufman, MD, Frederick S. Keller, MD, and Josef Rosch, MD, "Remodeling of Suspended Small Intestinal Submucosa Venous Valve: An Experimental Study in Sheep to Assess the Host Cells' Origin," J. Vasc. Interv. Radiol, 2003 14:349-356.
Stephen S. Kim, Satoshi Kaihara, Mark S. Benvenuto, Byung-Soo Kim, David J. Mooney, and Joseph P. Vacanti, "Small Intestinal Submucosa as a Small-Caliber Venous Graft: A Novel Model for Hepatocyte Transplantation on Synthetic Biodegradable Polymer Scaffolds with Direct Access to the Portal Venous System," Journal of Pediatric Surgery, vol. 34, No. 1 (1999) 124-128.
G.E. Sandusky, Jr., S.F. Badylak, R.J. Morff, W.D. Johnson, and G. Lantz, "Histologic Findings After In Vivo Placement of Small Intestine Submucosal Vascular Grafts and Saphenous Vein Grafts in the Carotid Artery in Dogs," American Journal of Pathology, vol. 140, No. 2 1992, 317-324.
International Searching Authority, The International Search Report and Written Opinion of the International Searching Authority, dated May 20, 2010, for International Application No. PCT/US2010/025245.
International Search Report for corresponding international application No. PCT/US2008/052151, dated Jul. 2, 2008.
Written Opinion of the International Searching Authority for corresponding international application No. PCT/US2008/052151, dated Jul. 2, 2008.

(56) References Cited

OTHER PUBLICATIONS

D.K. Gilding, A.M. Reed, "Biodegradable polymers for use in surgery—polyglycolic/poly(actic acid) homo- and copolymers: 1," Polymer, 1997, vol. 20, 1459-1464.

D.K. Gilding, "Biodegradable Polymers," Biocompatibility of Clinical Implant Materials, Chap. 9, pp. 209-232, 1981.

Gabriel Helmlinger, Bradford C. Berk, Robert M. Nerem, "Calcium responses of endothelial cell monolayers subjected to pulsatile and steady laminar flow differ," Am. J. Physiol. Cell Physiol., 269: C367-C375, 1995.

Matthias Chiquet, Mark Matthisson, Manuel Koch, Michael Tannheimer, Ruth Chiquet-Ehrismann, "Regulation of extracellular matrix synthesis by mechanical stress," Biochem. Cell Biol. 74, 737-744 (1996).

Yi-Shuan Li, John Y.-J Shyy, Song Li, Jongdae Lee, Bing US, Michael Karin, Shu Chien, "The Ras-JNK Pathway Is Involved in Shear-Induced Gene Expression," Molecular and Cellular Biology, 1996, 5947-5954.

European Patent Office, "Extended European Search Report," for Int. App. No. 13746917.7, dated Sep. 8, 2015, pp. 1-8.

European Patent Office, "Communication pursuant to Article 94(3) EPC," for European Application No. 13746917.7, dated Jun. 2, 2016, pp. 1-4.

European Patent Office, Extended European Search Report for Application No. 17191957.4, dated Dec. 13, 2017, pp. 1-8.

European Patent Office, Examination Report, for European application No. 17191957.4, dated Oct. 21, 2019, pp. 1-4.

\* cited by examiner

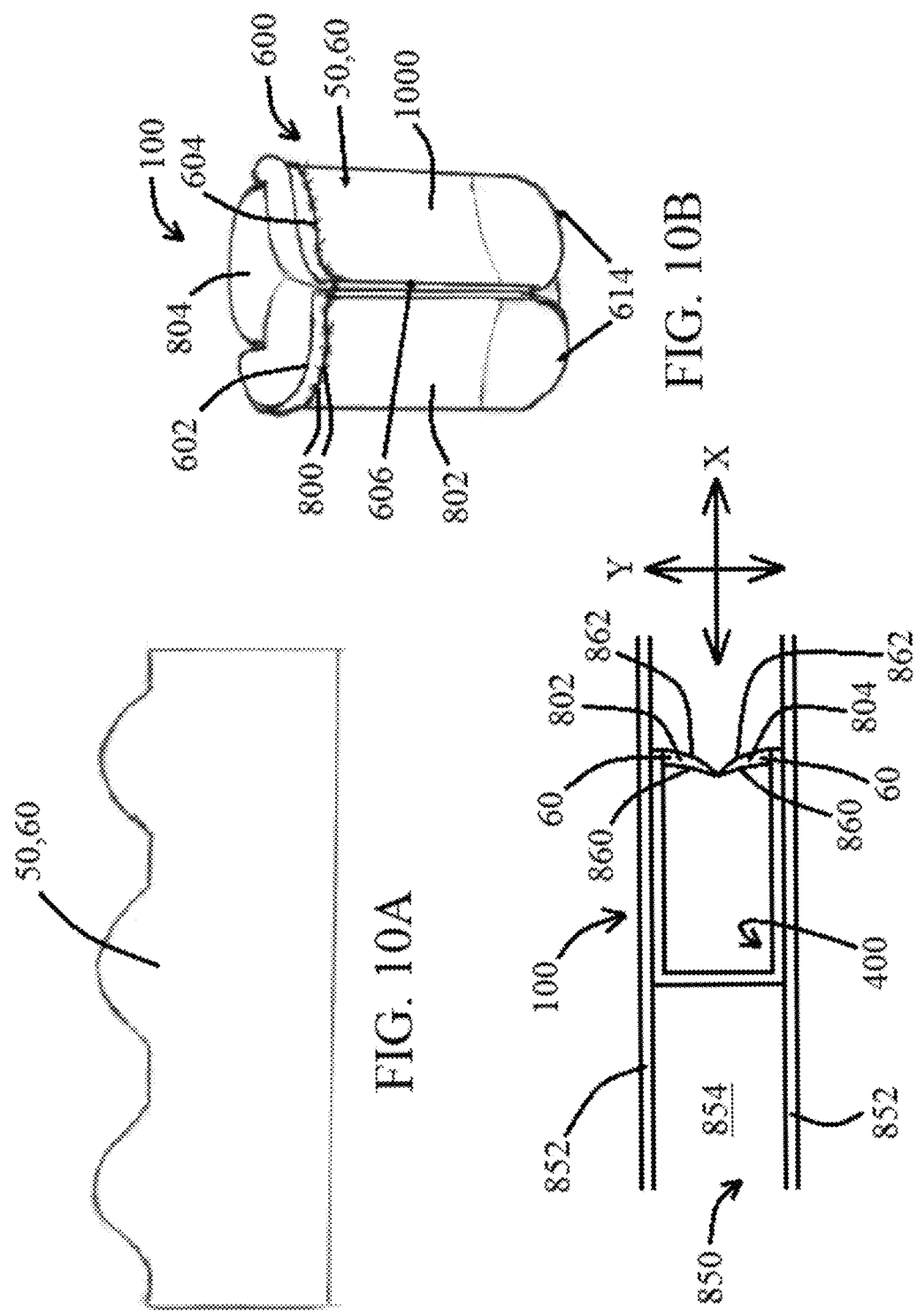

METHODS AND USES OF BIOLOGICAL TISSUES FOR VARIOUS STENT AND OTHER MEDICAL APPLICATIONS

PRIORITY

The present application is related to, and claims the priority benefit of, U.S. Provisional Patent Application Ser. No. 61/640,381, filed Apr. 30, 2012, and U.S. Provisional Patent Application Ser. No. 61/597,406, filed Feb. 10, 2012, the contents of which are hereby incorporated by reference in their entirety into this disclosure.

BACKGROUND

To date, the small intestinal submucosa (SIS) is the major biological tissue scaffold that has garnered some biological applications to replace or augment injured or damaged biological tissues. Once the smooth muscles are stripped away, the SIS consists of largely collagen and some elastin fibers. The fixation of the tissue, however, renders the scaffold stiff and can result in losses of some of its biological advantages.

In view of the same, it would be advantageous to identify and process an effective alternative tissue that would maintain its elasticity, keep its biological advantages, and be useful for various bodily purposes, including as part of various medical devices.

BRIEF SUMMARY

In an exemplary embodiment of a method of processing pulmonary ligament tissue of the present disclosure, the method comprises the steps of acquiring a mammalian tissue comprising at least a portion of a pulmonary ligament, selecting a sample of pulmonary ligament tissue from the at least a portion of pulmonary ligament, and fixing the sample of pulmonary ligament tissue using a fixative, resulting in a fixed sample.

In an exemplary embodiment of a method of processing a tissue of the present disclosure, the method comprises the steps of acquiring a mammalian tissue comprising at least a portion of a pulmonary region tissue, selecting a sample of pulmonary region tissue from the at least a portion of a pulmonary region tissue, and fixing the sample of pulmonary region tissue using a fixative, resulting in a fixed sample. In another embodiment, the step of acquiring comprises acquiring the at least a portion of a pulmonary region tissue by way of dissecting or resecting tissue from a deceased mammal. In yet another embodiment, the step of acquiring comprises acquiring the at least a portion of a pulmonary region tissue from a mammal selected from the group consisting of a pig, a horse, a cow, a goat, a sheep, and a human. In an additional embodiment, the step of acquiring comprises acquiring the at least a portion of a pulmonary region tissue from a larger quantity of mammalian tissue comprising at least a portion of a lung, at least a portion of an aorta, and at least a portion of a pulmonary ligament.

In an exemplary embodiment of a method of processing a tissue of the present disclosure, the step of acquiring comprises acquiring the at least a portion of a pulmonary region tissue from a larger quantity of mammalian tissue comprising at least a portion of a lung, at least a portion of an esophagus, and at least a portion of a pulmonary ligament. In an additional embodiment, the step of selecting a sample of pulmonary region tissue comprises selecting a sample of pulmonary ligament tissue from the mammalian tissue. In yet an additional embodiment, the step of selecting a sample of pulmonary region tissue comprises selecting a sample of visceral pleura tissue from the mammalian tissue. In another embodiment, the step of selecting a sample of pulmonary region tissue comprises selecting the sample of pulmonary region tissue from the at least a portion of a pulmonary region tissue by cleaning the at least a portion of a pulmonary region tissue to remove blood from the at least a portion of a pulmonary region tissue. In yet another embodiment, the step of selecting a sample of pulmonary region tissue comprises selecting a sample of pulmonary ligament tissue from the at least a portion of a pulmonary region tissue by cleaning the at least a portion of a pulmonary region tissue to remove blood from the at least a portion of a pulmonary region tissue.

In an exemplary embodiment of a method of processing a tissue of the present disclosure, the step of selecting a sample of pulmonary region tissue comprises selecting a sample of visceral pleura tissue from the at least a portion of a pulmonary region tissue by cleaning the at least a portion of a pulmonary region tissue to remove blood from the at least a portion of a pulmonary region tissue. In another embodiment, the step of selecting a sample of pulmonary region tissue comprises selecting the sample of pulmonary region tissue from the at least a portion of a pulmonary region tissue by removing fatty material from the at least a portion of a pulmonary region tissue. In yet another embodiment, the step of selecting a sample of pulmonary region tissue comprises selecting a sample of pulmonary ligament tissue from the at least a portion of a pulmonary region tissue by removing fatty material from the at least a portion of a pulmonary region tissue. In an additional embodiment, the step of selecting a sample of pulmonary region tissue comprises selecting a sample of visceral pleura tissue from the at least a portion of a pulmonary region tissue by removing fatty material from the at least a portion of a pulmonary region tissue.

In an exemplary embodiment of a method of processing a tissue of the present disclosure, the step of selecting a sample of pulmonary region tissue comprises selecting the sample of pulmonary region tissue from the at least a portion of a pulmonary region tissue that is free or substantially free of perforations. In an additional embodiment, the step of selecting a sample of pulmonary region tissue comprises selecting a sample of pulmonary ligament tissue from the at least a portion of a pulmonary region tissue that is free or substantially free of perforations. In yet an additional embodiment, the step of selecting a sample of pulmonary region tissue comprises selecting a sample of visceral pleura tissue that is free or substantially free of perforations. In another embodiment, the step of selecting a sample of pulmonary region tissue comprises selecting the sample of pulmonary region tissue from the at least a portion of a pulmonary region tissue that is free or substantially free of blood or blood vessels.

In an exemplary embodiment of a method of processing a tissue of the present disclosure, the step of selecting a sample of pulmonary region tissue comprises selecting a sample of pulmonary ligament tissue from the at least a portion of a pulmonary region tissue that is free or substantially free of blood or blood vessels. In another embodiment, the step of selecting a sample of pulmonary region tissue comprises selecting a sample of visceral pleura tissue that is free or substantially free of blood or blood vessels. In yet another embodiment, the step of selecting a sample of pulmonary region tissue comprises selecting the sample of pulmonary region tissue from the at least a portion of a pulmonary region tissue that is free or substantially free of irregularities. In an additional embodiment, the step of selecting a sample of pulmonary region tissue further comprises placing the sample of pulmonary region tissue in a saline solution.

In an exemplary embodiment of a method of processing a tissue of the present disclosure, the step of selecting a sample of pulmonary region tissue further comprises placing the sample of pulmonary region tissue in a solution at least 20° F. below ambient temperature. In an additional embodiment, the method further comprises the step of placing the sample of pulmonary region tissue within or upon a mount having known dimensions, wherein the placing step is performed prior to the fixing step. In yet an additional embodiment, the step of placing the sample of pulmonary region tissue within or upon a mount is performed by placing the sample of pulmonary region tissue within or upon a circular or relatively circular mount and securing the sample of pulmonary region tissue to the mount. In another embodiment, the step of placing the sample of pulmonary region tissue within or upon a mount is performed by placing the sample of pulmonary region tissue within or upon a square or rectangular mount and securing the sample of pulmonary region tissue to the mount. In yet another embodiment, the step of placing the sample of pulmonary region tissue within or upon a mount is performed by placing the sample of pulmonary region tissue within or upon a multidimensional mount and securing the sample of pulmonary region tissue to the mount. In an additional embodiment, the fixed sample maintains or closely resembles the known dimensions of the mount.

In an exemplary embodiment of a method of processing a tissue of the present disclosure, the method further comprises the step of securing the sample of pulmonary region tissue within or upon the mount, wherein the securing step is performed prior to the fixing step. In another embodiment, the securing step performed using a securing member selected from the group consisting of one or more sutures, one or more clamps, and one or more forceps. In yet another embodiment, the step of fixing the sample of pulmonary region tissue using a fixative is performed by fixing the sample of pulmonary region tissue using the fixative selected from the group consisting of glutaraldehyde, formaldehyde, and glycerol. In an additional embodiment, the step of fixing the sample of pulmonary region tissue using a fixative is performed by fixing the sample of pulmonary region tissue using the fixative within a HEPES or phosphate buffer. In yet an additional embodiment, the step of fixing the sample of pulmonary region tissue using a fixative is performed by fixing the sample of pulmonary region tissue using a fixation procedure selected from the group consisting of aqueous fixation, cryo-preservation, and dry tissue fixation.

In an exemplary embodiment of a method of processing a tissue of the present disclosure, the method further comprises the step of placing at least two dots on the sample of pulmonary region tissue prior to performing the fixing step, wherein distance(s) between the at least two dots are known prior to performing the fixing step. In an additional embodiment, the method further comprises the step of measuring the distance(s) between the at least two dots after performing the fixing step, and comparing the distance(s) between the at least two dots after performing the fixing step to the distances between the at least two dots prior to performing the fixing step. In yet an additional embodiment, the method further comprises the step of determining an amount of shrinkage based upon data collected from the comparing step. In another embodiment, the acquiring step comprises separating the at least a portion of pulmonary region tissue.

In an exemplary embodiment of a method of processing a tissue of the present disclosure, the method further comprises the step of forming the fixed sample into a valve. In another embodiment, method further comprises the step of shaping the fixed sample so that the fixed sample will fit around portions of a frame. In yet another embodiment, the shaping step is performed by stretching the fixed tissue and cutting the fixed tissue to form a desired shape. In an additional embodiment, method further comprises the step of positioning the fixed sample upon portions of the frame, wherein the fixed sample and the frame collectively form a tissue product.

In an exemplary embodiment of a method of processing a tissue of the present disclosure, the method further comprises the step of positioning the fixed sample upon portions of a frame, wherein the fixed sample and the frame collectively form a tissue product. In an additional embodiment, method further comprises the step of securing a portion of the fixed sample to the frame using one or more sutures. In yet an additional embodiment, method further comprises the step of weaving a portion of the fixed sample around at least a portion of the frame to secure the portion of the fixed sample to the frame. In another embodiment, the weaving step is performed to secure the portion of the fixed sample to the frame without requiring sutures.

In an exemplary embodiment of a method of processing a tissue of the present disclosure, the method further comprises the step of weaving a portion of the fixed sample around at least a portion of the frame to secure the portion of the fixed sample to the frame, wherein when the tissue product is positioned within a mammalian luminal organ, the one or more sutures are not in contact with fluid flowing through the mammalian luminal organ. In another embodiment, the method further comprises the step of positioning the tissue product within a mammalian luminal organ so that fluid native to the mammalian luminal organ may pass through a lumen defined within the tissue product. In yet another embodiment, the frame comprises at least one superior arm and at least one inferior arm positioned at or near an inlet portion of the tissue product, the at least one superior arm and the at least one inferior arm configured to receive a first portion of the fixed sample thereon.

In an exemplary embodiment of a method of processing a tissue of the present disclosure, the at least one superior arm and the at least one inferior arm are configured to receive the first portion of the fixed sample thereon, and wherein the method further comprises the step of securing the first portion of the fixed sample to the frame using one or more sutures. In an additional embodiment, the frame further comprises at least one connection portion coupled to at least one of the at least one superior arm and/or the at least one inferior arm, the at least one connection portion extending along a longitudinal axis of the frame and configured to receive a second portion of the fixed sample thereon. In yet an additional embodiment, the connection portion is configured to receive the second portion of the mammalian tissue thereon, and wherein the method further comprises the step of securing the second portion of the fixed sample to the frame using one or more sutures.

In an exemplary embodiment of a method of processing a tissue of the present disclosure, the tissue product comprises a valve having a bileaflet configuration or a trileaflet configuration. In another embodiment, the desired shape results in a valve having symmetrical leaflets. In yet another embodiment, the fixed sample is sized and shaped to substantially or completely similar to an outer perimeter of the frame. In an additional embodiment, the frame further comprises at least one vertical bar coupled to at least one of the at least one superior arm and/or the at least one inferior arm. In yet an additional embodiment, the frame further comprises at least one lower arm coupled to at least one of the at least connection portion and the at least one vertical arm.

In an exemplary embodiment of a method of processing a tissue of the present disclosure, the frame (or tissue product) is configured to move from a first, closed configuration to a second, open configuration. In an additional embodiment, when the frame is in the first, closed configuration, it is configured to fit within a mammalian luminal organ, such as by percutaneous delivery through the mammalian luminal organ. In yet an additional embodiment, the tissue product is configured as a stent valve. In another embodiment, the stent valve is configured for use as a venous valve. In yet another embodiment, the tissue product is configured so that the fluid native to the mammalian luminal organ can pass through an inlet portion of the tissue product and exit from an outlet portion of the tissue product In an exemplary embodiment of a method of processing a tissue of the present disclosure, the fixed sample coupled to the frame operates as a valve. In another embodiment, the fluid native to the mammalian luminal organ is at least partially prevented from flowing from the outlet portion to the inlet portion due to a configuration of the tissue product. In yet another embodiment, the fixed sample comprises mammalian pulmonary ligament. In an additional embodiment, the fixed sample comprises visceral pleura. In yet an additional embodiment, the fixed sample comprises tissue having stretchability and durability properties to allow the fixed sample to move relative to the fluid flow through the lumen defined within the tissue product.

In an exemplary embodiment of a method of processing a tissue of the present disclosure, the frame is capable of expansion using a balloon catheter. In an additional embodiment, the frame is autoexpandable. In yet an additional embodiment, the frame comprises a material selected from the group consisting of nitinol, chromium, cadmium, molybdenum, nickel, a nickel composite, nickel-cadmium nickel-chromium, nitinol palladium, palladium, cobalt, platinum, and stainless steel. In various embodiments, the fixed samples is configured as a products selected from the group consisting of a stent cover, a diaphragm cover, a hernia repair cover, a brain cover, a general organ cover, a wound cover, a prosthetic device cover, a skull cover, a general tissue cover, a tissue valve, a patch, a surgical membrane, a skin substitute, a suture reinforcement, a tubular structure, a tendon replacement, a bladder tissue replacement, a urethra tissue replacement, a vaginal tissue replacement, a muscle replacement, and another tissue replacement.

In an exemplary embodiment of a method of processing a tissue of the present disclosure, the positioning step is performed by positioning at least part of the fixed sample around the at least part of the frame. In another embodiment, the positioning step is performed by positioning at least part of the fixed sample around one or more of a superior arm, an inferior arm, and a connection portion of the frame. In yet another embodiment, the positioning step is performed by positioning at least part of the fixed sample around at least part of the frame so that at least part of the fixed sample operates as one or more valve leaflets.

In an exemplary embodiment of a method of processing a tissue of the present disclosure, the method further comprises the step of forming the fixed sample into a product configured for mammalian treatment or therapy. In an additional embodiment, the step of fixing the sample of pulmonary region tissue comprises fixing a sample of pulmonary ligament tissue, resulting in a fixed pulmonary ligament sample. In yet an additional embodiment, the step of fixing the sample of pulmonary region tissue comprises fixing a sample of visceral pleura tissue, resulting in a fixed visceral pleura sample.

In an exemplary embodiment of a method of processing a tissue of the present disclosure, the placing step is performed in connection with stretching the fixed sample in a first direction. In another embodiment, the placing step is performed in connection with stretching the fixed sample in a second direction different from the first direction. In yet another embodiment, the method further comprises the step of determining lengths of one or more fibers of the sample of pulmonary region tissue prior to, during, or after the fixing step. In an additional embodiment, the method further comprises the step of determining desmosine content of the sample of pulmonary region tissue prior to, during, or after the fixing step.

In an exemplary embodiment of a method of processing a tissue of the present disclosure, the acquiring step is performed to acquire the at least a portion of pulmonary region tissue from a mammalian heart/lung block. In another embodiment, the method further comprises the step of preseeding the sample of pulmonary region tissue to facilitate endothelialization prior to performing the fixing step. In yet another embodiment, wherein the fixed sample is between about 40 and about 300 microns in thickness. In an additional embodiment, the fixed sample comprises pulmonary ligament tissue having a thickness of between about 80 microns and about 120 microns, and even as high as about 300 microns. In yet an additional embodiment, the fixed sample comprises visceral pleura tissue having a thickness of between about 40 microns and about 80 microns.

In an exemplary embodiment of a method of processing a tissue of the present disclosure, the acquiring step is performed to acquire the at least a portion of a pulmonary region tissue from a middle-anterior portion of at least one lung of the mammal. In another embodiment, the acquiring step is performed to acquire the at least a portion of a pulmonary region tissue by making an incision in the at least one lung and pressing tissue of the at least one lung away from a visceral pleura. In yet another embodiment, the fixing step is performed using a fixative comprising a glutaraldehyde solution having a concentration of glutaraldehyde of less than 1%.

In an exemplary embodiment of a method of processing a tissue of the present disclosure, the method further comprising the step of storing the fixed sample in a storage solution. In another embodiment, fixative has a different fixative concentration than the storage solution. In yet another embodiment, the fixing step is performed using a fixative that is buffered. In an additional embodiment, the fixing step is performed using a fixative having a pH of between about 7.2 and about 7.6. In yet an additional embodiment, the fixing step is performed so that the sample of pulmonary region tissue contacts the fixative for at least about 24 hours.

In an exemplary embodiment of a method of processing a tissue of the present disclosure, the storage solution a glutaraldehyde solution having a concentration of glutaraldehyde of or about 0.5%. In another embodiment, the fixing step is performed within a tray lined with a silicone elastomer and by pinning the sample of pulmonary region tissue to the silicone elastomer. In yet another embodiment, the fixing step is performed using bovine serum albumin. In an additional embodiment, the method further comprises the step of removing the fixative from the fixed sample, and placing the fixed sample in a solution comprising at least one item selected from the group consisting of saline, a preservative, bovine serum albumin, and liquid nitrogen.

In an exemplary embodiment of a method of processing a tissue of the present disclosure, the method further comprises the step of decellularizing at least a portion of the sample of pulmonary region tissue prior to performing the fixing step. In an additional embodiment, the method further comprises the step of sterilizing the at least a portion of the sample of pulmonary region tissue prior to performing the fixing step. In an additional embodiment, method further comprises the step of sterilizing the fixed sample.

In an exemplary embodiment of a method of processing a tissue of the present disclosure, the method further comprises the step of treating a patient using the fixed sample. In an additional embodiment, the method further comprises the step of treating a patient using the product. In yet an additional embodiment, the fixed sample is acellular. In another embodiment, the product is configured for use in connection with transcatheter aortic-valve implantation. In yet another embodiment, the product is configured for percutaneous or surgical implantation.

In an exemplary embodiment of a method of processing a tissue of the present disclosure, the product is configured for use to replace a valve selected from the group consisting of an aortic valve, a mitral valve, a pulmonary valve, a tricuspid valve, and a percutaneous valve. In another embodiment, the fixed sample has a thickness that is smaller than a thickness of pulmonary tissue. In yet another embodiment, the product has an overall bulk that is smaller than a bulk of a corresponding product made using fixed pericardial tissue instead of using the fixed sample. In an additional embodiment, the fixed visceral pleura product contains at least one valve leaflet, wherein a non-mesothelial side of the fixed visceral pleura sample is on a relative front of the at least one valve leaflet, and wherein a mesothelial side of the fixed visceral pleura sample is on a relative back of the at least one leaflet.

In an exemplary embodiment of a method of processing a tissue of the present disclosure, the fixed sample has a circumferential axis corresponding to a circumferential axis of the at least a portion of pulmonary region tissue, wherein the fixed sample has an axial axis corresponding to an axial axis of the at least a portion of pulmonary region tissue. In an additional embodiment, the fixed sample can stretch in a direction of the circumferential axis of the fixed sample a first distance, and wherein the fixed sample can stretch in a direction of the axial axis of the fixed sample a second distance, the second distance being less than the first distance. In an additional embodiment, the method further comprises the step of forming the fixed sample into a product configured for mammalian treatment or therapy, wherein the fixed sample is oriented so that the circumferential axis of the fixed sample is aligned within an axial axis of the product, the axial axis being perpendicular to a circumferential axis of a luminal organ to receive the product.

In an exemplary embodiment of a method of processing a tissue of the present disclosure, the method comprises the steps of acquiring at least a portion of a pulmonary region tissue from a mammal, selecting a sample of pulmonary region tissue from the at least a portion of a pulmonary region tissue, and forming the sample of pulmonary region tissue into a tissue product configured for mammalian treatment or therapy. In another embodiment, the step of selecting a sample of pulmonary region tissue comprises selecting a sample of pulmonary ligament tissue from the mammalian tissue. In yet another embodiment, the step of selecting a sample of pulmonary region tissue comprises selecting a sample of visceral pleura tissue from the mammalian tissue.

In an exemplary embodiment of a processed tissue of the present disclosure, the processed tissue is obtained by acquiring at least a portion of a pulmonary region tissue from a mammal, selecting a sample of pulmonary region tissue from the at least a portion of a pulmonary region tissue, and fixing the sample of pulmonary region tissue using a fixative, resulting in a fixed sample.

In an exemplary embodiment of a processed pulmonary region tissue of the present disclosure, the pulmonary region tissue is obtained by fixing a sample of pulmonary region tissue using a fixative, the sample of pulmonary region tissue selected from a larger quantity of pulmonary region tissue harvested from a mammal. In an additional embodiment, the sample of pulmonary region tissue comprises pulmonary ligament. In yet an additional embodiment, the sample of pulmonary region tissue comprises visceral pleura.

In an exemplary embodiment of a processed pulmonary region tissue product of the present disclosure, the pulmonary region tissue product is obtained by forming a sample of pulmonary region tissue fixed using a fixative into a pulmonary region tissue product, the sample of pulmonary region tissue selected from a larger quantity of pulmonary region tissue harvested from a mammal, wherein the pulmonary region tissue product is configured for mammalian treatment or therapy. In another embodiment, the sample of pulmonary region tissue comprises pulmonary ligament. In yet another embodiment, the sample of pulmonary region tissue comprises visceral pleura.

In an exemplary embodiment of a product of the present disclosure, the product comprises a frame configured to retain a mammalian tissue thereon, and the mammalian tissue coupled to the frame, wherein when the product is positioned within a mammalian luminal organ, fluid native to the mammalian luminal organ may pass through a lumen defined within the product. In another embodiment, the frame comprises at least one superior arm and at least one inferior arm positioned at or near an inlet portion of the product, the at least one superior arm and the at least one inferior arm configured to receive a first portion of the mammalian tissue thereon. In yet another embodiment, the at least one superior arm and the at least one inferior arm is configured to receive the first portion of the mammalian tissue thereon and to retain said mammalian tissue using one or more sutures. In an additional embodiment, the frame further comprises at least one connection portion coupled to at least one of the at least one superior arm and/or the at least one inferior arm, the at least one connection portion extending along a longitudinal axis of the device and configured to receive a second portion of the mammalian tissue thereon.

In an exemplary embodiment of a product of the present disclosure, the connection portion is configured to receive the second portion of the mammalian tissue thereon and to retain said mammalian tissue using one or more sutures. In an additional embodiment, the product is configured as a bileaflet frame. In yet an additional embodiment, the product is configured as a trileaflet frame. In another embodiment, the mammalian tissue is sized and shaped to substantially or completely conform to an outer perimeter of the frame. In yet another embodiment, the frame further comprises at least one vertical bar coupled to at least one of the at least one superior arm and/or the at least one inferior arm.

In an exemplary embodiment of a product of the present disclosure, the frame further comprises at least one lower arm coupled to at least one of the at least connection portion and the at least one vertical arm. In another embodiment, the frame is configured to move from a first, closed configuration to a second, open configuration. In yet another embodiment, wherein when the frame is in the first, closed configuration, the product is configured for percutaneous passage through the mammalian luminal organ. In an additional embodiment, the product is configured as a stent valve. In yet an additional embodiment, the stent valve is configured for use as a venous valve.

In an exemplary embodiment of a product of the present disclosure, the fluid native to the mammalian luminal organ passes through an inlet portion of the product and exits from an outlet portion of the product when the product is positioned within the mammalian luminal organ. In an additional embodiment, the mammalian tissue coupled to the frame operates as a valve. In yet an additional embodiment, the fluid native to the mammalian luminal organ is at least partially prevented from flowing from the outlet portion to the inlet portion when the product is positioned within the mammalian luminal organ. In another embodiment, the mammalian tissue comprises mammalian pulmonary ligament. In yet another embodiment, the mammalian tissue comprises mammalian pulmonary viscera.

In an exemplary embodiment of a product of the present disclosure, the mammalian tissue comprises tissue having stretchability and durability properties to allow the mammalian tissue to move relative to fluid flow through the lumen defined within the product. In another embodiment, the mammalian tissue is fixed. In yet another embodiment, the mammalian tissue is fixed using glutaraldehyde. In an additional embodiment, the frame is capable of expansion using a balloon catheter. In yet an additional embodiment, the frame is autoexpandable.

In an exemplary embodiment of a product of the present disclosure, the frame comprises a material selected from the group consisting of nitinol, chromium, cadmium, molybdenum, nickel, a nickel composite, nickel-cadmium nickel-chromium, nitinol palladium, palladium, cobalt, platinum, and stainless steel.

In an exemplary embodiment of a method of the present disclosure, the method comprises the steps of shaping an mammalian tissue so that the mammalian tissue will fit around portions of a frame, the mammalian tissue excised from a mammalian body, positioning the mammalian tissue around a mount, positioning at least part of a frame around the mammalian tissue positioned around the mount, and connecting the mammalian tissue to the at least part of the frame to form the product. In another embodiment, the method further comprises the step of processing the excised mammalian tissue prior to the shaping step. In yet another embodiment, the processing step is performed by excising the mammalian tissue from the mammalian body, removing any undesirable portions of the excised mammalian tissue, placing the excised mammalian tissue on a frame, and fixing the tissue using a fixative. In an additional embodiment, the shaping step is performed by stretching the mammalian tissue and cutting the mammalian tissue to form a desired shape.

In an exemplary embodiment of a method of the present disclosure, the connection step is performed by positioning at least part of the mammalian tissue around the at least part of the frame. In another embodiment, the connection step is performed by positioning at least part of the mammalian tissue around one or more of a superior arm, an inferior arm, and a connection portion of the frame. In yet another embodiment, the connection step is further performed by suturing at least part of the mammalian tissue around the at least part of the frame. In an additional embodiment, the connection step is performed by positioning at least part of the mammalian tissue around the at least part of the frame so that at least part of the mammalian tissue operates as one or more valve leaflets. In yet an additional embodiment, the mammalian tissue comprises pulmonary ligament. In an exemplary embodiment of a method of the present disclosure, the mammalian tissue comprises visceral pleura.

In an exemplary embodiment of a method of processing a tissue of the present disclosure, the method comprises the steps of acquiring a sample of pulmonary region tissue from a mammal, and fixing the sample of pulmonary region tissue using a fixative, resulting in a fixed sample. In another embodiment, the step of acquiring a sample of pulmonary region tissue comprises selecting a sample of pulmonary ligament tissue from the mammal. In yet another embodiment, the step of selecting a sample of pulmonary region tissue comprises selecting a sample of visceral pleura tissue from the mammal.

In an exemplary embodiment of a processed pulmonary ligament of the present disclosure, the processed pulmonary ligament is prepared by fixing a sample of pulmonary region tissue acquired from a mammal using a fixative, resulting in a fixed sample.

In an exemplary embodiment of a method of the present disclosure, the method comprises the step of fixing a sample of pulmonary region tissue acquired from a mammal using a fixative, resulting in a fixed sample In an exemplary embodiment of a method for preparing a tissue material of the present disclosure, the method comprises the step of decellularizing a segment of pulmonary region tissue. In another embodiment, the method further comprises the step of: sterilizing the pulmonary region tissue. In yet another embodiment, the method further comprises the step of fixing the pulmonary region tissue. In an additional embodiment, the pulmonary region tissue comprises pulmonary ligament tissue. In yet an additional embodiment, the pulmonary region tissue comprises visceral pleura tissue.

In an exemplary embodiment of a medical article of manufacture, the medical article of manufacture comprises acellular pulmonary region tissue sterilely enclosed within packaging. In another embodiment, the pulmonary region tissue is chemically fixed. In yet another embodiment, the pulmonary region tissue is not chemically fixed. In an additional embodiment, the pulmonary region tissue comprises pulmonary ligament tissue. In yet an additional embodiment, the pulmonary region tissue comprises visceral pleura tissue.

In an exemplary embodiment of a method for treating a patient of the present disclosure, the method comprises the step of introducing into a patient a medical device including pulmonary region tissue. In another embodiment, the tissue is acellular. In yet another embodiment, the pulmonary region tissue comprises pulmonary ligament tissue. In an additional embodiment, the pulmonary region tissue comprises visceral pleura tissue.

In an exemplary embodiment of a method of processing a tissue of the present disclosure, the method comprises the steps of acquiring at least a portion of a pulmonary region tissue from a mammal, selecting a sample of pulmonary region tissue from the at least a portion of a pulmonary region tissue, and fixing the sample of pulmonary region tissue using a fixative, resulting in a fixed sample.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 10A shows a portion of a mammalian tissue cut/shaped to fit along a trileaflet frame, according to an exemplary embodiment of the present disclosure;

FIG. 10B shows an exemplary product having a trileaflet frame and a tissue positioned thereon, according to an exemplary embodiment of the present disclosure;

FIG. 10C shows an exemplary product configured as a valve and positioned within a mammalian luminal organ, according to an exemplary embodiment of the present disclosure.

Figure 1A:
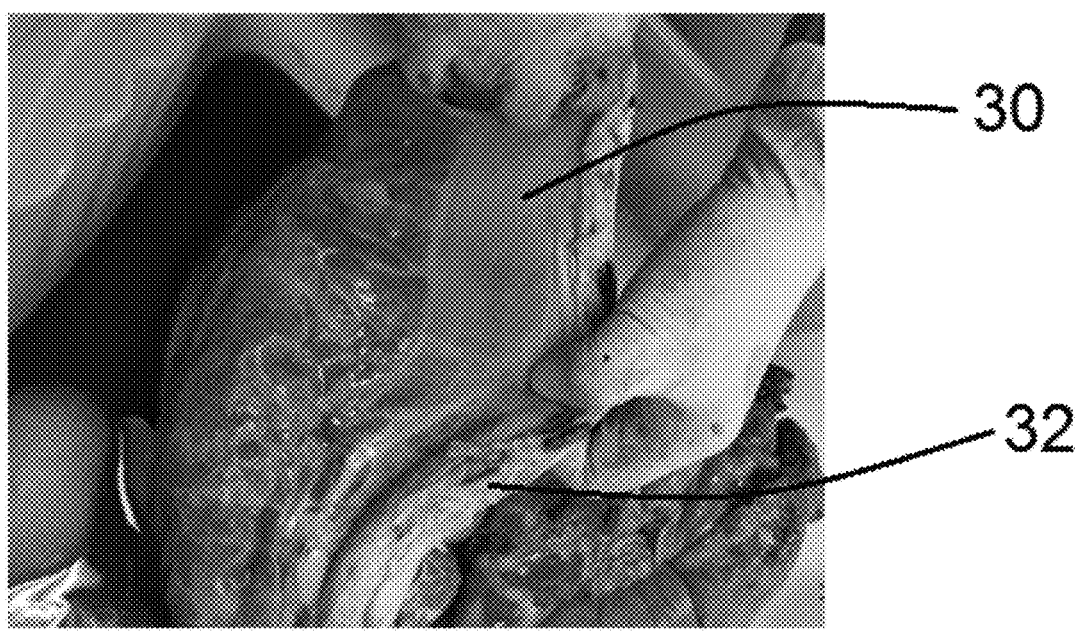
FIGS. 1A and 1B show a swine pulmonary ligament connected to a lung, according to exemplary embodiments of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure contains disclosure of novel methods and uses for harvesting and applying certain mammalian tissue for use in connection with various medical applications. The mammalian pulmonary ligament and the mammalian visceral pleura, as referenced in detail below and disclosed within the present application, can be harvested, fixed, and used for a number of medical applications previously unknown and not identified in the medical arts. In at least one embodiment of the present disclosure, pulmonary ligament tissue is identified, harvested, fixed, and ultimately used in connection with mammalian treatment/therapy. As referenced herein, pulmonary ligament and visceral pleura are both "pulmonary region" tissue.

As referenced in detail herein, it is advantageous to identify and process thin scaffold biological tissue that consists of largely elastin and some collagen fibers (the converse of SIS), since elastin is not as prone to fixation as collagen fibers. Hence, fixation of tissue with elastin largely maintains its elasticity and hence biological mechanical activity. Furthermore, it is advantageous to identify a thin membraneous native tissue that does not require any processing, such as stripping of muscle or treatment with antibiotics given the bacteria flora such as present within the intestines. Finally, there is significant advantage to tissue that has epithelial layers on both sides of the tissue. As referenced in detail herein, the present disclosure includes uses and methods in connection with such a biological tissue and processing steps for various biological applications.

The visceral pleura that covers the lung extends to the hilum where it becomes continuous with the parietal pleura that covers the diaphragm, chest wall, and mediastinum. As the anterior and posterior pleural extend below the pulmonary veins, the two layers of pleura come together to form the inferior pulmonary ligament. Hence, the pulmonary ligament is a double layer of pleura that drapes caudally from the lung root and loosely tethers the medial aspect of the lower lobe of the lung to the mediastinum. However, and importantly, the pulmonary ligament does not functionally behave the same as two layers of pleura, as the non-isotropy of pulmonary ligament tissue is notably different than just two layers of pleura. Furthermore, the degree of collagen within pulmonary ligament is also different than in two layers of pleura, and the function of pulmonary ligament is also different, as pulmonary ligament tissue resists load in one direction. The pulmonary ligament tethers the lung and has substantial elasticity (over 200% extension, which may be a lateral extension) to expand with each inflation of the lung. The significant elasticity stems from the high elastin content. Contrary to collagen, elastin cannot be fixed and largely retains its elasticity post fixation. As such, and as described above and otherwise herein, the novel nature of identifying, harvesting, fixing, and using processed lung ligament tissue can result in numerous therapies and treatments not previously considered or used in the medical arts.

In certain embodiments of processed pulmonary ligament 50 and/or processed visceral pleura 60 of the present disclosure, said tissues can have a microarchitecture including non-randomly oriented collagen and elastin fibers, which can be retained from the native microarchitecture of the processed pulmonary ligament 50 and/or processed visceral pleura 60, and/or the processed pulmonary ligament 50 and/or processed visceral pleura 60 can exhibit an anisotropic elastic character, for example as can be demonstrated in biaxial stretch testing and/or through optical and/or microscopic visualization of the tissue microstructure. As well, in these and other embodiments, processed pulmonary ligament 50 tissue can have a thickness of about 80 microns to about 100 or 120 microns, and even as high as about 300 microns, including thicknesses between about 90 microns and 100 microns, which depends upon the species from which the pulmonary ligament tissue is obtained. Processed visceral pleura 60 may have a smaller thickness, such as between about 40 microns and about 80 microns, as referenced further herein. Other embodiments of processed pulmonary ligament 50 and/or processed visceral pleura 60 of the present disclosure may be up to 300 microns in thickness. In an actual exemplary sample of 15 harvested processed pulmonary ligament samples obtained according to the present disclosure, the average thickness was 102 microns, and the thickness range was from 22 microns to 269 microns. Different thicknesses of tissue may be preferred for different embodiments, such as relatively thinner tissues for valve applications, and relatively thicker tissues for hernia repair, for example.

For various pulmonary ligament 30 and/or visceral pleura 556 samples, a predominant proportion of the collagen fibers in the tissue are oriented generally in a first direction, with that direction having extended substantially parallel to the median (or midsagittal) plane of the animal from which the tissue was harvested. For example, and in at least one embodiment, at least 75% of collagen fibers within the harvested pulmonary ligament 30 and/or visceral pleura 556 tissue are oriented in a first direction. In at least another embodiment, at least 60% of collagen fibers within the harvested pulmonary ligament 30 and/or visceral pleura 556 tissue are oriented in a first direction. Furthermore, and in various pulmonary ligament 30 and/or visceral pleura 556 samples, said tissues include elastin fibers that extend in a direction transverse to that of the predominating collagen fibers contained therein.

Figure 1B:
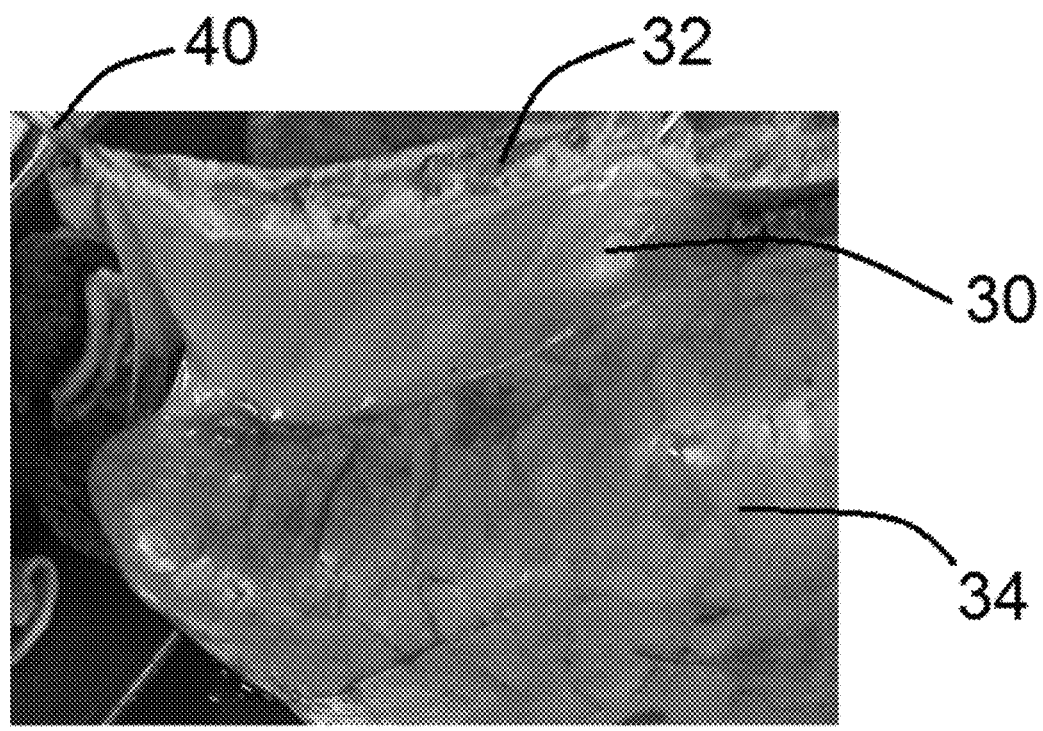

FIGS. 1A and 1B pictorially show a swine pulmonary ligament (an exemplary ligament 30) by way of gripping a portion of the pig (such as by the aorta and/or esophagus (collectively shown as 32 in FIG. 1A) or tissue in that general vicinity) and pulling the same away from the lung 34, as shown in FIG. 1B. Gripping and/or separation of tissue can be performed by hand, as shown in FIG. 1A, and/or by using forceps 40, as shown in FIG. 1B. The pulmonary ligament 30 is clearly shown and identified in FIGS. 1A and B.

Figure 2A:
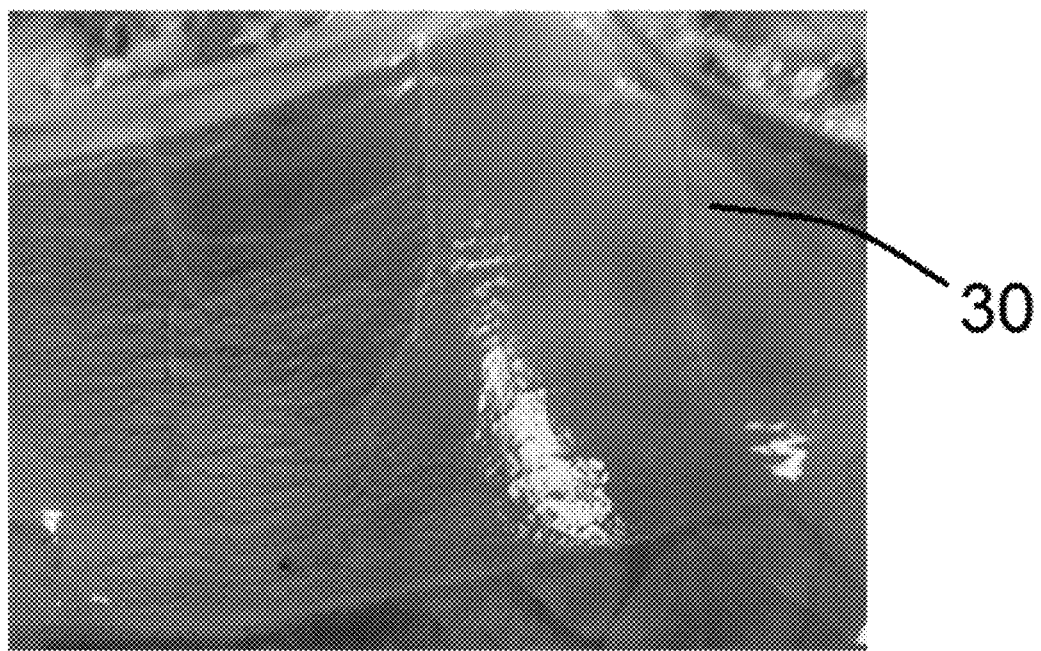
FIG. 2A shows a close-up view of a swine pulmonary ligament, according to an exemplary embodiment of the present disclosure.
Figure 2B:
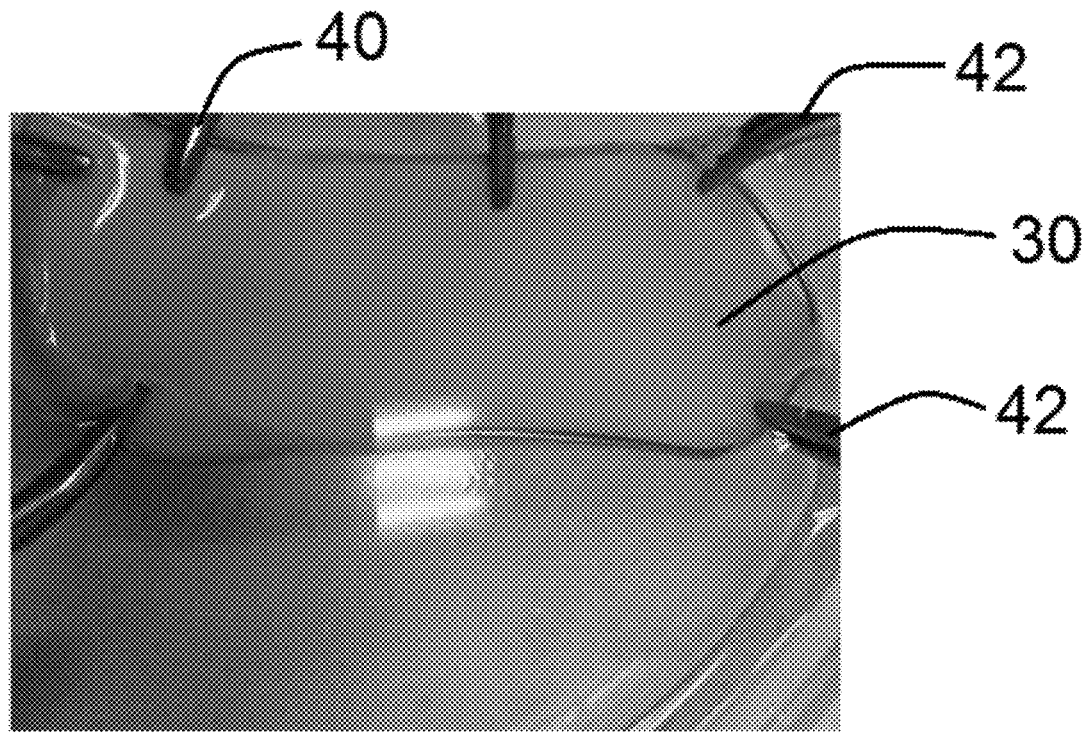
FIG. 2B shows a portion of a pulmonary ligament held in place upon a frame, according to an exemplary embodiment of the present disclosure.
Figure 3A:
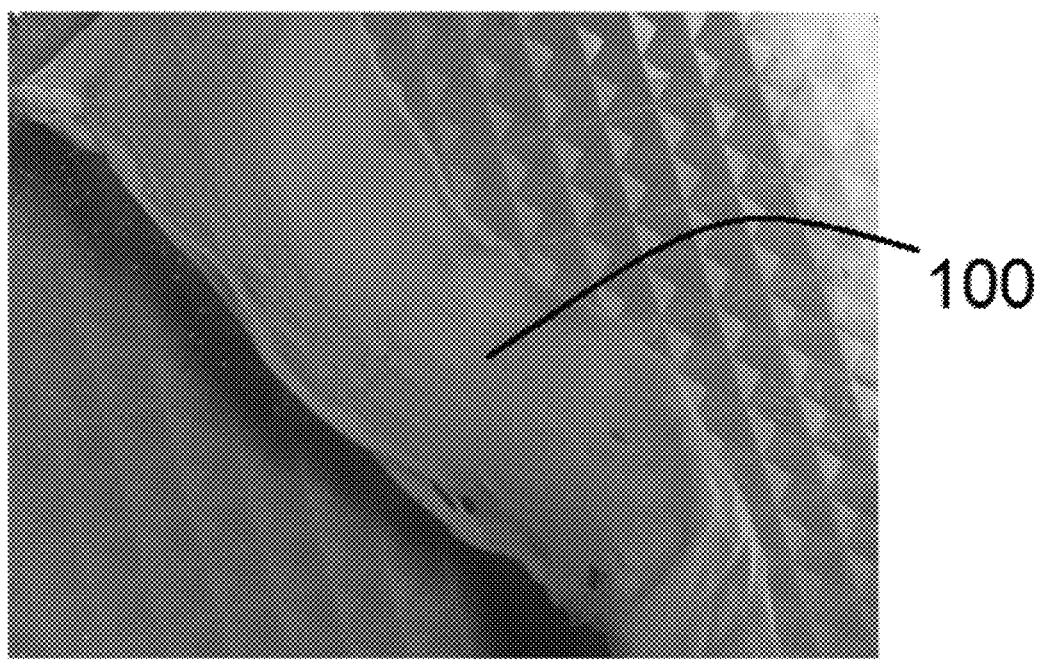
FIGS. 3A and 3B show a fixed product, according to exemplary embodiments of the present disclosure.
Figure 3B:
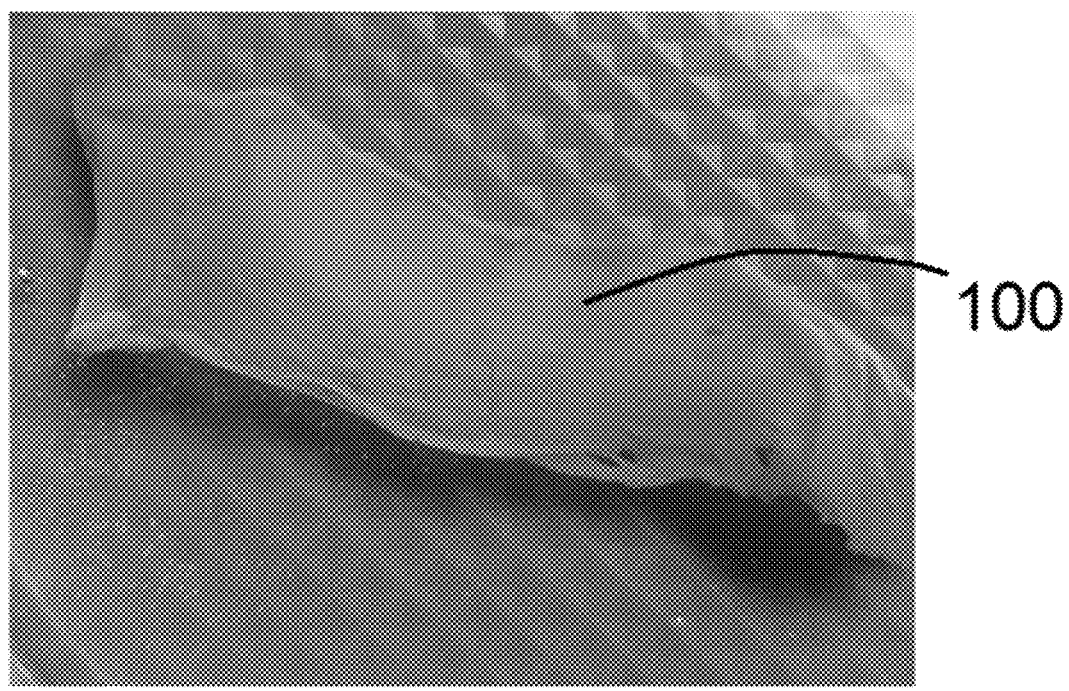

FIG. 2A shows a closer view of a portion of the pulmonary ligament 30, and FIG. 2B shows a portion of the pulmonary ligament 30 held in place using a series of clamps 42 positioned around a mount 44, for example, and being fixed with a fixative, such as glutaraldehyde. Post fixation pulmonary ligament (which could also be referred to as a processed ligament 50 of the present disclosure, potentially configured as an exemplary product 100 of the present disclosure as referenced below), as shown in FIGS. 3A and 3B, has high elasticity, and both sides of the ligament tissue are smooth and covered with an epithelial layer that secretes a lubricant.

Figure 4A:
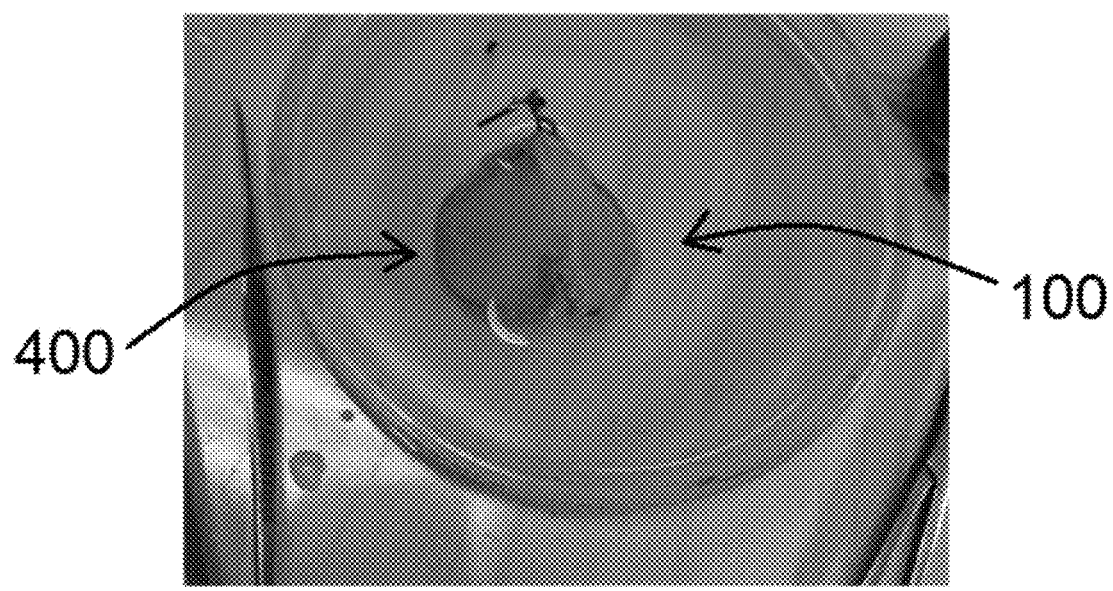
FIGS. 4A-4D show various depictions of a portion of a pulmonary ligament, after fixation, formed into an exemplary constructed valve according to exemplary embodiments of the present disclosure.
Figure 4B:
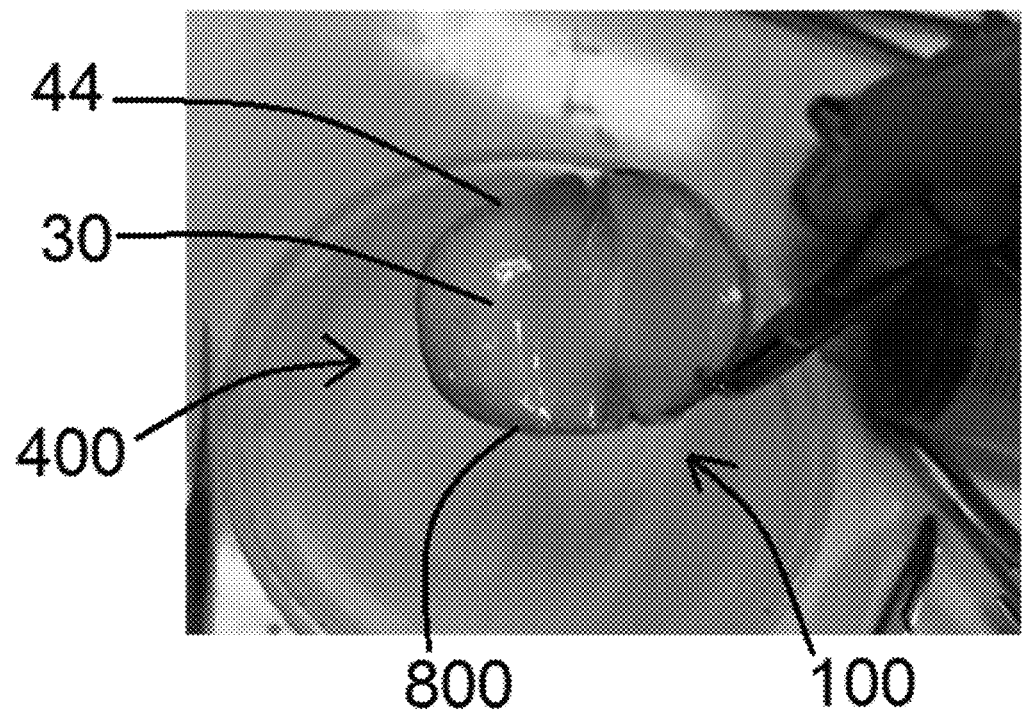
Figure 4C:
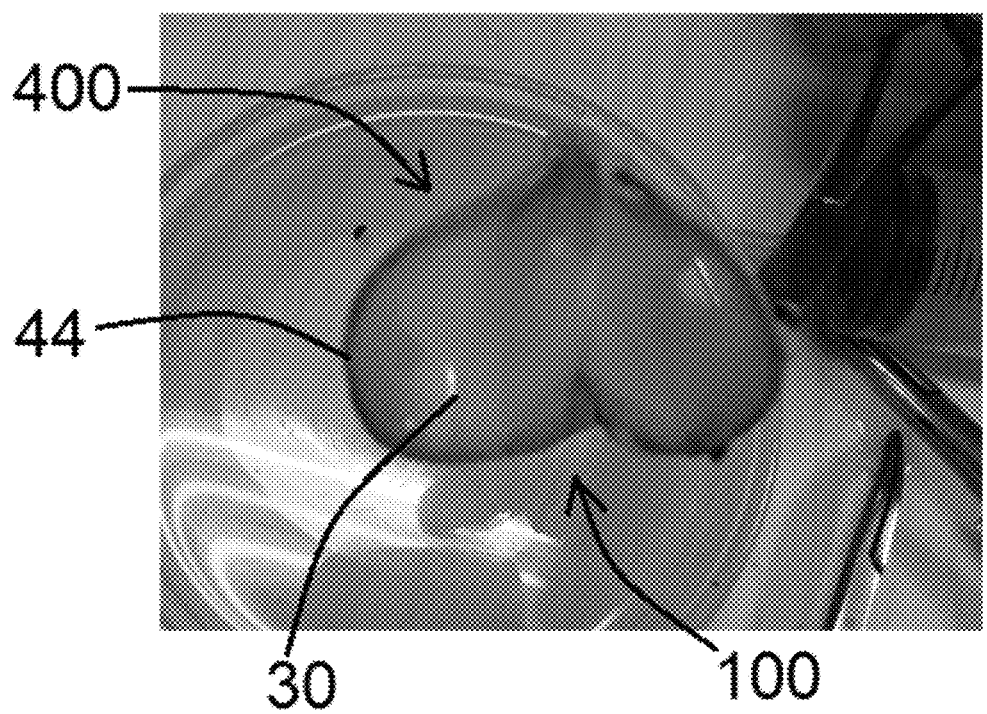
Figure 4D:
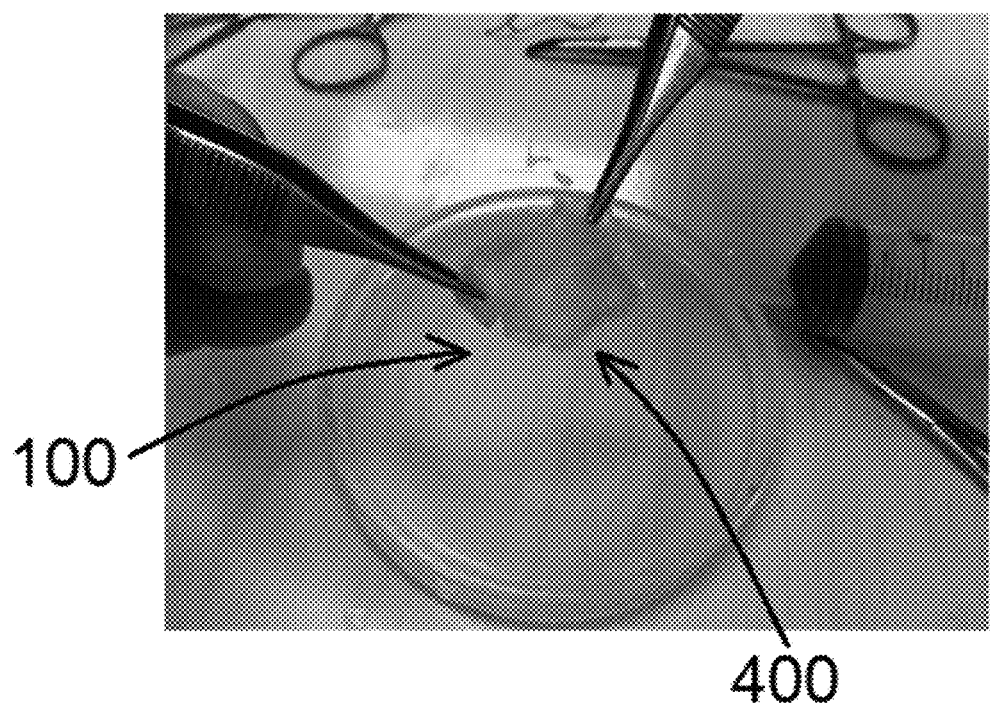

FIGS. 4A-4D show various depictions of a portion of a porcine pulmonary ligament 30, after glutaraldehyde fixation (to form processed ligament 50 and potentially an exemplary product 100), and formed into an exemplary constructed valve 400 of the present disclosure. For example, and as shown in FIGS. 2B and 4A-4C, pulmonary ligament 30 can be placed upon a mount 44, using one or more forceps 40 and/or clamps 42 (as shown in FIG. 2B), and/or one or more sutures 800 (as shown in FIG. 4B in connection with use of a mount 44, and as described in further detail herein in connection with one or more frames 600 of the present disclosure). Placement may also include folding portions of pulmonary ligament 30 around portions of mount 44, as shown by way of folded portion 48 in FIG. 4C. If one or more sutures 800 are used, said sutures 800 could comprise nylon or another suitable material, and could be placed using a needle (not shown), as described in further detail herein.

As shown in the various figures, the valve 400 (comprising pulmonary ligament in the embodiment shown), which is an exemplary processed product 100 of the present disclosure, easily flexes and maintains its shape. Products 100 can include processed ligament 50 or processed visceral pleura 60, as referenced in further detail herein, and may also be referred to herein as medical articles of manufacture. As referenced herein, pulmonary ligament 30 refers to pulmonary ligament tissue that has not yet been processed, and processed ligament 50, optionally configured as one or more processed products 100 of the present disclosure, refers to tissue that has been processed, such as by fixation, and optionally configured as products 100. Similarly, and as also referenced herein, visceral pleura 556 refers to visceral pleura tissue that has not yet been processed, and processed visceral pleura 60, optionally configured as one or more processed products 100 of the present disclosure, refers to tissue that has been processed, such as by fixation, and optionally configured as products 100. Various valves 400 of the present disclosure may comprises any number of valves, including, but not limited to, aortic valves, mitral valves, pulmonary valves, tricuspid valves, and/or other percutaneous valves.

Figure 5A:
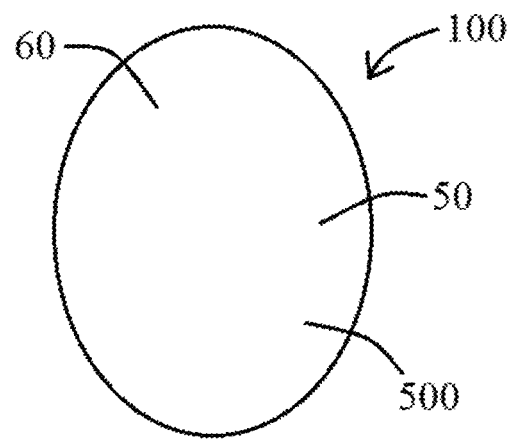
FIGS. 5A-5D show various processed lung ligament products in various configurations, according to exemplary embodiments of the present disclosure.
Figure 5B:
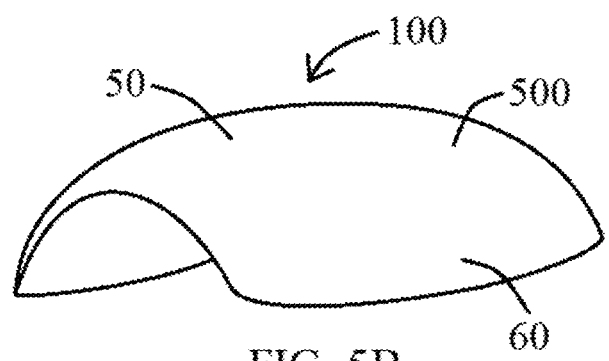
Figure 5C:
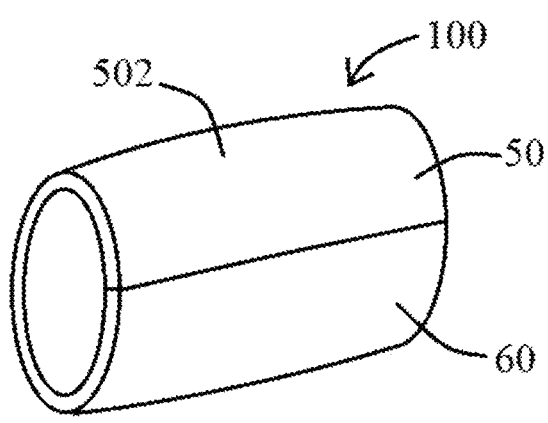
Figure 5D:
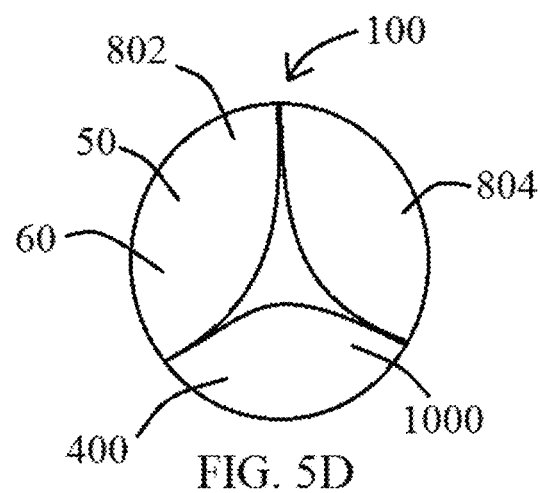

FIGS. 5A-5D show various processed products 100 in various configurations, according to exemplary embodiments of the present disclosure. For example, FIG. 5A shows an exemplary product 100 of the present disclosure configured as a patch, membrane, tissue replacement, cover, or reinforcement. Said embodiments (patch, membrane, tissue replacement, cover, or reinforcement) shall be referred to generally as patches 500, as labeled in FIG. 5A. FIG. 5B shows another exemplary product 100 of the present disclosure configured as a curved patch, membrane, tissue replacement, cover, or reinforcement (collectively curved patches 500). FIG. 5C shows an exemplary product 100 configured as a tube 502, and FIG. 5D shows an exemplary product 100 configured as a valve 400. Valve 400, as shown in FIG. 5D, is configured as a tri-leaflet valve 400 (including, for example, leaflets 802, 804, and 1000, as referenced in further detail herein), but other valve 400 embodiments of the present disclosure may be single leaflet valves 400, bileaflet valves 400, or valves 400 with more than three leaflets. In each embodiment shown therein, products 100 comprise one or more processed ligaments 50 and/or one or more processed visceral pleura 60.

Other product 100 configurations are contemplated by the present disclosure, as various biological uses of products 100 can be had, and the present disclosure is not limited to the configurations shown in the figures. For example, a venous stent cover (an exemplary cover 502) with a membrane and valve 400 included is an exemplary product 100 of the present disclosure, with features shown in one or more figures referenced herein, such as FIGS. 5B, 5C, and 5D. For example, a product 100 of the present disclosure could have an external shape shown in FIG. 5C and a valve 400 as shown in FIG. 5D.

As for preparation of all or a portion of a pulmonary ligament 30 or a visceral pleura 556, it is known that biological tissues are pre-stretched or otherwise pre-stressed in vivo for optimal function. For an exemplary embodiment of this particular tissue, the degree of pre-stretch was determined, in at least one method, by measuring the dimensions of the tissue before and after harvest. This was accomplished in this particular example by placing various dots/markings (such as dots/markings 575 shown in FIG. 5F) on the ligament 30 and/or visceral pleura 556 itself in its in vivo state to determine the degree of stretch in the two principle directions (referred to herein as the x and y directions). Using such a method, one can characterize that the tissue shrinks by X and Y amount in the x and y directions.

In the glutaraldehyde (or other chemical/mechanism) fixation and mounting process of the tissue on mounts 44 or frames (for stents and other uses as referenced herein), the tissue can be pre-stretched by X and Y to the in vivo values to ensure optimal function of the tissue. In addition, fiber lengths and/or desmosine contents could be measured/obtained in connection with various steps of fixation, including but not limited to determining an amount of tissue shrinkage due to fixation. For example, a stress-strain relation could be determined in fresh lung ligament 30 tissue and processed lung ligament 50 tissue, and a fixed strain could be selected that corresponds to the stress in fresh tissue, for example. Similar stress-strain relations could also be determined in fresh visceral pleura 556 tissue and processed visceral pleura 60 tissue. Furthermore, optical means of selection, such as with the use of traditional light, polarized light, and/or other light, with and without magnification, could be used to optically scan the various harvested tissues.

An example pulmonary ligament 30 and/or visceral pleura 556 harvesting procedure is described as follows. In at least one method, the heart/lung block can be extracted from a mammal (such as in connection with a meat processing facility), and the extracted tissue could then be placed in a relatively cold saline solution to help preserve the same. The heart/lung block may be generally referred to herein a pulmonary region tissue, which may include, but is not limited to, lung tissue and one or more of the bronchi, pulmonary artery, pulmonary vein, and/or the heart, so long as the desired tissue to be harvested (pulmonary ligament 30 and/or visceral pleura 556) is contained therein. At or before the time of processing, the tissue can be inspected for blood infiltration, fatty material, perforations, and/or other irregularities, and portions of the tissue containing the same can be treated to either removed the undesired components or discarded/disregarded in view of other portions of the tissue that are relatively homogenous and free of undesired properties, such as perforations or fat.

After selection of desired portions of pulmonary ligament 30 and/or visceral pleura 556 from the overall resected tissue, the selected membranes can be mounted in mounts 44 (such as available circular or rectangular frame mounts) to prevent shrinkage and/or folding during fixation, and can be submerged in a fixation solution (such as glutaraldehyde, for example) for fixation. Prior to mounting and/or fixation, or after mounting and/or fixation if desired, the pulmonary ligament 30 and/or visceral pleura 556 can be pre-seeded to make it more likely to endothelialize. As pulmonary ligament tissue has mesothelium on both sides and visceral pleura has mesothelium on only one side, pre-seeding (also referred to as endothelial seeding) could be performed on the non-mesothalial side of the tissue. After fixation, a relatively flat piece of fixed tissue will result. Using another method, and after selection of the membranes or desired portions thereof, the membranes can be placed on multidimensional molds, for example, allowing the user to stretch and/or otherwise fit the membrane so to mimic the mold shape, and then fix the membrane on the mold. With such a method, the resultant fixed material will maintain or closely resemble to multidimensional shape of the mold, and can be used for various purposes.

Various sizes and/or thicknesses of processed lung ligament 50 and/or processed visceral pleura 60 tissues could be used and be tailored to specific applications. For example, and in embodiments of processed lung ligament 50 and/or processed visceral pleura 60 tissue ultimately used as valves 400 (exemplary products 100 of the present disclosure), lung ligament 50 tissue of between about 80 microns and about 100 microns to about 300 microns could be used, while visceral pleura 60 between about 40 microns and about 80 microns could be used.

With respect to initial tissue harvesting of visceral pleura 556 tissue, an exemplary method of the present disclosure includes the step of isolating tissue 556 from the middle-anterior portion of the lungs, 34 which tends to be relatively thicker and more uniform than other portions of the lung 34. A lateral incision can be made, and using forceps 40 for example, the lung 34 tissue can be carefully pressed away from the visceral pleura 556. FIG. 5F shows a diagram of a portion of a mammalian body 550 showing the lungs 34 and an identified harvest section 552, generally comprising the middle-anterior portion of the lungs 34. Two portions of tissue are shown, namely the parietal pleura 554 that lines the chest cavity and the visceral pleura 556 which lines the lungs 34 and is internal to the parietal pleura 554. As shown in FIG. 5F, and referenced in further detail herein the mesothelial side 860 of visceral pleura 556 is on a relative outside of the lung 34, while the non-mesothelial side 862 of visceral pleura 556 is on the relative inside of the lung 34. Pulmonary region tissue 558 is also shown therein, which may include, but is not limited to, lung tissue and one or more of the bronchi, pulmonary artery, pulmonary vein, and/or the heart, as previously referenced herein. The acquired pulmonary ligament 30 and/or visceral pleura 556 from said pulmonary region tissue may be referred to herein as "samples" of tissue from the pulmonary region tissue 558. After an initial portion of visceral pleura 556 tissue (such as ~0.5 cm or so) has been separated, the tissue can be gently worked away (manually using one's hand/fingers, for example), taking care/precautions not to overly stress or pull on the visceral pleura 556 tissue. Prior to removal of the visceral pleura 556, the general orientation can be noted and potentially marked on the tissue, noting that visceral pleura 556 has different degrees of potential stretch depending on orientation.

FIG. 5F also demonstrates an exemplary harvesting method whereby pulmonary ligament 30 and/or visceral pleura 556 tissue is harvested and ultimately used in a desired orientation based upon an orientation of harvest. As shown in FIG. 5F, the x-axis (identified as "X" in the figure)

may also be referred to herein as a "circumferential" or "transverse" axis or direction/orientation of tissue, and the y-axis (identified as "Y" in the figure) may also be referred to herein as a "vertical" or "axial" axis or direction/orientation of tissue. Natural lung expansion and contraction, consistent with breathing, occurs in a fashion whereby pulmonary ligament 30 and/or visceral pleura 556 would stretch more in the circumferential direction as compared to the axial direction, so whereby pulmonary ligament 30 and/or visceral pleura 556 tissue harvested from a mammal would also have more stretchability in the circumferential direction as compared to the axial direction. Phrased differently, the axial direction is notably stiffer than the circumferential direction, which is also referred to herein as being relatively softer than movement/stretch in the axial direction. To leverage the inherent non-isotropy of said tissue(s), and using a specific orientation of the same in connection with one or more products 100 of the present disclosure, including but not limited to valves 400 as referenced herein, the tissue orientation would be identified at the time of harvest and use accordingly in connection with one or more products 100 of the present disclosure. For example, processed pulmonary ligament 50 and/or processed visceral pleura 60 can be oriented on frame 600, as referenced in further detail herein, so that the axial direction of the product 100 in a mammalian luminal organ (such as a blood vessel) is softer than the circumferential/radial direction, in reference to the product 100, as the circumferential direction is, for example, constrained by the diameter of the blood vessel and cannot distend further, while the axial direction is the direction of opening and closing a valve 400 (in a product 100 embodiment configured as a valve), where more deformation would be needed or desired. Leveraging this non-isotropy (directionality) could be used in connection with various products 100 of the present disclosure depending on the application of interest.

Figure 5E:
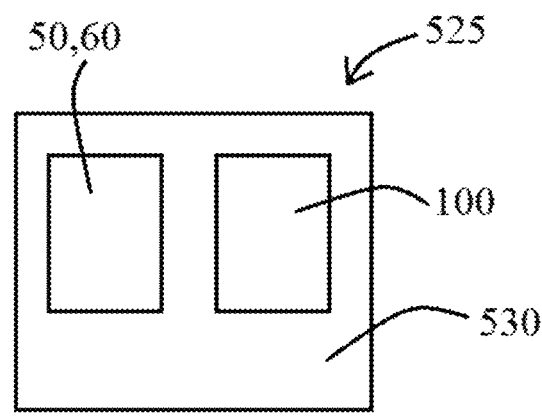
FIG. 5E shows a block diagram of components of a kit, according to an exemplary embodiment of the present disclosure.
Figure 5F:
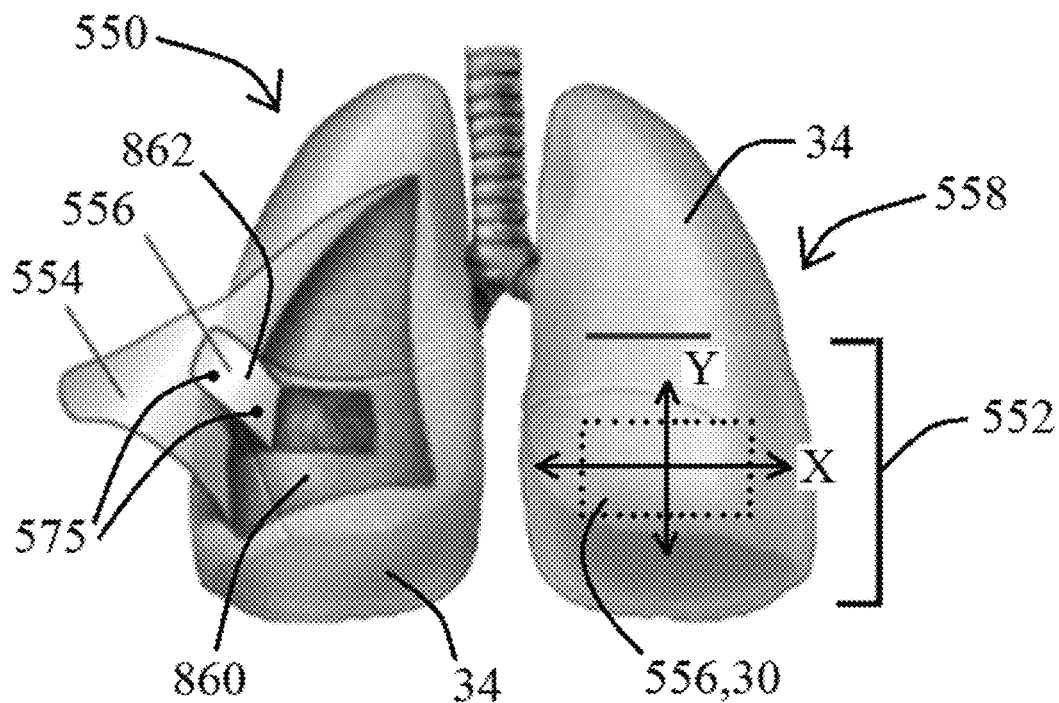
FIGS. 5F and 5G show mammalian tissue and tissue harvest locations, according to exemplary embodiments of the present disclosure.
Figure 5G:
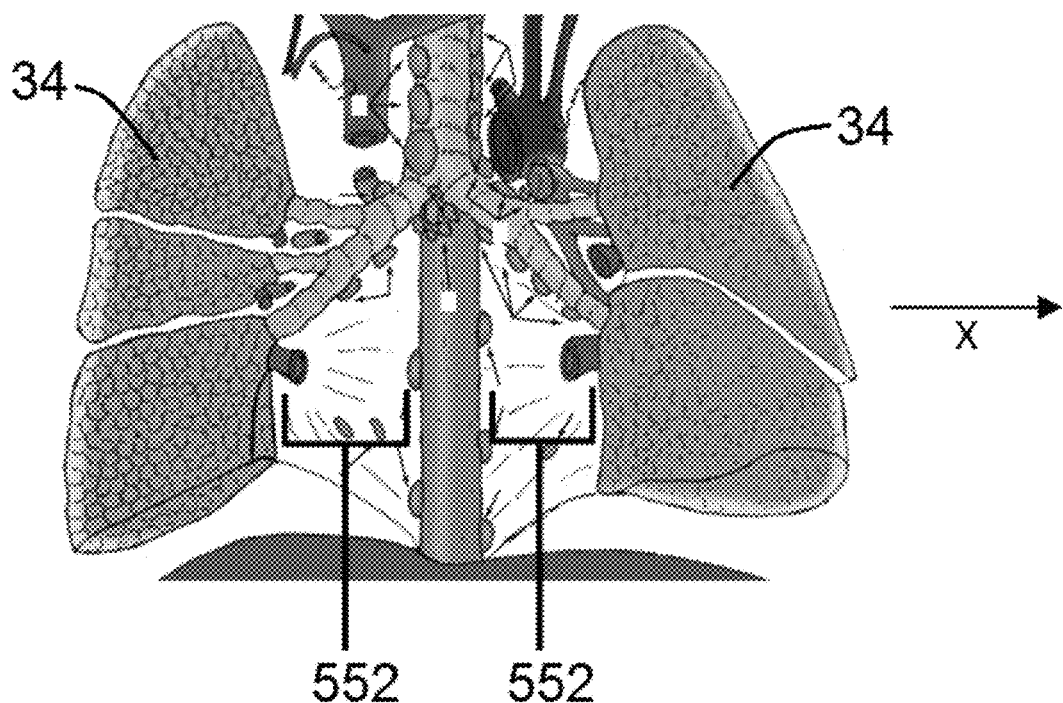

With respect to initial tissue harvesting of pulmonary ligament 30 tissue, an exemplary method of the present disclosure includes the step of isolating tissue 30 from the relative middle section between the lungs 34, as indicated by harvest sections 552 shown in FIG. 5G. The specific harvest section 552 used may depend on mammalian species, the age of the mammal, and/or the thickness of tissue required for a particular application. As with visceral pleura 556 (referenced above and shown in FIG. 5F), pulmonary ligament 30 thickness varies with location within the body. As generally referenced herein, efforts to avoid vascular areas (and/or those areas with blood infiltration), fatty material, perforations, and/or other irregularities should be made to that desirable pulmonary ligament 30 or visceral pleura 556 can be obtained. In addition, and regarding certain pulmonary ligament 30 or visceral pleura 556 tissue, avoiding said tissues near the lungs 34 and/or the aorta/esophagus 32 may also lead to preferable pulmonary ligament 30 or visceral pleura 556 harvest. Similar to visceral pleura 556 harvest, and prior to removal of the pulmonary ligament 30, the general orientation can be noted and potentially marked on the tissue, noting that pulmonary ligament 30 has different degrees of potential stretch depending on orientation, noting that as shown in FIG. 5G, ligament 30 is most elastic in the x-direction as shown in the figure.

Pulmonary ligament 30, as referenced herein, may be generally described as a sheet of tissue, and not generally as a combined/bundled tissue. For example, and upon pulmonary ligament 30 harvest, the sections of pulmonary ligament 30 suitable for harvest are generally continuous with the aorta, and are generally not part of the bundled ligament that descends from the mammalian lung root.

General tissue harvesting can apply to several mammalian species, including, but not limited to, cattle, pigs, and horses, such as from blocks of tissue collected after animal slaughter. Harvesting is preferred using clean/sterile conditions, and can proceed after an initial inspection of the blocks of tissue for portions of suitable tissue not having any malformations, abnormalities, perforations, tears, calcifications, spots, etc., as generally referenced herein. The desired tissue (pulmonary ligament 30 or visceral pleura 556) can be cleaned using a suitable solution (water and/or saline, for example), and fat and/or muscle covering the tissue can be removed, such as with the use of forceps 40. The removed tissue (pulmonary ligament 30 or visceral pleura 556) can be positioned about a mount 44, as described and shown herein, and attached to the same using clamps 42 and/or sutures, such as those comprising Nylon 0, used as overcast stiches, with a needle such as a 333/5 needle. The attachment step can be performed outside of a solution or within a solution, such as a fixative solution. One such fixative solution may comprise 0.65% glutaraldehyde solution BLUE. The dissected tissue can then be stored, upon the mount 44, within an appropriate fixative solution for an appropriate amount of time. For example, and to accomplish initial fixation, the tissue can be fixed in the fixative solution for at or approximately 24 hours, and the solution can be changed (to either the same fresh fixative solution or to another solution) and stored until the tissues are ready to be cut, formed, manipulated, or otherwise used. Keeping the tissue hydrated is important, as should the tissue completely or partially dry out, it would likely irretrievably lose desired mechanical properties. Long term (or relatively long term) storage can be in, for example, 0.65% glutaraldehyde solution BLUE or another solution for an initial period of time, and then changed to a lower concentration solution (such as 0.50% glutaraldehyde solution CELESTE), for example, and stored until needed.

Regarding fixation, an exemplary fixative solution of the present disclosure can be prepared, resulting in a buffered glutaraldehyde solution, can be prepared as follows. In at least one example of a fixative solution, and in less than 1 L of $DDH_2O$), the following can be added: 1) 2.05 h of NaOH, 2) 9.08 g of $PO_4H_2K$, and 3) 13 mL of 50% glutaraldehyde solution (or 26 mL of 25% glutaraldehyde solution). The desired pH would be at or near 7.4 for this exemplary fixative solution, and if the combined solution is not at 7.4, it can be adjusted using additional NaOH solution. After pH adjustment to the desired pH, the overall volume of the flask can be increased to 1.0 L, resulting in the exemplary fixative solution. Other fixative solutions may be optimal for use in connection with various fixation procedures of the present disclosure.

To ultimately fix acquired pulmonary ligament 30 or visceral pleura 556 tissue, at least one fixation method comprises fixing the pulmonary ligament 30 or visceral pleura 556 in a fixation solution for at least 24 hours, and optionally at a reduced temperature (such as at or near 23° C.). Other fixation times and temperatures may be used as well. For long-term storage of fixed tissue, storage in 0.5% glutaraldehyde (for example) can protect the fixed tissue. In at least one embodiment, fixation with minimal to no preload is recommended, as preloading may change the mechanical properties of the tissue during and/or after fixation. To maintain preferred tissue fiber orientation, flat or relatively-flat fixation would be recommended. Flat or relatively-flat fixation can be performed, for example, using a tray lied with a silicone elastomer (such as Sylgard), allowing for the tissue to remain flat or relatively flat when pinned down during the fixation process.

Regarding fixation, glutaraldehyde is widely used, and can be used in connection with various buffers, such as HEPES and phosphate buffers. In at least one method, glutaraldehyde is used around a neutral and slightly alkaline pH at or about 7.4, noting that other pH values or ranges can be used with various fixation methods. For example, and in at least one additional fixation method, formaldehyde (formalin) may be used, and/or glycerol may be used. In an exemplary fixation method using glycerol, at or about 98% glycerol may be used to fix the tissue. In at least one embodiment of a method of fixing pulmonary ligament 30 or visceral pleura 556 tissue, bovine serum albumin (BSA) can be used to remove cytotoxicity in connection with fixation, such as fixation using glutaraldehyde and/or formaldehyde. Eliminating glutaraldehyde and/or formaldehyde from the storage solution may be beneficial as such compositions are quite cytotoxic, and storage of fixed tissue in non-toxic solutions or using dry tissue technologies can be useful to stored said fixed tissue for various amounts of time.

Other fixation methods may include, but are not limited to, various cryo-preservation or dry tissue fixation methods known are developed in the art for tissue fixation. Furthermore, fixation could be performed at various loads or strains, such as in vivo stretch ratios, as determined by the markers (dots placed upon the tissue prior to harvest). For example, and as referenced above and at the time of or prior to harvest, markings could be placed on the lung ligament 30 or visceral pleura 556 tissue (using a marker, for example), and measurements between markings could provide the harvester with information relating to said tissue at a natural (non-stretched state). When placing said harvested tissue upon a frame for fixation, for example, said tissue could be stretched at various degrees of stretch, with either raw distance stretch being known and/or a percentage stretch being known based upon the distance between markings at the natural (non-stretched) and stretched states.

With respect to overall pulmonary ligament 30 and/or visceral pleura 556 preparation, preservation of the tissue's elastin component is important so that the intended uses of the prepared pulmonary ligament 50 and/or processed visceral pleura 60 may still be considered. As the overall flexibility of the processed pulmonary ligament 50 and/or processed visceral pleura 60 preparation is important for various uses, efforts to preserve the elastin component may be reflected in the overall preparation methods. Different methods may be used to generate different products 100 of the present disclosure, such as different frames, tissue stretching, fixation duration, and/or a combination of the same. Furthermore, decellularization of the epithelial layer or layers of pulmonary ligament 30, for example, can be performed while also preserving/keeping the elastin scaffolds. As is known, the biologically occurring pulmonary ligament includes a layer of mesothelial cells (a specialized type of epithelial cells) on each side of the ligament. In addition, storage can be had using saline and/or an additional preservative, so that the product 100 is safe to use when needed.

Pulmonary ligaments 30 and/or visceral pleura 556, for potential use in connection with the present disclosure, can be harvested from any number of mammalian species and used in the same or other species. For example, pulmonary ligaments 30 and/or visceral pleura 556 can be harvested from pigs, horses, cows, goats, sheep, etc., and used to treat the same species or different species, including humans. Further, pulmonary ligaments 30 and/or visceral pleura 556 could be harvested from one human and used to treat another human. For long or short term storage, for example, pulmonary ligaments 30 and/or visceral pleura 556 (and/or processed ligament 50, processed visceral pleura 60, and/or products 100 of the present disclosure) may be preserved by freezing in liquid nitrogen (−198° C. in at least one example). So to ensure that fixed tissue thickness, stiffness, strength, and/or micro-structure do not change (or substantially change) over time, various short- and/or long-term storage mechanisms may be used.

In at least one embodiment of a method of preparing fixed/processed lung ligament 30 and/or visceral pleura 556 tissue of the present disclosure, the method includes the steps of obtaining a heart/lung block (such as from a slaughterhouse), placing the heart/lung block in cold saline (or another suitable solution at various temperatures) for transport as needed, isolating the lung ligament 30 and/or visceral pleura 556 tissue, and fixing the same as referenced herein. Such a method may be performed while taking precautions/steps to avoid tissue, perforations, fenestrations, and/or blood vessels or infiltrations therein.

In at least one embodiment of a product of the present disclosure, the product is not treated with a fixative. Instead, the product, in at least one embodiment, is harvested from a mammal and used in connection with one or more procedures or as one or more products reference herein without the use of a fixative. In certain aspects, such non-fixed pulmonary ligament products can be acellular, e.g., after treatment with one or more decellularization agents, and/or sterile.

In additional embodiments, provided are medical articles (exemplary products 100), such as kits 525, shown in block diagram form in FIG. 5E, that may include processed pulmonary ligament 50, processed visceral pleura 60 tissue, and/or a product 100, sterilely enclosed within packaging 530. A sterile condition of pulmonary ligament 50, processed visceral pleura 60 tissue, and/or a product 100 within the packaging 525 may be achieved, for example, by terminal sterilization using irradiation, ethylene oxide gas, or any other suitable sterilization technique, and the materials and other properties of the medical packaging can be selected accordingly.

Uses of a processed pulmonary ligament 50 and/or processed visceral pleura 60, as referenced above, include, but are not limited to, the following applications:

a. As a cover for various stents, such for as coronary stents, peripheral stents (porto cava shunts), aortic stents, neurological stents, esophageal stents, biliary tract stents, and the like.

b. As various types of biological tissue valves, including, but not limited to, venous and/or arterial valves, which may have various leaflet configurations, such as monocusp, bileaflet, trileaflet, and others.

c. As a cover for saphenous vein bypasses, thus avoiding vein over-distension.

d. As a patch, in various cardiac and other surgical procedures, such as ventricular reconstruction, an arterial patch, a venous patch (such as a carotid endarterectomy), or to repair other holes.

e. As a placement around the ascending aorta after surgery to avoid aortic aneurysm formation in hypertensive patients.

f. As a membrane in cardiac, thoracic, or general surgery to avoid adhesion in reoperations (valvular, transplants, left ventricular assist device (LVAD), coronary artery bypass graft (CABG), pediatric surgery, or general surgery).

g. As a cover for LVAD diaphragms or a total artificial heart diaphragm.

h. As a cover for the synthetic net in hernia repair and abdominal dehiscense.

i. As a biologic skin substitute in burn patients avoiding infection and loss of proteins, water.

j. As a cover for organs such as the heart (to limit dilation of the left ventricle, for example), stomach, urinary bladder, and to avoid overdistension and/or to prevent adhesion especially in laparoscopic procedures of diabetic patients.

k. As a reinforcement of a suture line, such as with ventricular aneurysm repair, bariatric surgery, and fistulae repair for intestines, bronchus, and esophagus.

l. As a structure for biological composite tubes, such as stented or stentless valves for inclusion within a biological tube, which can be used, for example, in ascending aortic aneurysm (AAA) replacement or pulmonary artery replacement.

m. In orthopedic surgery, such as with tendon replacement (having advantages in resistance and elasticity), total or partial replacement of the articular capsulae during surgery of the hip, elbow, knee, and/or the like, and/or as a cover for various orthopedic prosthetic devices.

n. As a cover for neurosurgical applications, such as a cover of part of the brain surface during tumor resection or resection of the skull.

o. In urologic surgery, such as in connection with reconstruction of a partial or total urinary bladder and/or urethral resection.

p. In gynecological surgery, such as in connection with vaginal reconstruction after tumor resection or other trauma, with reconstruction of perineal muscles to fix the urinary bladder, or with uterus prolapse.

q. In head & neck surgery, such as in connection with reconstructive surgery, replacement of muscles (requiring elasticity and resistance), and as a cover for a maxillary prosthesis.

r. In connection with other trauma, such as treating vehicular accident victims by covering complex wounds until surgical repair, which may be complex, can take place.

Figure 6B:
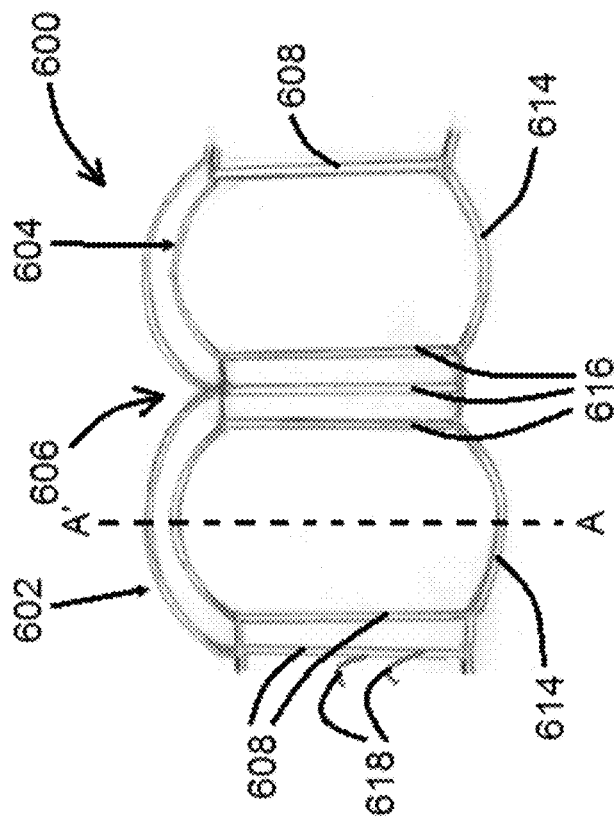
FIGS. 6A and 6B show a bileaflet frame configuration, according to an exemplary embodiment of the present disclosure.
Figure 6A:
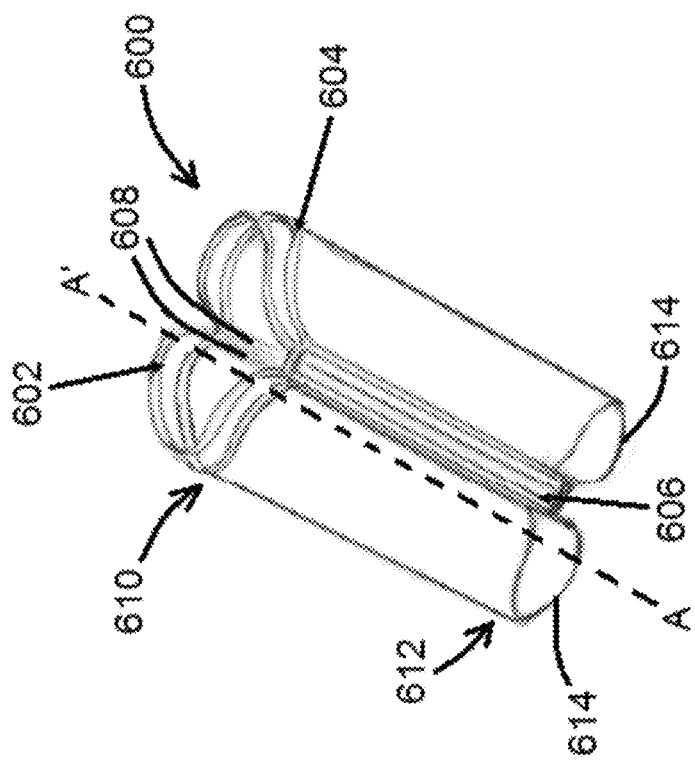

In view of the various uses of processed pulmonary ligament 50 and/or processed visceral pleura 60 to create various products 100 of the present disclosure, said ligament 50 and/or visceral pleura 60 may be used to produce products 100 configured as stents and/or stent valves 400 as follows. FIGS. 6A and 6B show closed and opened stent valve frames, respectively, for use with various products 100 of the present disclosure. As shown in FIGS. 6A and 6B, an exemplary product 100 of the present disclosure comprises a frame 600, with said frames 600, in various embodiments, comprising at least one superior arm 602 and at least one inferior arm 604. Arms 602, 604, as shown in FIGS. 6A and 6B, may be positioned at or near a relative end of frame 600, and may be parallel or substantially parallel to one another. Frames 600, as shown in FIGS. 6A and 6B, further comprise a connection portion 606, and optionally one or more vertical bars 608 extending along an elongate axis (A-A' as shown therein) to provide additional overall stability. As shown in FIG. 6B, an exemplary frame 600 comprises three vertical bars 608 extending along axis A-A' along a portion of a length of frame 600 from a first end 610 to a second end 612.

At or near the relative second end 612 of frame 600, one or more lower arms 614 may be present, which may, as shown in FIG. 6B, connect to one or more vertical bars 608 and/or one or more elements of connection portion 606. A combination of vertical bars 608, as referenced in further detail below, may comprise a connection portion 606. Frames 600, or portions thereof, may comprise a number of biologically-compatible materials including, but not limited to, nitinol, chromium, cadmium, molybdenum, nickel, a nickel composite (such as, for example, nickel-cadmium and/or nickel-chromium), nitinol palladium, palladium, cobalt, platinum, and/or stainless steel.

Connection portion 606 is shown in FIG. 6B as being an element of an exemplary frame 600 coupling to one or more of superior arm(s) 602, inferior arm(s) 604, vertical bar(s) 608, and lower arm(s) 614. In at least one embodiment, and as shown in FIG. 6B, connection portion 606 comprises a plurality of connection bars 616, which are used to connect one or more processed ligaments 50 and/or visceral pleura 60, or one or more other bodily tissues having the necessary stretchability and durability properties necessary to be useful in connection with one or more products 100 of the present disclosure, to frame 600 as referenced in further detail herein. As referenced herein, a "tissue" may be referred to as a ligament 50 and/or visceral pleura 60, and ligament 50 and/or visceral pleura 60, in at least one embodiment, may comprise another non-ligament tissue having the necessary properties noted above.

As noted above, a plurality of vertical bars 608 may also comprise a connection portion 606 of the present disclosure. Therefore, and depending on how portions of frame 600 are viewed, the exemplary frame shown in FIGS. 6A and 6B may comprise one connection portion 606 and a plurality of vertical bars 606, or they may comprise two connection portions 606, with one connection portion 606 comprising connection bars 616 and the other connection portion 606 comprising vertical bars 608. In addition, and as shown in FIG. 6B, various frames 600 of the present disclosure may comprise one or more barbs 618 positioned along various portions of frames 600 (such as vertical bars 608, connection bars 616, and/or other components) to facilitate securing a product 100 within a mammalian luminal organ (to prevent migration), and/or to facilitate securing the tissue (such as ligament 50 and/or visceral pleura 60) to frame 600.

Figure 7A:
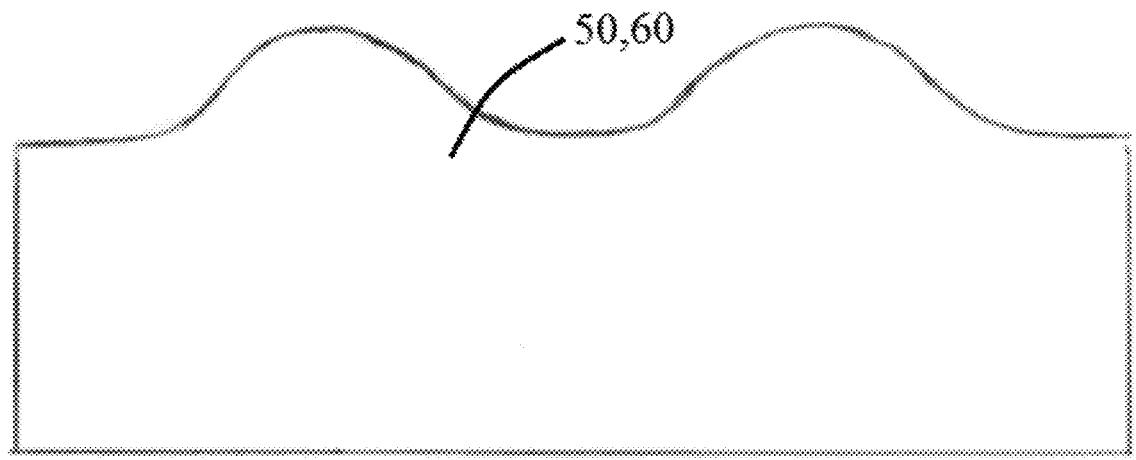
FIG. 7A shows a portion of a mammalian tissue cut/shaped to fit along a bileaflet frame, according to an exemplary embodiment of the present disclosure.

FIG. 7A shows an exemplary processed ligament 50 and/or visceral pleura 60 of the present disclosure molded for use with or as a bileaflet valve 400. As shown in FIGS. 6A and 6B, frame 600 is configured as two leaves with one connection portion 606. As referenced further herein, other frame 600 embodiments, such as being configured as a trileaflet valve 400 and as potentially a valve 400 with even more leaflets, may be produced consistent with the present disclosure. The processed ligament 50 and/or visceral pleura 60, as shown in FIG. 7A, is shaped substantially similar to an outer perimeter of frame 600 shown in FIGS. 6A and 6B. The shape shown in FIG. 7A represents processed ligament 50 and/or visceral pleura 60 configured so to create symmetrical valve leaflets upon placement of processed ligament 50 and/or visceral pleura 60 upon frame 600.

Figure 7B:
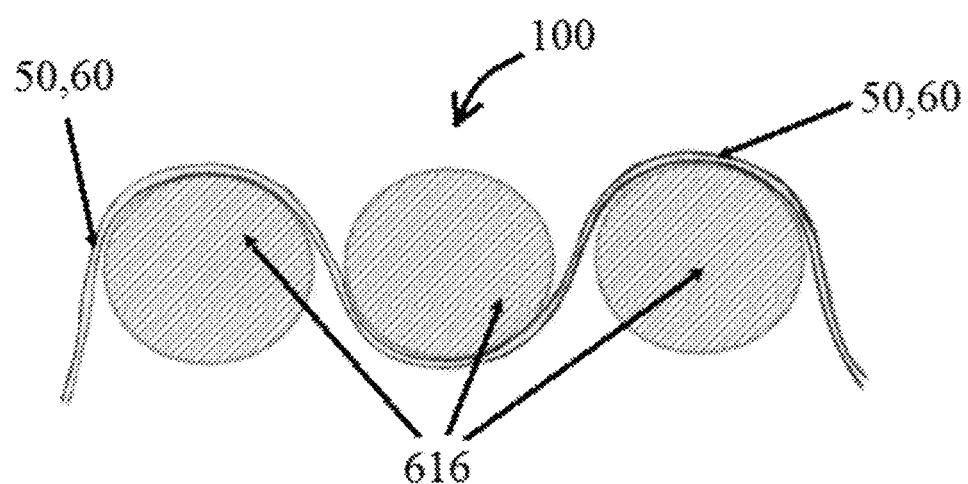
FIGS. 7B and 8A show how portions of mammalian tissue can be positioned within/around portions of a frame, according to exemplary embodiments of the present disclosure.

FIG. 7B shows a cross-section of a portion of an exemplary product 100 of the present disclosure, whereby individual connection bars 616 of an exemplary frame 600 are shown with a portion of a processed ligament 50 and/or visceral pleura 60 positioned therebetween. This view may be considered as an upper or lower cross-sectional view, and demonstrates an exemplary method of positioning a portion of processed ligament 50 and/or visceral pleura 60 within said connection bars 616 to secure the processed ligament 50 and/or visceral pleura 60 at that particular location within device 100.

Figure 8B:
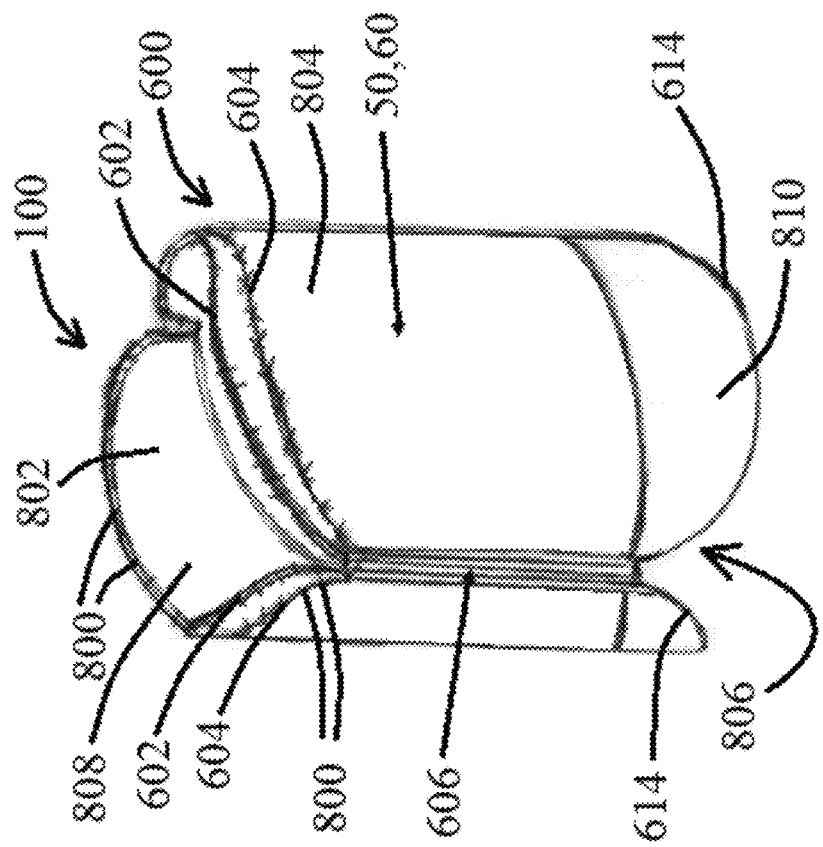
FIG. 8B shows an exemplary product having a bileaflet frame and a tissue positioned thereon, according to an exemplary embodiment of the present disclosure.
Figure 8A:
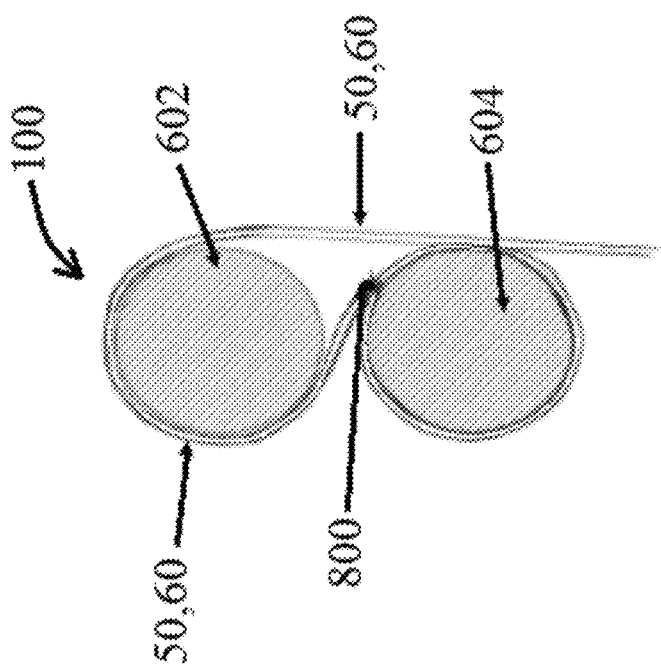

FIG. 8A shows another cross-section of a portion of an exemplary product 100 of the present disclosure, whereby a superior arm 602 and an inferior arm 604 of an exemplary frame 600 are shown with a portion of a processed ligament 50 and/or visceral pleura 60 positioned therebetween. This view shows an exemplary method of positioning a portion of processed ligament 50 and/or visceral pleura 60 within said arms 602, 604 to secure the processed ligament 50 and/or visceral pleura 60 at that particular location within device 100. One or more sutures 800, as shown in FIG. 8A, may be used to connect two portions of processed ligament 50 and/or visceral pleura 60 to one another to prevent movement of the same. For example, and as shown therein, an end portion of processed ligament 50 and/or visceral pleura 60 may be positioned upon or adjacent to inferior arm 604, and wrapped counter-clockwise (as shown in FIG. 8A) around inferior arm 604. When the wrapped portion of processed ligament 50 and/or visceral pleura 60 is positioned near the end portion, it may continue being wrapped around frame 600 by way of wrapping clockwise (as shown in FIG. 8A) around superior arm 602, and the processed ligament 50 and/or visceral pleura 60 may be sutured to itself as shown in the figure.

An exemplary embodiment of a product 100 of the present disclosure comprising a frame 600 and processed ligament 50 and/or visceral pleura 60 attached thereto is shown in FIG. 8B. Product 100 is shown in a closed configuration in FIG. 8B, whereby processed ligament 50 and/or visceral pleura 60 is sutured to itself and/or to portions of frame 600 at multiple locations to hold the processed ligament 50 and/or visceral pleura 60 in place. As shown in FIG. 8B, product 100 is configured as a bileaflet valve 400, which may be used, for example, as a venous valve or another type of valve. Leaflets 802 and 804 are identified in FIG. 8B. In various embodiments referenced herein, processed ligament 50 and/or visceral pleura 60 is sutured to frame 600, but sutures 800 are outside of the bloodstream (are not in contact with blood flow) when frame 600 with processed ligament 50 and/or visceral pleura 60 thereon (an exemplary product 100) is positioned within a mammalian luminal organ having blood flowing therethrough.

A completed product 100 (such as shown in FIG. 8B and in FIG. 10B described below) may be configured as a stent or stent valve 400. Configurations as a stent valve 400 would utilize leaflets 802 and 804 to control the flow of fluid through a lumen 806 defined within product 100. The direction of fluid flow of such an embodiment would be such that fluid would enter inlet portion 808 of product 100 and exit from outlet portion 810 of product 100, as shown in FIG. 8B. In such a configuration, product 100 could be positioned within a mammalian luminal organ, and fluid flow through said organ could continue through lumen 806 of product 100.

Figure 9B:
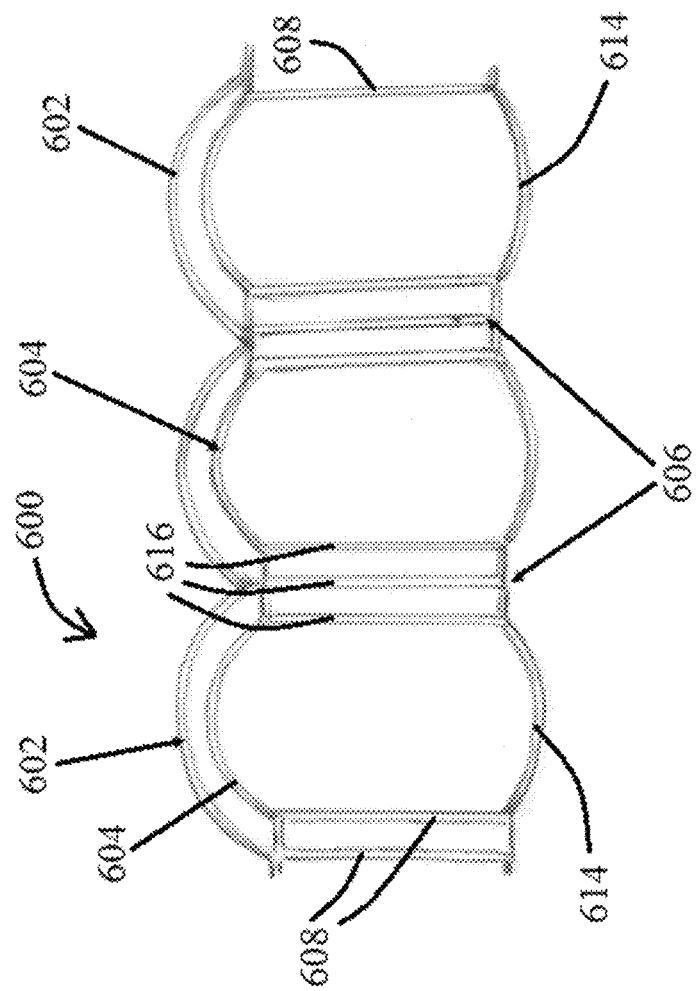
FIGS. 9A and 9B show a trileaflet frame configuration, according to an exemplary embodiment of the present disclosure.
Figure 9A:
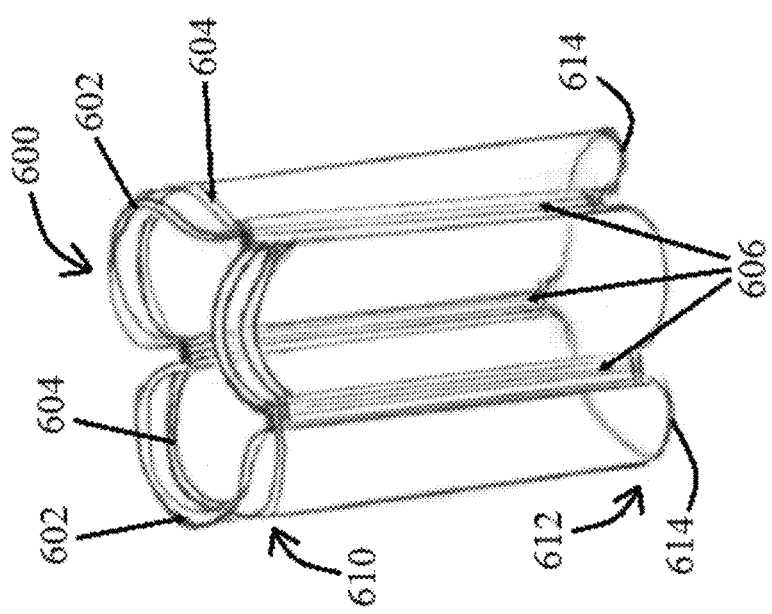

FIGS. 9A and 9B show additional exemplary closed and opened stent valve frames, respectively, for use with various products 100 of the present disclosure. As shown in FIGS. 9A and 9B, an exemplary product 100 of the present disclosure comprises a frame 600 configured for ultimate use as a trileaflet valve 400, with said frames 600, in various embodiments, comprising at least one superior arm 602 and at least one inferior arm 604. Arms 602, 604, as shown in FIGS. 9A and 9B, may be positioned at or near a relative end of frame 600. Frames 600, as shown in FIGS. 9A and 6B, further comprise two or more connection portions 606 (as referenced in further detail below), and optionally one or more vertical bars 608 extending along an elongate axis to provide additional overall stability. As shown in FIG. 9B, such an exemplary frame comprises three vertical bars 608 extending along a portion of a length of frame 600 from a first end 610 to a second end 612. At or near the relative second end 612 of frame 600, one or more lower arms 614 may be present, which may, as shown in FIG. 6B, connect to one or more vertical bars 608 and/or one or more elements of connection portion 606. A combination of vertical bars 608, as referenced herein, may comprise a connection portion 606.

Depending on how portions of frame 600 are viewed, the exemplary frame 600 shown in FIGS. 9A and 9B may comprise two connection portions 606 and a plurality of vertical bars 608, or they may comprise three connection portions 606, with two connection portions 606 comprising connection bars 616 and the other connection portion 606 comprising vertical bars 608. FIG. 9A shows frame 600 as having three connection portions 606, while the same frame 600, shown in FIG. 9B, shows two connection portions 606 and a plurality of vertical bars 608. The frames shown in FIGS. 9A and 9B are identical, however, with one being shown in a closed configuration (FIG. 9A) and the other being shown in a closed configuration (FIG. 9B).

Connection portions 606 are shown in FIG. 9B, for example, as being elements of an exemplary frame 600 coupling to one or more of superior arm(s) 602, inferior arm(s) 604, vertical bar(s) 608, and lower arm(s) 614. In at least one embodiment, and as shown in FIG. 9B, connection portions 606 comprise a plurality of connection bars 616, which are used to connect one or more processed ligaments 50 and/or visceral pleura 60 to frame 600 as referenced herein with respect to other frame 600 and/or product 100 embodiments.

FIG. 10A shows an exemplary processed ligament 50 and/or visceral pleura 60 of the present disclosure molded for use with as a trileaflet valve 400. As shown in FIGS. 9A and 9B, frame 600 is configured as three leaves with two or three connection portions 606, depending on how the frame 600 is viewed. The processed ligament 50 and/or visceral pleura 60, as shown in FIG. 10A, is shaped substantially similar to an outer perimeter of frame 600 shown in FIGS. 9A and 9B. The shape shown in FIG. 7A represents processed ligament 50 and/or visceral pleura 60 configured so to create symmetrical valve leaflets upon placement of processed ligament 50 and/or visceral pleura 60 upon frame 600.

An exemplary embodiment of a product 100 of the present disclosure comprising a frame 600 as shown in FIGS. 9A and 9B and a processed ligament 50 and/or visceral pleura 60 attached thereto is shown in FIG. 10B. Product 100 is shown in a closed configuration in FIG. 10B, whereby processed ligament 50 and/or visceral pleura 60 is sutured to itself and/or to portions of frame 600 at multiple locations to hold the processed ligament 50 and/or visceral pleura 60 in place. As shown in FIG. 10B, product 100 is configured as a trileaflet valve 400, which may be used, for example, as a venous valve or another type of valve. Leaflets 802, 804, and 1000 are identified in FIG. 10B.

Various products 100 of the present disclosure configured as valves 400, including products 100 shown in FIGS. 8B and 10B for example, and/or other valve 400 products of the present disclosure used with or without various frames, can have the processed ligament 50 and/or visceral pleura 60 positioned in specific configuration(s) to improve overall operation, effectiveness, and/or size of said products 100. Visceral pleura 556, and therefore processed visceral pleura 60, has one side with mesothelium (also referred to herein as a relatively smooth "mesothelial side"), and has an opposite side without mesothelium (also referred to herein as a relatively rough "non-mesothelial side"). As shown in FIG. 5F, the mesothelial side 860 of visceral pleura 556 is on a relative outside of the lung 34, while the non-mesothelial side 862 of visceral pleura 556 is on the relative inside of the lung 34.

For example, and in connection with various products 100 of the present disclosure using processed visceral pleura 60 as one or more valve 400 leaflets 802, 804, or 1000, processed visceral pleura 60 can be positioned in a way/configuration so that the side of processed visceral pleura 60 having mesothelium would be on the relative back of the valve 400 leaflet(s) 802, 804, and/or 1000, and so that the side of processed visceral pleura 60 without mesothelium would be on the relative front of the valve 400 leaflet(s) 802, 804, and/or 1000. In such a configuration, the mesothelial side 860 of processed visceral pleura 60 is on the back of leaflet(s) 802, 804, and/or 1000, where blood flow reversal exists as the valve 400 closes. The relatively smooth mesothelial side 860 would be in contact with blood flows more slowly, where shear stresses may be lower and reversing. As such, the rougher non-mesothelial 862 side of processed visceral pleura 60 would then be on the front of leaflet(s) 802, 804, and/or 1000, in contact with fast moving blood, because there is less of a risk of thrombosis as compared with the slower moving blood or shear stress.

Such a valve 400 (exemplary product 100) embodiment is shown in FIG. 10C positioned within a luminal organ 850, where valve leaflets 802, 804 (or more, less, or different leaflets, depending on valve 400 configuration) are shown therein. As shown therein, valve 400 is in contact with the wall(s) 852 of luminal organ 850, positioned within a lumen 854 defined therethrough. A mesothelial side 860 of processed visceral pleura 60 is on a relative back of leaflets 802, 804, and a non-mesothelial side 862 of processed visceral pleura 60 is on a relative front of leaflets 802, 804, as described above. Such a device embodiment 100 is one such embodiment referenced herein where processed ligament 50 and/or visceral pleura 60 is oriented in a specific direction. In at least another embodiment, for example, mesothelial side 860 of processed visceral pleura 60 would be on a relative front of leaflets 802, 804, and a non-mesothelial side 862 of processed visceral pleura 60 would be on a relative back of leaflets 802, 804.

Figure 11:
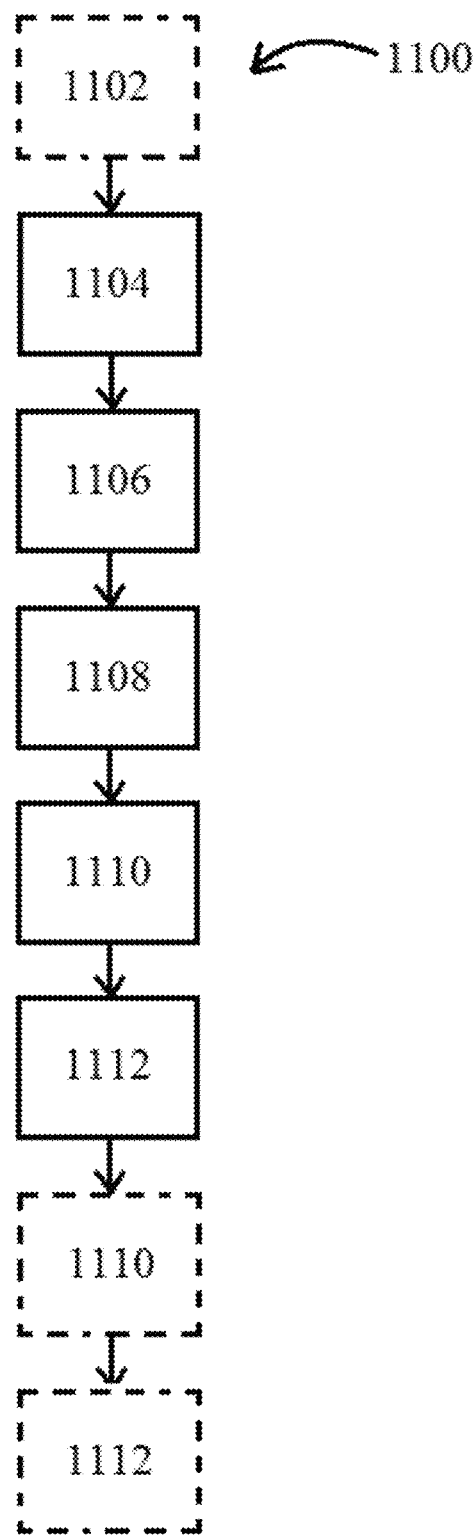
FIG. 11 shows steps of a method to manufacture a product, according to an exemplary embodiment of the present disclosure.

Exemplary products 100 of the present disclosure may be prepared as follows. In at least one method for preparing a product of the present disclosure, the method 1100, as shown by the method steps in FIG. 11, comprises the steps of preparing a bodily tissue (such as a processed ligament 50 and/or visceral pleura 60 or another bodily tissue having the necessary stretchability and durability properties necessary to be useful in connection with one or more products 100 of the present disclosure) (an exemplary tissue preparation step 1102, which may be optional, as the tissue may have been previously prepared and subsequently used in connection with method 1100), and shaping the bodily tissue (an exemplary tissue shaping step 1104) so that the tissue will fit around portions of an exemplary frame 600. In at least one embodiment, tissue preparation step comprises preparing a portion of tissue (such as pulmonary ligament 50 and/or visceral pleura 60) by way of excising the tissue from a mammalian body, removing any undesirable portions of tissue (such as those with holes or vessels therein), placing the tissue on a frame (to maintain a desired shape and/or amount of stretch), and fixing the tissue using glutaraldehyde and buffer, for example. Tissue shaping step 1104, in at least one embodiment, comprises stretching the tissue (such as lung ligament 50, visceral pleura 60, lung viscera, and/or another tissue) and cutting the tissue using a flat mold, for example.

In various embodiments, method 1100 further comprises the step of positioning the tissue around a mount (such as a cylindrical or conical mount, which may be made of acrylic or another suitable material) (an exemplary mounting step 1106), and positioning at least part of an exemplary frame 600 around the tissue positioned upon the mount (an exemplary frame positioning step 1108). Tissue may then be passed around various bars of frame 600 (such as connection bars 616 of connection portion 606 or other components of frame 600), such as shown in FIG. 7B (an exemplary tissue connection step 1110), and various sutures 800 may be used to suture portions of tissue together to form the overall relatively cylindrical shape (an exemplary suturing step 1112). Tissue connection step 1110 may be repeated, such as by allowing the inflow portion of the tissue cylinder to pass through the superior and inferior parallel arms (arms 602, 604) to cover arms 602, 604, as shown in FIG. 8A, for example. Additional sutures may then be used, by way of repeating suturing step 1112, so that the border of the tissue is sutured with, for example, a continuing suture line facilitated by using a polypropylene 7-0 or 8-0 needle, for example, or another type/size of needle, to result in a product 100 as shown in FIGS. 8B, 10B, or in other product 100 embodiments.

After product 100 is prepared, it can be delivered into a mammalian luminal organ in a number of ways. One method of delivery involves gently crimping or compressing product 100 so that its overall cross-section decreases, to facilitate delivery into the luminal organ. This delivery may be facilitated using a catheter or a wire, for example. If delivered by catheter, and it at least one embodiment (such as with a nickel-cadmium product 100 of the present disclosure), a balloon catheter may be used, with product 100 positioned at the balloon. Inflation of the balloon, using a gas or a liquid, for example, can cause the balloon to expand and thus cause product 100 to expand and be positioned within the luminal organ. Deflation of the balloon can then facilitate removal of the catheter. Furthermore, products 100 of the present disclosure may be autoexpandable, such as those comprising nitinol, whereby delivery using a balloon catheter may not be necessary. Delivery of products 100 of the present disclosure is not limited to the aforementioned delivery methods, as other methods of delivering implantable devices into a mammalian luminal organ may be used to deliver products 100.

The present disclosure also includes disclosure of uses of various processed ligaments 50, processed visceral pleura 60, and/or products 100 in connection with various Transcatheter Aortic-Valve Implantation (TAVI) and other percutaneous approaches. TAVI involves the placement of an aortic valve within a patient using a catheter to avoid a traditional open surgical procedure and to minimize general stresses to the patient during the procedure. This procedure is used when a patient's aortic valve fails to operate as desired, and can effectively prolong the patient's life without requiring additional surgical and non-surgical procedures, including but not limited to heart transplant. Certain patients may not be suitable for surgery, such as those with such a severe aortic stenosis that would preclude an open surgical procedure, allowing TAVI to be considered. Processed ligaments 50 and/or processed visceral pleura 60 of the present disclosure can be used with current or potentially developed aortic valve frames/housings, or products 100 of the present disclosure comprising one or more frames 600, can be used as aortic or other valves as referenced herein. Furthermore, various processed ligaments 50, processed visceral pleura 60, and/or products 100 can be delivered percutaneously or surgically, using various catheters or wires or other surgical tools for example, avoiding more invasive surgical procedures.

As processed lung ligaments 50 and processed visceral pleura 60 of the present disclosure are thinner than pericardium, which is currently used in TAVI or used with any number of valve procedures to replace and/or insert various aortic, mitral, pulmonary, tricuspid, and/or other percutaneous valves, the overall dimensions of the final delivery system, whether it be a product 100 of the present disclosure or processed ligament 50 and/or processed visceral pleura 60 of the present disclosure coupled with another type of frame or housing, can be significantly reduced by using processed ligaments 50 and/or processed visceral pleura 60 instead of pericardium. The bulk of a traditional TAVI product is not the stent frame itself, but the pericardial tissue, and using processed ligament 50 and/or processed visceral pleura 60 of the present disclosure instead of pericardial tissue would notably and beneficially decrease the overall bulk of said product 100. Having a product 100 configured smaller than a traditional TAVI product, for example, would not only allow for more potential manipulation of said product 100 in connection with delivery, expansion, and/or placement as compared to traditional products, but also would allow for smaller delivery devices (catheters, for example) to be used, therefore decreasing the potential aperture/opening made into a femoral or iliac artery, for example, during product 100 delivery. For example, reducing a catheter from 18 French to 12 French, or from 12 French to 8 French, would permit a smaller delivery aperture/opening to be used. This would also reduce or eliminate the need for a potential closure device, reduce patient bleeding, reduce overall patient trauma, and/or simplify delivery, placement, and/or expansion of relatively smaller products 100.

There are various advantages to using products 100 of the present disclosure as valves and/or as other medical implantable devices. For example, and with various embodiments described herein, products 100 are configured to avoid suture of commissure and thus spread out the stress, and there is may be no sutures 800 that come in contact with blood. Frames 600 may have a less metallic stent design, and may also comprise a completed inflow metal stent tissue cover. With respect to the different product 100 borders, various products 100 of the present disclosure have no suture line at the inflow border, and no tissue (such as processed lung ligament 50 and/or visceral pleura 60) fixation at the stent border. The double parallel (or relatively/substantially parallel) arms (superior arm(s) 602 and inferior arm(s) 604)) are configured so that a tissue (such as ligament 50 and/or visceral pleura 60) can be passed around them. Furthermore, and in at least one product 100 embodiment, the suture line is not submitted to the inflow stress and blood flow, and the suture knot is not in contact with the inflow blood.

Other advantages of products 100 of the present disclosure also exist. For example, and when preparing said products 100, the commissure are obtained by passing the tissue around the various vertical arms with the advantage of no suture and diffuse tissue stress along the vertical length of the bars. The various frame 600 designs and their tissue covers have the advantage of very little contact of any metallic frame material with the blood flow. The valves themselves have excellent leaflet coaptation, good valve sinus formation, and no blood stagnation areas when developed/configured as described herein and used within a mammalian blood vessel. Furthermore, the inflow stent area covered with tissue is in broad contact with the venous wall with the advantage of tissue-tissue contact when positioned within a mammalian vein.

While various embodiments of biological tissue products and methods of using and generating the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A product, comprising:
a frame configured to retain a mammalian tissue thereon; and
the mammalian tissue coupled to the frame;
wherein when the product is positioned within a mammalian luminal organ, fluid native to the mammalian luminal organ may pass through a lumen defined within the product;
wherein the mammalian tissue comprises mammalian pulmonary ligament; and
wherein the mammalian tissue is fixed.

2. The product of claim 1, wherein the mammalian tissue is chemically fixed.

3. The product of claim 1, wherein the mammalian tissue is fixed using a fixative selected from the group consisting of glutaraldehyde, formaldehyde, and glycerol.

4. The product of claim 1, wherein the mammalian tissue is fixed using a fixative within a HEPES or phosphate buffer.

5. The product of claim 1, wherein the mammalian tissue is fixed using a fixation procedure selected from the group consisting of aqueous fixation, cryo-preservation, and dry tissue fixation.

6. The product of claim 1, wherein the mammalian tissue is fixed using a fixative that is buffered.

7. The product of claim 1, wherein a segment of the mammalian tissue is decellularized.

8. The product of claim 1, wherein the mammalian tissue is sterilized.

9. A product, comprising:
a frame configured to retain a mammalian tissue thereon; and
the mammalian tissue coupled to the frame;
wherein when the product is positioned within a mammalian luminal organ, fluid native to the mammalian luminal organ may pass through a lumen defined within the product;
wherein the product is configured as a stent valve;

wherein the mammalian tissue comprises pulmonary ligament; and wherein the mammalian tissue is fixed.

10. The product of claim 9, wherein the mammalian tissue is chemically fixed.

11. The product of claim 9, wherein the mammalian tissue is fixed using a fixative selected from the group consisting of glutaraldehyde, formaldehyde, and glycerol.

12. The product of claim 9, wherein a segment of the mammalian tissue is decellularized.

* * * * *